US012083174B2

(12) United States Patent
Bertholet Girardin et al.

(10) Patent No.: US 12,083,174 B2
(45) Date of Patent: Sep. 10, 2024

(54) IMMUNOGENIC COMPOSITIONS AND USES THEREOF

(71) Applicant: GLAXOSMITHKLINE BIOLOGICALS SA, Rixensart (BE)

(72) Inventors: Sylvie Bertholet Girardin, Rockville, MD (US); Arun Kumar, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 125 days.

(21) Appl. No.: 17/268,647

(22) PCT Filed: Aug. 16, 2019

(86) PCT No.: PCT/EP2019/072052

§ 371 (c)(1),
(2) Date: Feb. 16, 2021

(87) PCT Pub. No.: WO2020/035609

PCT Pub. Date: Feb. 20, 2020

(65) Prior Publication Data

US 2021/0252133 A1 Aug. 19, 2021

Related U.S. Application Data

(60) Provisional application No. 62/719,219, filed on Aug. 17, 2018.

(51) Int. Cl.
*A61K 39/145* (2006.01)
*A61K 39/00* (2006.01)

(52) U.S. Cl.
CPC ........ *A61K 39/145* (2013.01); *A61K 2039/53* (2013.01); *A61K 2039/55555* (2013.01); *A61K 2039/55566* (2013.01); *A61K 2039/70* (2013.01)

(58) Field of Classification Search
CPC ........ A61K 2039/55555; A61K 39/145; A61K 39/295; A61K 2039/55566; A61K 2039/70; A61P 31/16; C12N 2760/16234; C12N 2760/16311; C12N 2780/00; C12N 2760/16111; C12N 2760/16211; C12N 2760/16011; C12N 2760/00; C12N 2740/00
See application file for complete search history.

(56) References Cited

U.S. PATENT DOCUMENTS 10,022,436 B2 * 7/2018 Henderson ........... A61K 9/5146
2014/0193484 A1 * 7/2014 Bertholet Girardin ...................... A61P 37/04 424/210.1

FOREIGN PATENT DOCUMENTS

| | | | |
|---|---|---|---|
| CN | 106822887 | A | 6/2017 |
| WO | 2013006837 | A1 | 1/2013 |
| WO | 2013006842 | A2 | 1/2013 |
| WO | 2014108515 | A1 | 7/2014 |

OTHER PUBLICATIONS

International Search Report and Written Opinion for corresponding International Application No. PCT/EP2019/072052, dated Apr. 30, 2020 (24 pages).
Vogel et al., Molecular Therapy, 26(2): 446-455 (2018).
Scorza et al., Vaccines, 6(2): 1-15 (2018).
Brito et al., Molecular Therapy, 22(12): 2118-2129 (2014).
Magini et al., PLOS One, 11(8): 1-25 (2016).
Lundstrom et al., Vaccines, 4(4): 1-23 (2016).
Ulmer et al., Current Opinion in Immunology, 41:18-22 (2016).
Tisa et al., Journal of Preventive Medicine and Hygiene, 57(1): E28-E33 (2016).
Hekele et al., Emerging Microbes & Infections, 2(8): 1-7 (2013).
Huber et al., Vaccine, 27(8): 1192-1200 (2009).
English language translation of Office Action in corresponding Japanese Patent Application No. 2021-507889, dated Aug. 1, 2023 (4 pages).
Wikipedia, "Influenza A virus", retrieved on Dec. 8, 2023, from https://en.wikipedia.org/w/index.php?title=Influenza_A_virus&oldid=1187100557.

* cited by examiner

*Primary Examiner* — Bao Q Li

(57) ABSTRACT

The present invention is in the field of treating and/or preventing viral infections. In particular, the present invention relates to immunogenic or pharmaceutical compositions comprising self-replicating RNA molecules that encode influenzavirus antigens for treating and/or preventing influenza infections.

16 Claims, 10 Drawing Sheets

Figure 1A:
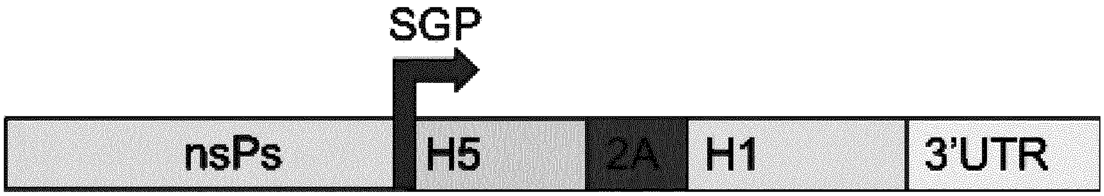

Specification includes a Sequence Listing.

(i)

(ii)

| Group | Group name | Antigen (µg/mouse) | Adjuvant/ formulation | Route |
|---|---|---|---|---|
| 1 | PBS | | RV01 | IM |
| 2 | SAM H3 (Bilthoven, Bangkok, Fujain) | 0.3 (0.1 each) | RV01 | IM |
| 3 | SAM H3 (Beijing, Brisbane, Texas) | 0.3 (0.1 each) | RV01 | IM |
| 4 | SAM H1, H5, H7 (California, PR8, Shanghai, turkey) | 0.4 (0.1 each) | RV01 | IM |
| 5 | SAM H3 (Bilthoven, Bangkok, Fujain, Beijing, Brisbane, Texas) | 0.6 (0.1 each) | RV01 | IM |
| 6 | SAM H3, H1, H5, H7 (All 10 SAM replicons) | 1.0 (0.1 each) | RV01 | IM |

(A)

(B)

IMMUNOGENIC COMPOSITIONS AND USES THEREOF

STATEMENT REGARDING SPONSORED RESEARCH

This invention was made with Government support under Agreement No. HR0011-12-3-0001 awarded by DARPA. The Government has certain rights in the invention. The work leading to this invention also received funding from the People Programme (Marie Curie Actions) of the European Union's Seventh Framework Programme (FP7/2007-2013) under REA grant agreement number 626283.

REFERENCE TO SEQUENCE LISTING SUBMITTED ELECTRONICALLY

This application contains a sequence listing, which was submitted electronically via European Patent Office Online Filing as an ASCII formatted sequence listing with the file name "eolf-othd-000001.txt", creation date of 20 Feb. 2020, and having a size of 101 KB. The sequence listing submitted via European Patent Office Online Filing, which was communicated to the United States Patent and Trademark Office, is part of the specification and is herein incorporated by reference in its entirety.

FIELD OF THE INVENTION

The present invention is in the field of treating and/or preventing viral infections. In particular, the present invention relates to immunogenic or pharmaceutical compositions comprising self-replicating RNA molecules that encode influenza virus antigens for treating and/or preventing influenza infections.

BACKGROUND TO THE INVENTION

Influenza (flu) virus infections are liable for thousands of deaths annually worldwide and are responsible for an economic burden amounting to billions of dollars. Vaccines are the primary tool for prevention and control of the disease but as the flu virus frequently changes, the vaccines have to be reformulated every year. Available flu vaccines are strain-specific and provide protection against only vaccine strain viruses. Seasonal antigenic shifts resulting from frequent mutation of the viral surface proteins haemagglutinin (HA) and neuraminidase (NA) makes the previous season's vaccine largely ineffective in the following year. Further, the unpredictability of flu pandemics precipitated by antigenic shifts requires constant surveillance and significant investment in an attempt to maintain a level of preparedness. In view of these limitations, there is an urgent need for the development of novel flu vaccines that provide durable protection against multiple strains and subtypes, including future pandemic strains.

Live attenuated influenza vaccines (LAIV) and inactivated influenza vaccines (IIV) are presently used for vaccination in all age groups. Both vaccines have been found to induce homologous and heterologous immunity in human and in animals. However, adjuvanted subunit or split vaccines have been shown to induce strong HA-specific CD4 T-cell responses and high-titer HA-specific antibodies with a more diverse repertoire (Dormitzer et al Immunol Rev 2011; 239:167-77 and Khurana et al, Sci Transl Med 2011; 3:85ra48. Doi:10.1126/scitranslmed.3002336). The cumbersome production process for these vaccines involves the large-scale production of infectious virus in eggs and as a result antigenic domains of the vaccine viruses are altered. Therefore, new approaches need to be developed to avoid complex production processes that may alter the vaccine virus and the effectiveness of the resulting vaccine and to provide vaccines that show protection against multiple strains and/or subtypes of influenza virus.

SUMMARY OF THE INVENTION

Provided herein in a first aspect is an immunogenic composition comprising: (i) a first self-replicating RNA molecule encoding a polypeptide comprising a first antigen and (ii) a second self-replicating RNA molecule encoding a polypeptide comprising a second antigen, wherein the first and second antigens are both from influenza virus but the first antigen is from a different strain of influenza virus to the second antigen.

In further aspects, is provided:

- a pharmaceutical composition comprising an immunogenic composition described above and a pharmaceutically acceptable carrier,
- the immunogenic composition or the pharmaceutical composition described above for use as a vaccine,
- the immunogenic composition or the pharmaceutical composition described above for use in the prevention of influenza,
- a method of prevention and/or treatment against influenza disease, comprising the administration of the immunogenic composition or pharmaceutical composition described above to a person in need thereof,
- a method for inducing an immune response against influenza virus infection in a subject comprising administering to the subject an immunologically effective amount of the pharmaceutical composition or the immunogenic composition described above,
- a method of prevention and/or treatment against influenza disease, comprising (i) the administration of a first immunogenic composition comprising a first self-replicating RNA molecule and pharmaceutically acceptable carrier and (ii) simultaneous or sequential administration of a second immunogenic composition comprising a second self-replicating RNA molecule and pharmaceutically acceptable carrier, wherein the first and second self-replicating RNA molecules encode a polypeptide encoding an antigen from influenza virus but the first self-replicating RNA molecule encodes an antigen from a different strain of influenza to that encoded by the second self-replicating RNA molecule,
- a first immunogenic composition comprising a first self-replicating RNA molecule and a pharmaceutically acceptable carrier for use in a method of preventing influenza disease, said method comprising administration to a subject in need the first immunogenic composition followed by administration of a second immunogenic composition comprising a self-replicating RNA molecule and a pharmaceutically acceptable carrier, wherein the first and second self-replicating RNA molecules each encode a polypeptide comprising an antigen, wherein the antigen is from influenza virus but the antigen encoded by the first self-replicating RNA molecule is from a different strain of influenza virus to that encoded by the second self-replicating RNA molecule,
- a method of preparing an immunogenic composition as described above, the method comprising: (i) providing at least one lipid which forms nanoparticles; (ii) providing an aqueous solution comprising the self-replicating RNA molecules; and (iii) combining the aqueous solution of (ii) and the at least one lipid of (i), thereby preparing the composition.

a method of preparing an immunogenic composition as described above, the method comprising: (i) providing an oil-in-water emulsion; (ii) providing an aqueous solution comprising the self-replicating RNA molecules; and (iii) combining the aqueous solution of (ii) and the oil-in-water emulsion of (i), thereby preparing the composition.

DESCRIPTION OF DRAWINGS/FIGURES

Figure 1B:
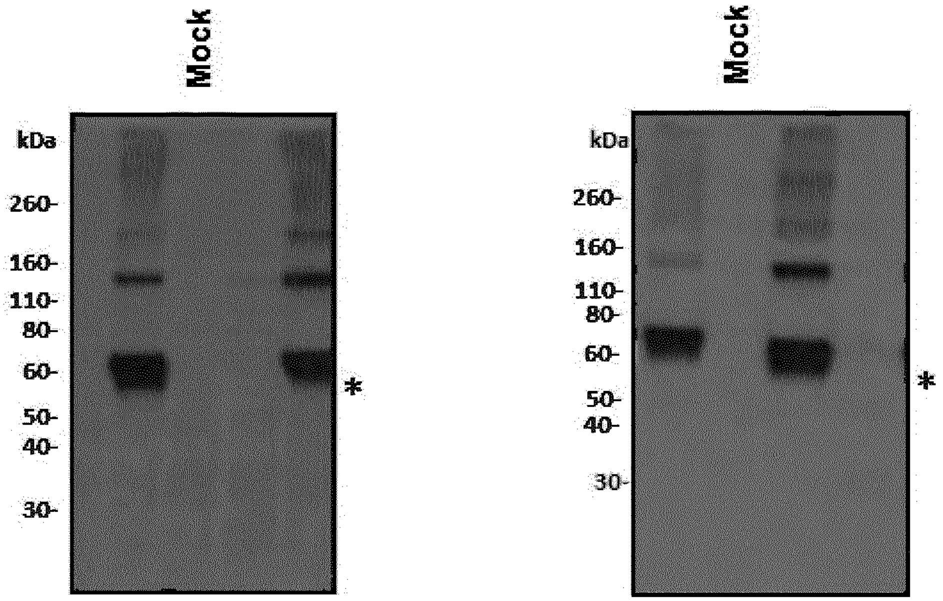

FIG. 1: Schematic representation and characterization of bi-cistronic SAM (H5-H1). (a) Bicistronic replicon construct used to test the multiple expression of HA genes. (b) HA protein expression in BHK cells transfected with H1-SAM (Lane 1), H5-SAM (Lane 3), H5H1-SAM (Lane 4) or mock-treated (Lane 3). Cell lysates were analyzed by non-reducing SDS-PAGE followed by Western Blot analyses with HA-strain specific serum: i) Anti-A/California/07/2009 (H1N1) HA Serum (NIBSC, London, UK) used to detect H1; ii) Anti-A/turkey/Turkey/1/05 (H5N1) HA Serum (NIBSC, London, UK) used to detect H5. The monomeric form of HA is indicated by an asterisk (62 kDa). SGP=subgenomic promoter; H1=H1 HA gene from influenza A/California/07/2009 (H1N1) virus strain; H5=H5 HA gene from A/turkey/Turkey/01/2005 (H5N1) virus strain; 2A=full length 2A-driven sequence; nsPs=non-structural replicon proteins; HA * monomer.

Figures 2A, 2B, 2C, 2D:
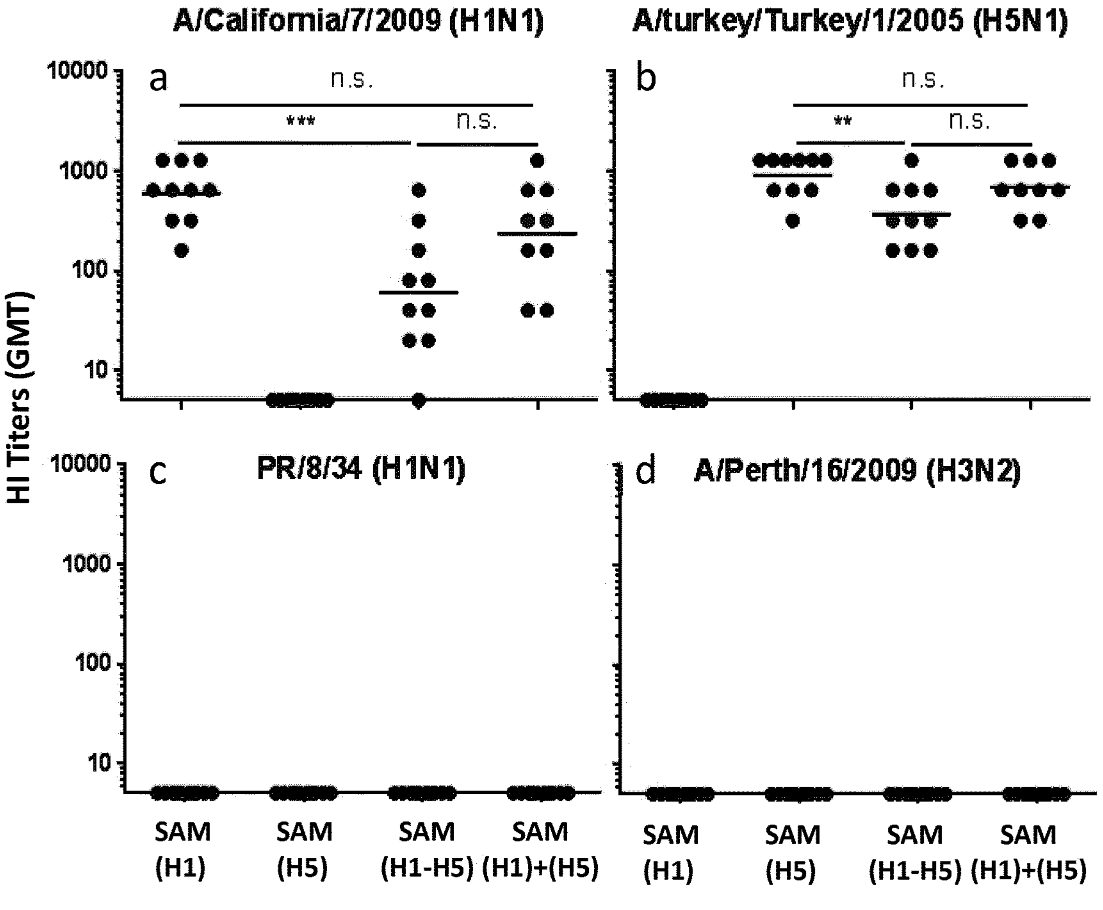
Figures 2E, 2F, 2G, 2H, 2I, 2J, 2K, 2L, 2M:
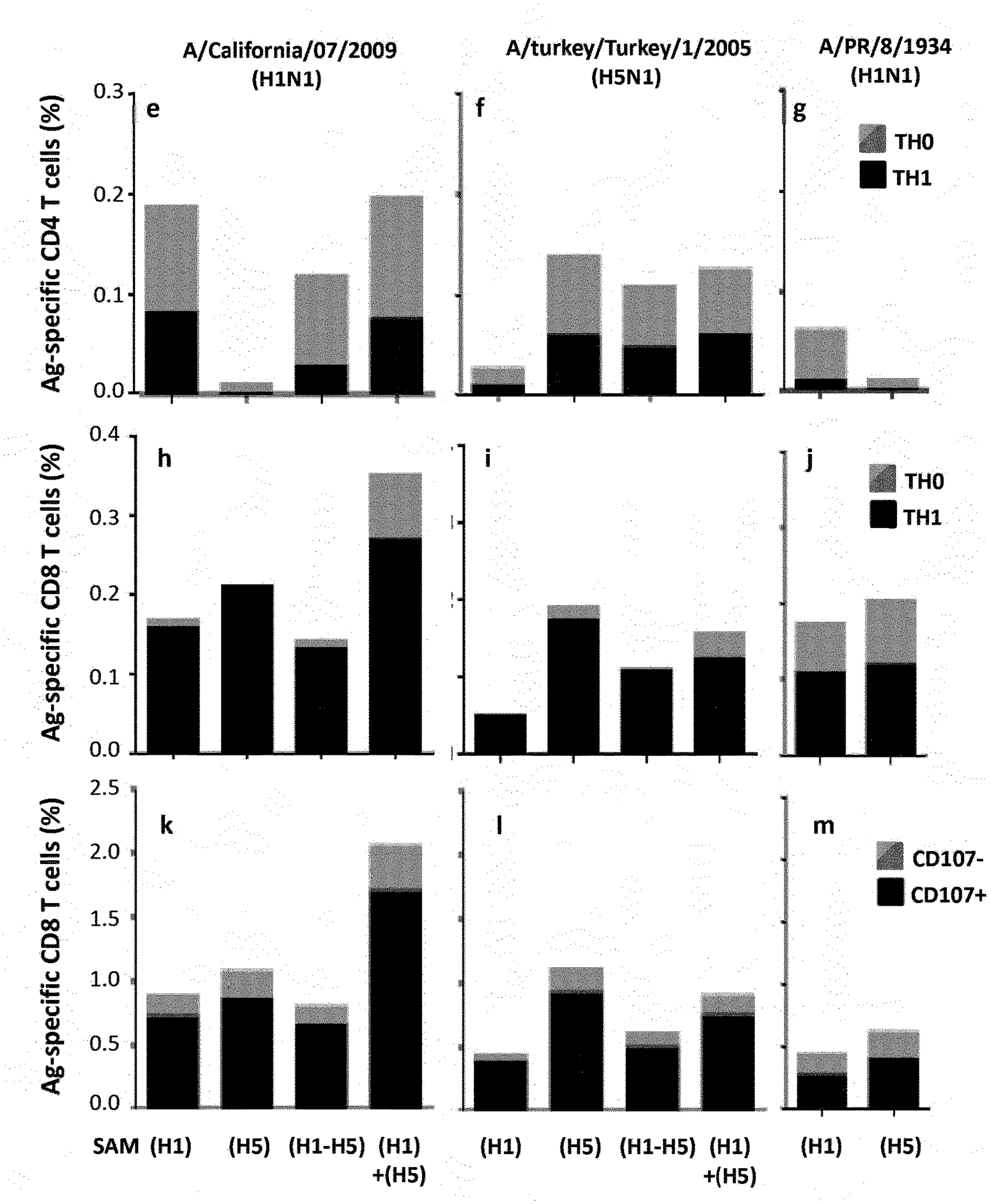

FIG. 2: Immunogenicity of SAM monocistronic and bicistronic SAM(HA)/LNP candidate vaccines. Mice (n=10) were immunized i.m. on day 0 and day 21 with SAM(H1), SAM(H5), SAM(H5-H1) and SAM(H1)+SAM(H5) at 0.1 µg. Sera and spleens were collected 2 weeks after second immunization. Sera samples were analyzed for A/California/07/2009 (H1N1), A/turkey/Turkey/5/2005 (H5N1), A/PR/8/1934 (H1N1) and A/Perth/16/2009 (H3N2)-specific HI titres (a, b, c, d). Splenocytes (n=6) were stimulated in-vitro with H1-Cal, H1-PR8 and H5-turkey peptide pools (e to m), and T cells were analyzed for cytokine production by flow cytometry. The bars represent the cumulative frequency of H1-Cal, H5-turkey, H1-PR8-specific $CD4^+$ T cells (e to g) and $CD8^+$ T cells (h to j) expressing cytokines. CD107a expression by CD8 (k to m).

Statistical analyses were performed using the Mann-Whitney U test. P<0.01, *P<0.001.

Figures 3A, 3B, 3C, 3D, 3E, 3F, 3G:
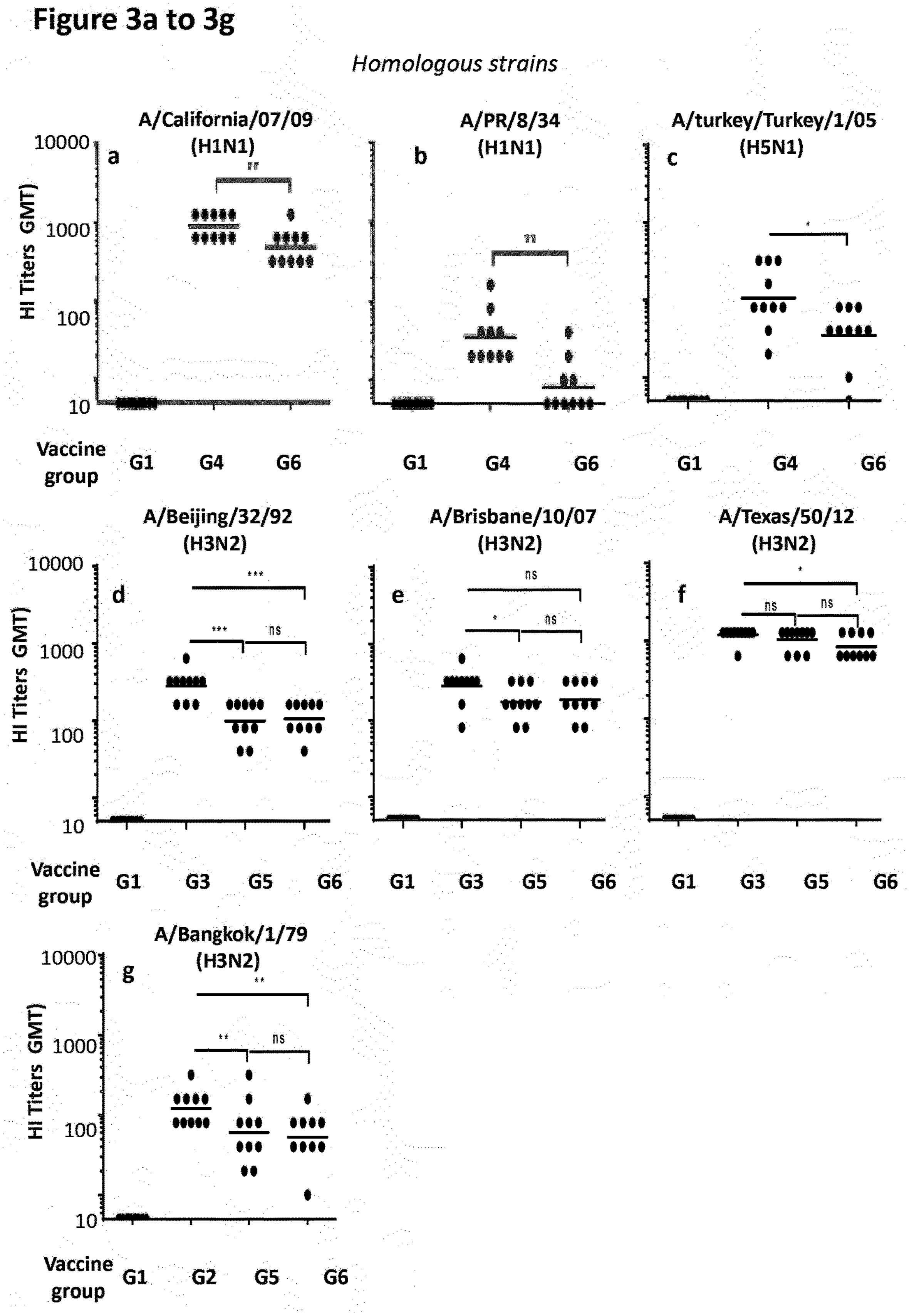
Figures 3H, 3I, 3J, 3K, 3L:
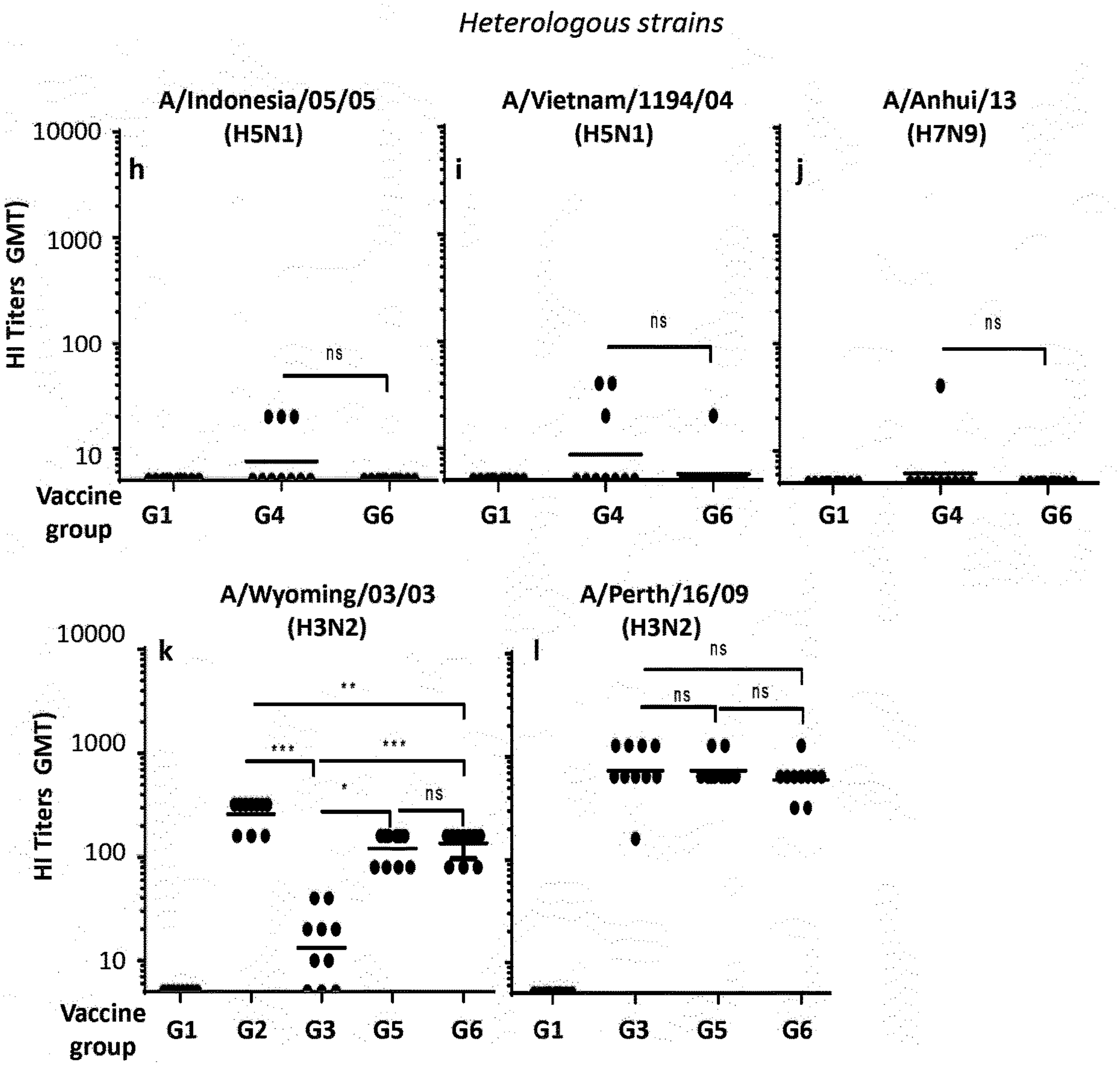

FIG. 3: Comparative immunogenicity of multivalent SAM(HA)/LNP candidate vaccines. Mice (n=10) were immunized i.m. on day 0 and day 21 with PBS [group 1] and combinations of SAM(H3-Biltho)+SAM(H3-Bang)+SAM(H3-Fuj) [group2]; SAM(H3-Beij)+SAM(H3-Bris)+SAM(H3-Tex) [group 3]; SAM(H1-Cal)+SAM(H1-PR8)+SAM(H5-turkey)+SAM (H7-Shan) [group 4]; SAM(H3-Biltho)+SAM(H3-Bang)+SAM(H3-Fuj)+SAM(H3-Beij)+SAM(H3-Bris)+SAM(H3-Tex) [group 5] and SAM(H3-Biltho)+SAM(H3-Bang)+SAM(H3-Fuj)+SAM(H3-Beij)+SAM(H3-Bris)+SAM(H3-Tex)+SAM(H1-Cal)+SAM(H1-PR8)+SAM(H5-turkey)+SAM (H7-Shan) [group 6] Sera samples were collected 2 weeks after second immunization. Sera samples were analyzed for HA-specific HI titres with homologous (a to g) and heterologous (h to l) influenza virus antigens. Statistical analyses were performed using the Mann-Whitney U test. *P<0.05 P<0.01, *P<0.001, ns; not significant).

Figures 4A, 4B, 4C, 4D, 4E, 4F:
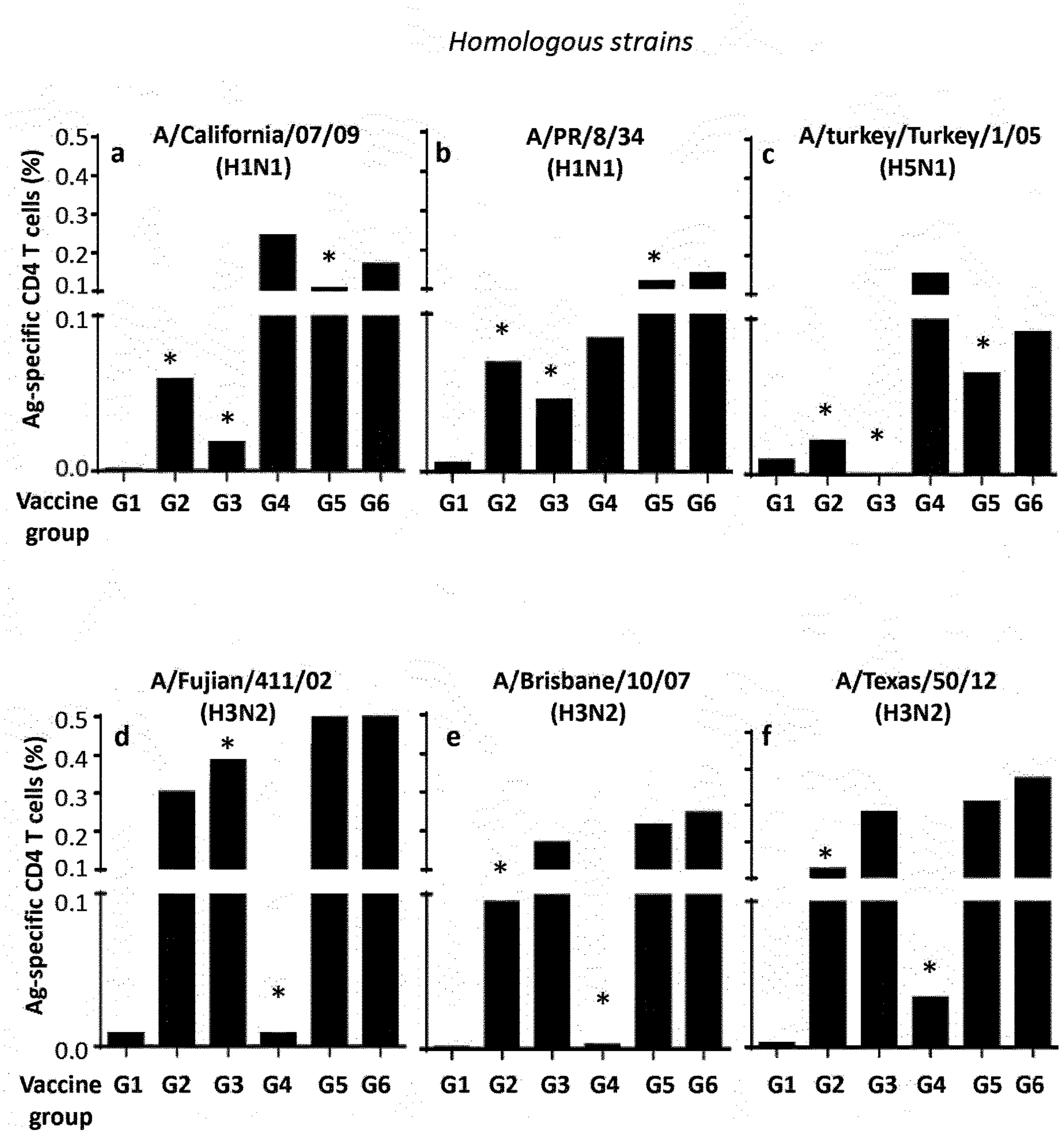
Figures 4G, 4H, 4I, 4J, 4K, 4L:
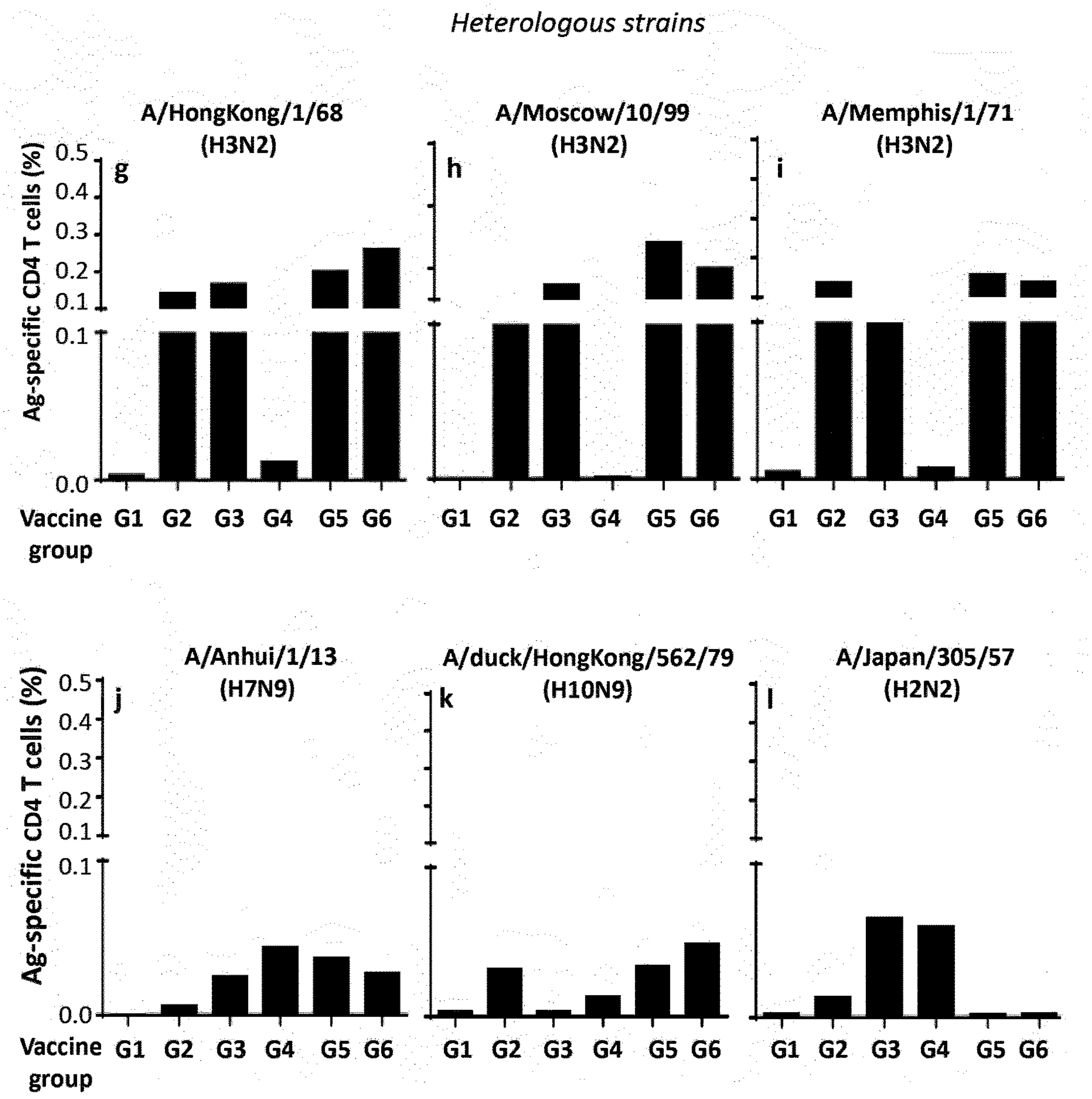

FIG. 4: Comparative $CD4^+$ T-cell responses induced by multivalent SAM(HA)/LNP candidate vaccines. Mice were immunized i.m. on day 0 and day 21 with PBS [group 1] and combinations of SAM(H3-Biltho)+SAM(H3-Bang)+SAM(H3-Fuj) [group 2]; SAM(H3-Beij)+SAM(H3-Bris)+SAM(H3-Tex) [group 3]; SAM(H1-Cal)+SAM(H1-PR8)+SAM(H5-turkey)+SAM (H7-Shan) [group 4]; SAM(H3-Biltho)+SAM(H3-Bang)+SAM(H3-Fuj)+SAM(H3-Beij)+SAM(H3-Bris)+SAM(H3-Tex) [group 5] and SAM(H3-Biltho)+SAM(H3-Bang)+SAM(H3-Fuj)+SAM(H3-Beij)+SAM(H3-Bris)+SAM(H3-Tex)+SAM(H1-Cal)+SAM(H1-PR8)+SAM(H5-turkey)+SAM (H7-Shan) [group 6]. Splenocytes (n=6) were stimulated in-vitro with HA peptide pools (d to f and i), and recombinant HA proteins (a to c, g, h and j to l). $CD4^+$ T-cell mediated homologous (a to f) and heterologous (g to l) responses were analyzed for cytokine production by flow cytometry. The bars represent the cumulative frequency of $CD4^+$ T cells producing cytokines.

Figure 5:
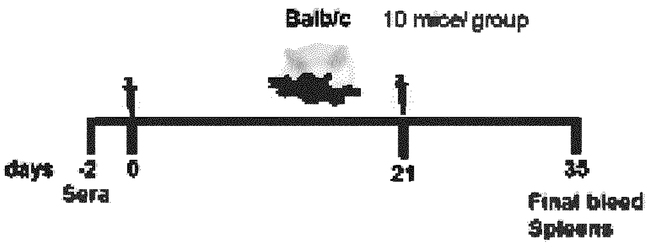

FIG. 5: a schematic diagram showing the immunization schedule used for Example 5.

Figure 6:
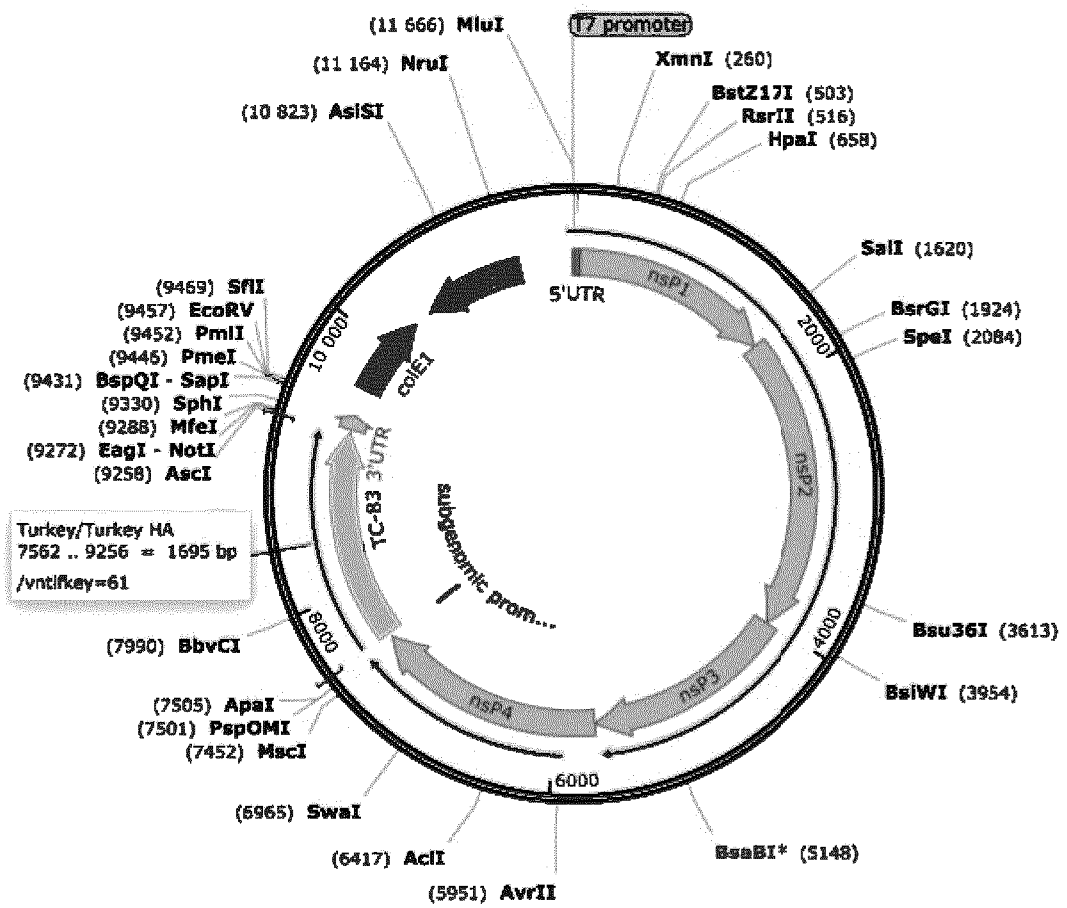

FIG. 6: a graphical map of the TC83 vector containing an insert of H5 HA A/turkey/turkey at positions 7562-9256.

Figure 7:
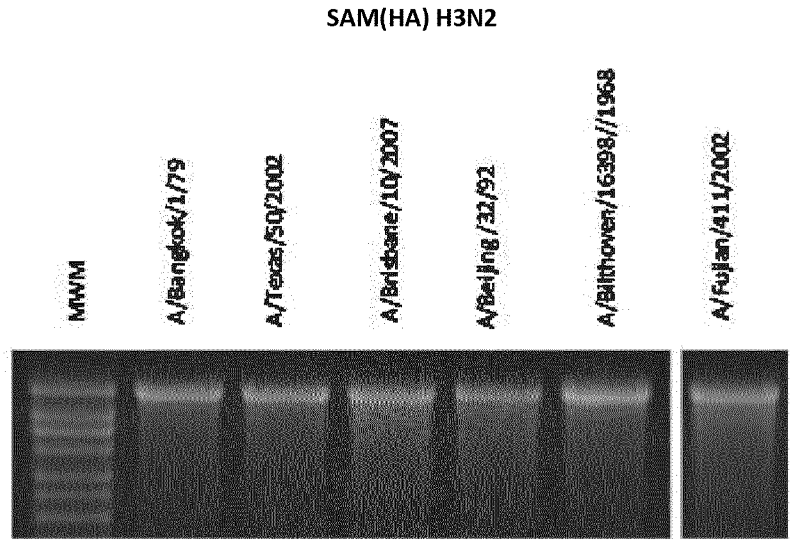
Figure 7:
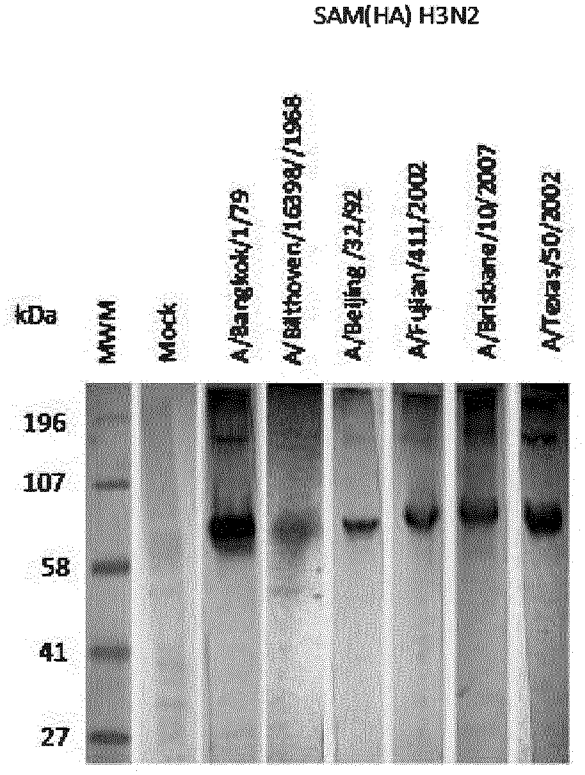

FIG. 7: RNA quality and confirmation of HA H3 gene expression. (A) the SAM vectors encoding the H3 antigen were analyzed on a denaturing agarose gel. (B) SAM vectors encoding H3 antigens were transiently infected into BHK cells and cell lysates were subjected to SDS-PAGE (sodium dodecyl sulfate polyacrylamide gel electrophoresis) and finally blotted to nitrocellulose membranes. H3 expression was visualized by Western blotting using H3-specific polyclonal antibodies.

DETAILED DESCRIPTION OF THE INVENTION

In the present study, by applying fully synthetic novel self-amplifying mRNA (SAM) vaccine technology, multivalent vaccine candidates were developed and immunogenicity tested in a Balb/c mice model. Vaccines were made comprising cocktails of two or more SAM vectors expressing full-length HAs from H3N2, H1N1, H5N1 and H7N9 subtypes either in monocistronic or bicistronic form and were encapsulated in lipid-nano particles (LNPs). It was demonstrated that in mice, SAM(H1), SAM(H5), SAM(H5-H1) or SAM(H1)+SAM(H5) induced $CD4^+$ or $CD8^+$ T-cell mediated heterologous responses, 3 weeks after the second immunization. However, this comparison of monocistronic and bicistronic SAM vectors suggested that combinations of two different influenza antigens in a single SAM vector is not as effective in boosting functional antibody responses as monocistronic SAM vectors. Cocktails of 3, 4, 6 or 10 monocistronic SAM(HA) vectors were prepared and were able to induce detectable cross-reactive B and T-cell responses in mice. Hence, for the first time, the inventors have shown a SAM(HA) multivalent vaccine that is able to induce broadly protective immune responses in Balb/c mice, against homologous and heterologous influenza viruses.

Self Replicating RNA Molecule

Immunogenic compositions of the invention comprise self replicating RNA molecules, each self replicating RNA molecule encoding a polypeptide comprising an antigen.

Self-replicating RNA molecules are well known in the art and can be produced by using replication elements derived from, e.g. alphaviruses, and substituting the structural viral proteins with a nucleotide sequence encoding a protein of interest. A self-replicating RNA molecule is typically a +-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded antigen (i.e. an influenza virus antigen), or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells.

One suitable system for achieving self-replication in this manner is to use an alphavirus-based replicon. These replicons are +-stranded (positive sense-stranded) RNAs which lead to translation of a replicase (or replicase-transcriptase) after delivery to a cell. The replicase is translated as a polyprotein which auto-cleaves to provide a replication complex which creates genomic-strand copies of the +-strand delivered RNA. These negative (−)-stranded transcripts can themselves be transcribed to give further copies of the +-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons, see the following reference: WO2005/113782, the context of which is incorporated by reference.

In one embodiment, each self-replicating RNA molecule described herein encodes (i) a RNA-dependent RNA polymerase which can transcribe RNA from the self-replicating RNA molecule and (ii) a polypeptide comprising an antigen from influenza virus. The polymerase can be an alphavirus replicase e.g. comprising one or more of alphavirus proteins nsP1, nsP2, nsP3 and nsP4.

Whereas natural alphavirus genomes encode structural virion proteins in addition to the non-structural replicase polyprotein, in certain embodiments, the self-replicating RNA molecules do not encode alphavirus structural proteins. Thus, the self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the present disclosure and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. The first (5') open reading frame encodes a replicase; the second (3') open reading frame encodes a polypeptide comprising an antigen from influenza virus. In some embodiments the RNA may have additional (e.g. downstream) open reading frames e.g. to encode further antigens or to encode accessory polypeptides.

In certain embodiments, the self-replicating RNA molecule disclosed herein has a 5' cap (e.g. a 7-methylguanosine). This cap can enhance in vivo translation of the RNA. In some embodiments the 5' sequence of the self-replicating RNA molecule must be selected to ensure compatibility with the encoded replicase.

A self-replicating RNA molecule may have a 3' poly-A tail. It may also include a poly-A polymerase recognition sequence (e.g. AAUAAA) near its 3' end.

Self-replicating RNA molecules can have various lengths but they are typically 5000-25000 nucleotides long. Self-replicating RNA molecules will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The self-replicating RNA can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the self-replicating RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

A self-replicating RNA can include (in addition to any 5' cap structure) one or more nucleotides having a modified nucleobase. A RNA used with the invention ideally includes only phosphodiester linkages between nucleosides, but in some embodiments it can contain phosphoramidate, phosphorothioate, and/or methylphosphonate linkages.

The self-replicating RNA molecule may encode a single heterologous polypeptide antigen (i.e. an antigen from influenza virus) or, optionally, two or more heterologous polypeptide antigens linked together in a way that each of the sequences retains its identity (e.g., linked in series) when expressed as an amino acid sequence. The heterologous polypeptides generated from the self-replicating RNA may then be produced as a fusion polypeptide or engineered in such a manner to result in separate polypeptide or peptide sequences. Self-replicating RNA molecules that encode a single heterologous polypeptide antigen may be termed "monocistronic" as described herein. Self-replicating RNA molecules that encode more than one, such as two separate heterologous polypeptide antigens, may be termed "multicistronic" or "bicistronic" respectively. Preferably, the self-replicating RNA molecules according to the invention are monocistronic.

The self-replicating RNA molecules described herein may be engineered to express multiple nucleotide sequences, from two or more open reading frames, thereby allowing co-expression of proteins, such as one, two or more influenza virus antigens, together with cytokines or other immunomodulators, which can enhance the generation of an immune response. Alternatively or in addition, the influenza virus antigen, e.g. an HA antigen, is the only antigen from influenza virus in each self-replicating RNA molecule.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self-replicating RNA molecule that encodes an antigen from influenza virus. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode an antigen from influenza virus can also be tested for the ability to induce humoral immune responses, as evidenced, for example, by induction of B cell production of antibodies specific for an influenza virus antigen of interest. These assays can be conducted using, for example, peripheral B lymphocytes from immunized individuals. Such assay methods are known to those of skill in the art. Other assays that can be used to characterize the self-replicating RNA molecules can involve detecting expression of the encoded influenza virus antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

In some embodiments, the self-replicating RNA molecule comprises a sequence that encodes (i) a RNA-dependent RNA polymerase which can transcribe RNA from the self-replicating RNA molecule and (ii) a polypeptide comprising an antigen from influenza virus. The polymerase can be an alphavirus replicase e.g. comprising one or more of alphavirus proteins nsP1, nsP2, nsP3 and nsP4.

In certain embodiments, immunogenic compositions according to the invention comprise self-replicating molecules wherein each self-replicating RNA molecule comprises a sequence that encodes (i) an alphavirus replicase which can transcribe RNA from the self-replicating RNA molecule and (ii) a polypeptide comprising hemagglutinin (HA) or an immunogenic fragment or variant thereof. Preferably, the polypeptide comprising HA or an immunogenic fragment or variant thereof is the only heterologous polypeptide encoded in the self-replicating RNA molecule. Typically, the HA or immunogenic fragment or variant thereof is the only antigen from influenza virus in the self-replicating RNA molecule.

For example, the self-replicating RNA molecules may comprise an RNA sequence encoded by the DNA sequence of SEQ ID NO: 2 or a DNA sequence that is at least 70%, at least 75%, at least 80%, at least 85%, at least 90%, at least 95%, at least 96%, at least 97%, at least 98%, or at least 99% identical to SEQ ID NO:2. In a particular embodiment, the self-replicating RNA molecules comprise an RNA sequence encoded by a DNA sequence at least 90% identical to SEQ ID NO:2. In some embodiments, the self replicating RNA molecules comprise an RNA sequence encoded by a fragment of a full-length sequence of SEQ ID NO:2 wherein the fragment comprises a contiguous stretch of the nucleic acid sequence of the full-length sequence up to 1, 2, 3, 4, 5, 6, 7, 8, 9, 10, 15, 20, 25, or 30 nucleic acids shorter than full-length sequence. In a specific embodiment, the self-relicating RNA molecules comprises an RNA sequence encoded by a fragment of SEQ ID NO:2 wherein the fragment comprises a contiguous stretch of the nucleic acid sequence of the full-length but up to nucleic acids shorter than full-length sequence.

Immunogenic compositions as disclosed herein may comprise self-replicating molecules that each comprise an RNA sequence encoded by a DNA sequence that is at least 90% identical to SEQ ID NO:2, wherein the antigen from influenza virus encoded by each self-relicating RNA molecule is HA or an immunogenic fragment or variant thereof and wherein HA or the immunogenic fragment or variant thereof is the only antigen from influenza virus in each self-replicating RNA molecule. In such embodiments, the HA may be from the same subtype of influenza virus (intrasubtypic) or from a different subtype of influenza (heterosubtypic) for each self-replicating RNA molecule.

Polypeptide Comprising an Antigen from Influenza Virus

The self-relicating RNA molecules of the invention encode a polypeptide comprising an antigen from influenza virus. In certain embodiments, the antigen encoded is a wild type influenza virus polypeptide sequence, or is a fragment or variant thereof.

A "variant" of a polypeptide antigen sequence includes amino acid sequences having one or more amino acid substitutions, insertions and/or deletions when compared to the reference sequence. The variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to any one of SEQ ID NOs: 4, 6, 8, 10, 12, 14, 16, 18, 20 or 22. Alternatively, or in addition, a fragment of a polypeptide antigen may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 19, or more amino acids which is identical to a contiguous amino acid sequence of the full-length polypeptide.

A fragment of a polypeptide may comprise N- and/or C-terminal deletions when compared to a full-length polypeptide, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence. It may be specified that the deletions are of consecutive amino acids.

As used herein, the term "antigen" refers to a molecule containing one or more epitopes (e.g., linear, conformational or both) that will stimulate a host's immune system to make a humoral and/or cellular antigen-specific immunological response (i.e. an immune response which specifically recognizes an antigen polypeptide). An "epitope" is that portion of an antigen that determines its immunological specificity.

Influenza viruses that infect humans can be classified into 3 types: A, B and C. A-type influenza viruses can be further classified into different subtypes, based on their HA (18 subtypes; H1, H2, H3, H4, H5, H6, H7, H8, H9, H10, H11, H12, H13, H14, H15, H16, H17 and H18) and NA proteins (11 subtypes, N1, N2, N3, N4, N5, N6, N7, N8, N9, N10 and N11). Influenza A viruses can be further broken down into different strains. B-type influenza viruses currently do not display different HA subtypes, but influenza B virus strains do fall into two distinct lineages. These lineages emerged in the late 1980s and have HAs which can be antigenically and/or genetically distinguished from each other. Current circulating influenza B virus strains belong to one of two lineages: B/Victoria or B/Yamagata. An internationally accepted naming convention for influenza viruses was accepted by WHO in 1979 and published in February 1980 in the Bulletin of the World Health Organization, 58(4):585-591(1980)("A revision of the system of nomenclature for influenza viruses: A WHO memorandum"). This approach uses a number of components in the naming system, including the antigenic type (A, B or C), geographical origin, year of isolation and strain number. Currently, influenza A(H1N1), A(H3N2) and one or two B strains are included in each year's influenza vaccine.

In the sense of the present invention, the term "influenza subtypes" is to be understood as A-type influenza virus strains having a given H subtype or a given N subtype, and the terms "different subtype" refer to influenza virus strains which do not share the same H subtype or the same N subtype. "Intrasubtypic" refers to the strains within the same influenza subtype, for example strains of a H1, H2, H3 etc HA subtype. "Heterosubtypic" refers to strains from different influenza subtypes, for example strains from the H1 subtype versus strains from the H3 subtype.

Influenza A viruses evolve and undergo antigenic variability continuously. A lack of effective proofreading by the viral RNA polymerase leads to a high rate of transcription errors that can result in amino-acid substitutions in surface glycoproteins, such as HA and NA proteins. This is termed "antigenic drift". The segmented viral genome allows for a second type of antigenic variation. If two influenza viruses simultaneously infect a host cell, genetic reassortment, called "antigenic shift" may generate a novel virus with new surface or internal proteins. These antigenic changes, both 'drifts' and 'shifts' are unpredictable and may have a dramatic impact from an immunological point of view as they eventually lead to the emergence of new influenza virus strains and that enable the virus to escape the immune system causing the well known, almost annual, epidemics. Both of these genetic modifications have caused new viral variants responsible for pandemic in humans.

The self-replicating RNA molecules of the present invention may encode an influenza antigen from any type (A-type, B-type, C-type) and any subtype (H1 to H18 and N1 to N11) of influenza viruses, or immunogenic fragments or variants thereof. By way of example, the self-replicating RNA molecules as described herein may encode a polypeptide encoding an antigen from influenza virus wherein the antigen from influenza virus comprises the polypeptide sequence of any one of SEQ ID NOs: 4, 6, 8, 10, 12, 14, 16, 18, 20 or 22 or an immunogenic fragment or variant thereof. In a specific embodiment, the antigen from influenza virus comprises the sequence of any one of SEQ ID NOs: 4, 6, 8, 10, 12, 14, 16, 18, 20 or 22. Alternatively, the antigen from influenza virus comprises or consists of a variant with an amino acid sequence at least 90% identical to the sequence of any one of SEQ ID NOs: 4, 6, 8, 10, 12, 14, 16, 18, 20 or 22. Alternatively or in addition, the antigen from influenza virus comprises or consists of an immunogenic fragment comprising a deletion of up to 20 amino acids from the N-terminus, the C-terminus, or both the N-terminus and C-terminus of the full-length sequence of any one of SEQ ID NOs: 4, 6, 8, 10, 12, 14, 16, 18, 20 or 22.

Suitably, the influenza virus antigen encoded by a self-replicating RNA molecule according to the invention is from a pandemic strain. By pandemic strain, is meant a new influenza virus against which the large majority of the human population has no immunity. Throughout the document "a pandemic strain" will refer to an influenza virus strain being associated with or with the potential to be associated with an outbreak of pandemic influenza disease, such as pandemic Influenza A-type virus strains. A strain with the potential to be associated with a pandemic outbreak may comprise a strain (e.g. an animal influenza virus strain) that has infected humans and that is not a circulating seasonal strain of influenza in humans (e.g. not a strain of influenza A(H1N1) or A(H3N2) or B strains of either Victoria or Yamagata lineage). Pandemic strains associated with a pandemic outbreak or with the potential to be associated with a pandemic will be known to those skilled in the art and are identified by the WHO according to internationally recognised criteria (see "Pandemic influenza preparedness and response" A WHO Guidance document, 2009, IBSN 9789241547680).

Suitable pandemic strains are, H1, H2, H5, H6, H7 or H9 subtype influenza A virus strains, e.g. H5N1, H5N3, H2N2, H6N1, H9N2, H7N7, H2N2, H7N1, H7N9 and H1N1. Within the H5 subtype, a virus may fall into different clades. Other suitable pandemic strains in human are H7N3, H10N7 and H5N2. Alternatively, the influenza virus antigen may be from a circulating seasonal strain, i.e. a non-pandemic strain.

In certain embodiments, the antigen from influenza virus is hemagglutinin (HA) or neuraminidase (NA) or any other antigen such as Matrix protein 2 (M2), Matrix protein 1 (M1), nucleoprotein (NP), PB1 or PB2 or an immunogenic fragment or variant thereof. Preferably, the antigen is HA or an immunogenic fragment or variant thereof.

Polypeptides according to the invention may comprise, in addition to the antigen from influenza virus, one or more heterologous amino acid sequences (e.g. another antigen sequence, another signal sequence, a detectable tag, or the like). For example, the polypeptide herein may be a fusion protein.

Nucleic Acid and its Preparation

Disclosed herein are nucleic acid molecules, such as DNA or RNA, comprising a sequence which encodes a polypeptide comprising an antigen from influenza virus. In the immunogenic compositions according to the invention, the self-replicating RNA molecules comprise such sequences in RNA form. Also disclosed herein, is nucleic acid in the form of self-relicating RNA molecules, with or without heterologous sequence encoding a polypeptide comprising an antigen from influenza virus.

Nucleic acid may be prepared in many ways, e.g. by chemical synthesis in whole or in part, by digesting longer nucleic acids using nucleases (e.g. restriction enzymes), by joining shorter nucleic acids or nucleotides (e.g. using ligases or polymerases), from genomic or cDNA libraries etc. For example, cDNA templates encoding a polypeptide comprising an antigen from influenza virus may be prepared. Such cDNA templates may be created and propagated in plasmid form in bacteria or created synthetically (for example by gene synthesis and/or polymerase chain-reaction (PCR) engineering methods). RNA sequences encoding polypeptides of the invention may be prepared for example, by in vitro transcription (IVT), which can use a DNA-dependent RNA polymerase (such as the bacteriophage T7, T3 or SP6 RNA polymerases) to transcribe RNA from the cDNA template.

The term "nucleic acid" in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the nucleic acid of the disclosure includes mRNA, self-replicating RNA, DNA, cDNA, recombinant nucleic acids, branched nucleic acids, plasmids, vectors, etc. Where the nucleic acid takes the form of RNA, it may or may not have a 5' cap.

The nucleic acids herein comprise a sequence which encodes a polypeptide comprising an antigen from influenza virus. Typically, the nucleic acids of the invention will be in recombinant form, i.e. a form which does not occur in nature. For example, the nucleic acid may comprise one or more heterologous nucleic acid sequences (e.g. a sequence encoding another antigen and/or a control sequence such as a promoter or an internal ribosome entry site) in addition to the sequence encoding an antigen from influenza virus. The nucleic acid may be part of a vector i.e. part of a nucleic acid construct designed for transduction/transfection of one or more cell types. Vectors may be, for example, "expression vectors" which are designed for expression of a nucleotide sequence in a host cell, or "viral vectors" which are designed to result in the production of a recombinant virus or virus-like particle.

The nucleic acid encoding the polypeptides described above may be codon optimized. By "codon optimized" is intended modification with respect to codon usage that may increase translation efficacy and/or half-life of the nucleic acid. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O] N), which may further increases translation efficacy.

The nucleic acids may comprise one or more nucleotide analogs or modified nucleotides. As used herein, "nucleotide analog" or "modified nucleotide" refers to a nucleotide that contains one or more chemical modifications (e.g., substitutions) in or on the nitrogenous base of the nucleoside (e.g. cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate. The preparation of nucleotides and modified nucleotides and nucleosides are well-known in the art, see the following references: U.S. Pat. Nos. 4,373,071, 4,458,066, 4,500,707, 4,668,777, 4,973,679, 5,047,524, 5,132,418, 5,153,319, 5,262,530, 5,700,642. Many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), mIA (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6-isopentenyladenosine); io6A (N6-(cis-hydroxyisopentenyl) adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-0-ribosyladenosine (phosphate)); I (inosine); mil (1-methylinosine); m'Im (I,2'-0-dimethylinosine); m3C (3-methylcytidine); Cm (2T-0-methylcytidine); s2C (2-thiocytidine); ac4C (N4-acetylcytidine); 5FC (5-formylcytidine); m5Cm (5,2-O-dimethylcytidine); ac4Cm (N4acetyl2TOmethylcytidine); k2C (lysidine); mIG (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-0-trimethylguanosine); Gr(p) (2'-0-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethy 1 aminomethyl-2-L-Omethyl uridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-0-dimethyladenosine); rn62Am (N6,N6,0-2-trimethyladenosine); m2'7G (N2,7-dimethylguanosine); m2'2'7G (N2,N2,7-trimethylguanosine); m3Um (3,2T-0-dimethyluridine); m5D (5-methyldihydrouridine); F5Cm (5-formyl-2'-O-methylcytidine); mlGm (I,2'-0-dimethylguanosine); m'Am (1,2-O-dimethyl adenosine) irinomethyluridine); tm5s2U (S-taurinomethyl-2-thiouridine)); iniG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(Ci-Ce)-alkyluracil, 5-methyluracil, 5-(C2-C6)-alkenyluracil, 5-(C2-Ce)-alkynyluracil, 5-(hydroxymethyl)uracil, 5-chlorouracil, 5-fluorouracil, 5-bromouracil, 5-hydroxycytosine, 5-(C1-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-0-methyl-U. Many of these modified nucleobases and their corresponding ribonucleosides are available from commercial suppliers.

Immunogenic and Pharmaceutical Compositions

Immunogenic compositions according the invention comprise self-replicating RNA molecules that encode polypeptides comprising an antigen from influenza virus. Such compositions may be a vaccine, in particular an RNA based vaccine.

Immunogenic compositions according to the invention comprise a first self-replicating RNA molecule encoding a polypeptide comprising a first antigen and a second self-replicating RNA molecule encoding a polypeptide comprising a second antigen. In certain embodiments, the immunogenic composition according to the invention comprises or contains further self-replicating molecules, such as 3, 4, 5, 6, 7, 8, 9 or 10 self-replicating RNA molecules. In particular, the immunogenic composition may comprise a third self-replicating RNA molecule encoding a polypeptide comprising a third antigen from influenza virus and optionally a fourth self-replicating RNA molecule encoding a polypeptide comprising a fourth antigen from influenza virus. Yet further self-replicating RNA molecules may be present in the immunogenic composition of the invention, for example:

- a $5^{th}$ self-replicating RNA molecule encoding a polypeptide comprising a $5^{th}$ antigen from influenza virus and optionally
- a 6th self-replicating RNA molecule encoding a polypeptide comprising a 6th antigen from influenza virus and optionally
- a 7th self-replicating RNA molecule encoding a polypeptide comprising a 7th antigen from influenza virus and optionally
- an 8th self-replicating RNA molecule encoding a polypeptide comprising an 8th antigen from influenza virus and optionally
- a 9th self-replicating RNA molecule encoding a polypeptide comprising a 9th antigen from influenza virus and optionally
- a 10th self-replicating RNA molecule encoding a polypeptide comprising a 10th antigen from influenza virus.

In these embodiments, the first, second, third and/or optional subsequent antigens from influenza virus are all from different strains of influenza virus. In some embodiments, the antigen in each self-replicating RNA molecule may be from a different subtype of influenza virus as compared to the remaining antigen/s (e.g. for HA; H1, H2, H3, H5, H7, H9 etc). In certain embodiments, the immunogenic compositions with 2, 3, 4, 5, 6, 7, 8, 9 or 10 self-replicating molecules contain only these self-replicating RNA molecules.

Typically, the immunogenic composition comprises or contains up to 10 self-replicating RNA molecules, such as from 2 to 10 self-replicating RNA molecules, from 2 to 8 self-replicating RNA molecules, from 3 to 7 self-replicating molecules, from 3 to 6 self-replicating RNA molecules or from 4 to 6 self-replicating RNA molecules, wherein each self-replicating RNA molecule encodes a polypeptide comprising an antigen from influenza virus and wherein each antigen is from a different strain of influenza virus. In a particular embodiment, the immunogenic composition according to the invention contains from 3 to 10 self-replicating RNA molecules.

In one embodiment, the first antigen and/or second antigen and/or optional subsequent antigens in the immunogenic compositions of the invention is hemagglutin (HA). Typically, the HA antigen may be derived from an influenza virus of a past or present seasonal or pandemic strain. For example, HA may be selected from seasonal strains of type H1 or H3, or pandemic strains of type H1, H2, H5, H6, H7, H9 or H10, such as H5 or H7. In one embodiment, hemagglutinin is the only antigen from influenza virus in the immunogenic composition.

In certain embodiments, the immunogenic composition comprises a first and/or second antigen that is HA from influenza virus H1. In other embodiments, the immunogenic composition comprises a first and/or second antigen that is HA from influenza virus H3. In a further embodiment, the first antigen is from influenza virus H1 and the second antigen is from influenza virus H3. In particular, the H1 influenza virus strain may be from A/H1N1 and the H3 influenza virus strain may be an A/H3N2 strain.

Other combinations of antigens from influenza virus are envisaged. E.g. for an immunogenic composition according to the invention which comprises two self-replicating molecules, the first and second antigens may be HA derived from the following hemagglutinin strain types respectively: H1+H1, H3+H3, H1+H3, H5+H7, H5+H5 or H7+H7. For an immunogenic composition according to the invention which comprises three self-replicating molecules, the first, second and third antigens may be derived from the following hemagglutinin strain types respectively: H1+H1+H1, H1+H1+H3, H1+H3+H3, H3+H3+H3, H1+H3+H5, H3+H3+H5, H3+H3+H7 or H1+H5+H7. For an immunogenic composition according to the invention which comprises four self-replicating molecules, the first, second, third and further antigens may be HA derived from the following strain types respectively: H1+H1+H3+H3, H1+H3+H3+H3, H1+H3+H3+H5, H1+H3+H5+H7 or H3+H3+H3+H3.

In any of these embodiment comprising two, three or four self replicating molecules, the HA antigens may be derived from a A/H1N1 strain. In addition, the HA antigens may be derived from a A/H3N2 strain.

Hence, in one embodiment, an immunogenic composition of the invention comprises (i) a first self-replicating RNA molecule encoding a polypeptide comprising a first antigen and (ii) a second self-replicating RNA molecule encoding a polypeptide comprising a second antigen, wherein:

- the first and second antigens are both from influenza virus but the first antigen is from a different strain of influenza virus to the second antigen,
- the first and second antigens are hemagglutinin or an immunogenic fragment or variant thereof,
- the first and second antigens are from strains of influenza virus with a different geographical origin and/or year of isolation.

In a further embodiment, an immunogenic composition of the invention comprises (i) a first self-replicating RNA molecule encoding a polypeptide comprising a first antigen and (ii) a second self-replicating RNA molecule encoding a polypeptide comprising a second antigen, wherein:

- the first and second antigens are both from influenza virus but the first antigen is from a different strain of influenza virus to the second antigen,
- the first and second antigen is hemagglutinin or an immunogenic fragment or variant thereof and the first and second antigens are from influenza viruses with a different hemagglutinin subtype.

In a further embodiment, an immunogenic composition of the invention comprises (i) a first self-replicating RNA molecule encoding a polypeptide comprising a first antigen and (ii) a second self-replicating RNA molecule encoding a polypeptide comprising a second antigen, wherein:

the first and second antigens are both from influenza virus but the first antigen is from a different strain of influenza virus to the second antigen, the first and second antigen is hemagglutinin or an immunogenic fragment or variant thereof and the first antigen is from a seasonal influenza virus (e.g. a H1N1, H3N2, B/Victoria or B/Yamagata strain) and the second antigen is from a pandemic influenza virus strain.

In a further embodiment, an immunogenic composition of the invention comprises (i) a first self-replicating RNA molecule encoding a polypeptide comprising a first antigen (ii) a second self-replicating RNA molecule encoding a polypeptide comprising a second antigen, and (iii) a third self-replicating RNA molecule encoding a polypeptide comprising a third antigen, wherein:

the first, second and third antigens are both from influenza virus but the first, second and third antigens are all from different strains of influenza virus, the first, second and third antigens are hemagglutinin or an immunogenic fragment or variant thereof and the first, second and third antigens are all from influenza viruses in the same hemagglutinin subtype but from viruses with a different geographical origin and/or year of isolation.

In a further embodiment, an immunogenic composition of the invention comprises (i) a first self-replicating RNA molecule encoding a polypeptide comprising a first antigen (ii) a second self-replicating RNA molecule encoding a polypeptide comprising a second antigen, and (iii) a third self-replicating RNA molecule encoding a polypeptide comprising a third antigen, wherein:

the first, second and third antigens are both from influenza virus but the first, second and third antigens are all from different strains of influenza virus, the first, second and third antigens are hemagglutinin or an immunogenic fragment or variant thereof and the first and second antigens are from past or present seasonal influenza viruses and the third antigen is from a pandemic influenza virus.

In one embodiment, the immunogenic composition may comprise multiple self-replicating RNA molecules, where each self-replicating RNA molecule encodes a polypeptide comprising an HA antigen from influenza virus H3. For example, the composition may comprise 2, 3, 4, 5, 6, 7, 8, 9 or 10 self-replicating RNA molecules encoding a polypeptide comprising an HA antigen from influenza virus H3.

In some such embodiments, the HA antigens are selected from strains of the influenza H3N2 subtype. For example, in one embodiment, HA antigens are selected from potential pandemic and seasonal strains of the influenza H3N2 subtypes. These strains of the H3N2 subtype may be selected on the basis of the following criteria: 1) major glycosylation sites, 2) important seasonal and pandemic vaccine strains, and 3) cell adapted strains only.

In one embodiment, the immunogenic composition comprises multiple self-replicating RNA molecules, where each self-replicating RNA molecule encodes a polypeptide comprising an HA antigen from a different strain of the H3N2 influenza virus.

In one embodiment, the immunogenic composition comprises three self-replicating RNA molecules, wherein: (i) a first self-replicating RNA molecule encodes a polypeptide comprising a first antigen from A/Bilthoven/16398/1968 (EPI362379), (ii) a second self-replicating RNA molecule encodes a polypeptide comprising a second antigen from A/Bangkok/1/79 (EPI367158), (iii) a third self-replicating RNA molecule encodes a polypeptide comprising a third antigen from A/Fujian/411/2002 (EPI362915).

In another embodiment, the immunogenic composition comprises three self-replicating RNA molecules, wherein: (i) a first self-replicating RNA molecule encodes a polypeptide comprising a first antigen from A/Beijing/32/92 (EPI365898), (ii) a second self-replicating RNA molecule encodes a polypeptide comprising a second antigen from A/Brisbane/10/2007 (EPI362338), and (iii) a third self-replicating RNA molecule encodes a polypeptide comprising a third antigen from A/Texas/50/2012 (EPI398417).

In one preferred embodiment, the immunogenic composition comprises six self-replicating RNA molecules, wherein: (i) a first self-replicating RNA molecule encodes a polypeptide comprising a first antigen from A/Bilthoven/16398/1968 (EPI362379), (ii) a second self-replicating RNA molecule encodes a polypeptide comprising a second antigen from A/Bangkok/1/79 (EPI367158), (iii) a third self-replicating RNA molecule encodes a polypeptide comprising a third antigen from A/Beijing/32/92 (EPI365898), (iv) a fourth self-replicating RNA molecule encodes a polypeptide comprising a fourth antigen from A/Fujian/411/2002 (EPI362915), (v) a fifth self-replicating RNA molecule encodes a polypeptide comprising a fifth antigen from A/Brisbane/10/2007 (EPI362338), and (vi) a sixth self-replicating RNA molecule encodes a polypeptide comprising a sixth antigen from A/Texas/50/2012 (EPI398417). Sequence information for full length genes encoding for influenza HA proteins was obtained from the Global Initiative on Sharing All Influenza Data Epiflu database (www.gisaid.org).

The immunogenic composition of all of these embodiments may also include one or more further self-replicating RNA molecules, where one or more further self-replicating RNA molecules encode a polypeptide comprising an HA antigen from influenza virus H1, H5 and/or H7. In such embodiments, the self-replicating RNA molecules may encode polypeptides comprising an HA antigen from two different influenza H1 viruses. Additionally, the self-replicating RNA molecules may encode a polypeptide comprising an HA antigen from influenena subtype H5. The self-replicating RNA molecules may also encode a polypeptide comprising an HA antigen from influenena subtype H7.

In one embodiment, the immunogenic composition comprises ten self-replicating RNA molecules, wherein: (i) a first self-replicating RNA molecule encodes a polypeptide comprising a first antigen from A/Bilthoven/16398/1968 (EPI362379), (ii) a second self-replicating RNA molecule encodes a polypeptide comprising a second antigen from A/Bangkok/1/79 (EPI367158), (iii) a third self-replicating RNA molecule encodes a polypeptide comprising a third antigen from A/Beijing/32/92 (EPI365898), (iv) a fourth self-replicating RNA molecule encodes a polypeptide comprising a fourth antigen from A/Fujian/411/2002 (EPI362915), (v) a fifth self-replicating RNA molecule encodes a polypeptide comprising a fifth antigen from A/Brisbane/10/2007 (EPI362338), and (vi) a sixth self-replicating RNA molecule encodes a polypeptide comprising a sixth antigen from A/Texas/50/2012 (EPI398417), (vii) a seventh self-replicating RNA molecule encodes a polypeptide comprising a seventh antigen from A/California/07/2009 (H1N1), (viii) an eighth self-replicating RNA molecule encodes a polypeptide comprising a eighth antigen from A/PR/8/1934 (H1N1), (ix) a ninth self-replicating RNA molecule encodes a polypeptide comprising a ninth antigen from A/turkey/Turkey/5/2005 (H5N1), and (x) a tenth self-replicating RNA molecule encodes a polypeptide comprising a tenth antigen from A/Shanghai/1/3013 (H7N9).

The immunogenic composition may comprise a viral or a non-viral delivery system. The delivery system (also referred to herein as a delivery vehicle) may have adjuvant effects which enhance the immunogenicity of the encoded antigen from influenza virus. For example, the self-replicating RNA molecules may be encapsulated in liposomes, non-toxic biodegradable polymeric microparticles or viral replicon particles (VRPs), or complexed with particles of a cationic oil-in-water emulsion. In some embodiments, the nucleic acid-based vaccine comprises a cationic nano-emulsion (CNE) delivery system or a lipid nanoparticle (LNP) delivery system. In some embodiments, the nucleic acid-based vaccine comprises a non-viral delivery system, i.e., the nucleic acid-based vaccine is substantially free of viral capsid. Alternatively, the nucleic acid-based vaccine may comprise viral replicon particles. In other embodiments, the nucleic acid-based vaccine may comprise a naked nucleic acid, such as naked RNA (e.g. mRNA), but delivery via CNEs or LNPs is preferred.

In certain embodiments, the nucleic acid-based vaccine comprises a cationic nano-emulsion (CNE) delivery system. CNE delivery systems and methods for their preparation are described in the following reference: WO2012/006380. In a CNE delivery system, the nucleic acid molecule (e.g. RNA) which encodes the antigen is complexed with a particle of a cationic oil-in-water emulsion. Cationic oil-in-water emulsions can be used to deliver negatively charged molecules, such as an RNA molecule to cells. The emulsion particles comprise an oil core and a cationic lipid. The cationic lipid can interact with the negatively charged molecule thereby anchoring the molecule to the emulsion particles. Further details of useful CNEs can be found in the following references: WO2012/006380; WO2013/006834; and WO2013/006837 (the contents of each of which are incorporated herein in their entirety).

Thus, in certain embodiments, in immunogenic compositions according to the invention, the self-replicating RNA molecules encoding a polypeptide comprising an antigen from influenza virus are complexed with a particle of a cationic oil-in-water emulsion. The particles typically comprise an oil core (e.g. a plant oil or squalene) that is in liquid phase at 25° C., a cationic lipid (e.g. phospholipid) and, optionally, a surfactant (e.g. sorbitan trioleate, polysorbate 80); polyethylene glycol can also be included. In some embodiments, the CNE comprises squalene and a cationic lipid, such as 1,2-dioleoyloxy-3-(trimethylammonio)propane (DOTAP). In some preferred embodiments, the delivery system is a non-viral delivery system, such as CNE. This may be particularly effective in eliciting humoral and cellular immune responses. Advantages also include the absence of a limiting anti-vector immune response and a lack of risk of genomic integration.

In some embodiments, self-replicating RNA molecules according to the invention may be complexed with a submicron cationic oil-in-water emulsion. In some embodiments the cationic oil-in-water emulsion is characterized by an average particle size of from about 80 nm to 180 nm in diameter (or alternatively from about 80 to about 150 nm; from about 80 to 130 nm; or from about 100 nm). In some embodiments, the concentration of DOTAP in said emulsion, before RNA complexation, is at least about 2.5 mM, or from about 2.5 mM to about 8 mM. In a particular embodiment, the concentration of DOTAP in said emulsion is about 4 mg/ml (5.73 mM). The oil can be squalene or squalane.

In some embodiments, in immunogenic compositions of the invention self-relicating RNA molecules are complexed to a cationic oil-in-water emulsion comprising DOTAP, squalene, sorbitan trioleate and polysorbate 80 in citrate buffer. Cationic oil-in-water emulsions suitable for delivery of an RNA molecule encoding a polypeptide comprising an antigen from influenza virus may contain about 2 mg/ml to 7 mg/ml DOTAP; about 3 mg/ml to 6 mg/ml Span 85; about 3 mg/ml to 6 mg/ml Tween 80; and about 30 mg/ml to 50 mg/ml squalene. In certain embodiments, the cationic oil-in-water emulsion, before complexing with RNA, contains about 4.3% w/v squalene, 0.5% Tween 80, 0.5% SPAN85, and 4 mg/mL DOTAP.

Hence, in one embodiment, an immunogenic composition of the invention comprises (i) a first self-replicating RNA molecule encoding a polypeptide comprising a first antigen and (ii) a second self-replicating RNA molecule encoding a polypeptide comprising a second antigen, wherein:

the first and second antigens are both from influenza virus but the first antigen is from a different strain of influenza virus to the second antigen, the first and second antigens are hemagglutinin or an immunogenic fragment or variant thereof, the self-replicating RNA molecules are formulated in lipid nanoparticles (LNP).

Hence, in one embodiment, an immunogenic composition of the invention comprises (i) a first self-replicating RNA molecule encoding a polypeptide comprising a first antigen and (ii) a second self-replicating RNA molecule encoding a polypeptide comprising a second antigen, wherein:

the first and second antigens are both from influenza virus but the first antigen is from a different strain of influenza virus to the second antigen, the first and second antigens are hemagglutinin or an immunogenic fragment or variant thereof, the self-replicating RNA molecules are formulated in a cationic nanoemulsion (CNE).

Hence, in one embodiment, an immunogenic composition of the invention comprises (i) a first self-replicating RNA molecule encoding a polypeptide comprising a first antigen and (ii) a second self-replicating RNA molecule encoding a polypeptide comprising a second antigen, wherein:

the first and second antigens are both from influenza virus but the first antigen is from a different strain of influenza virus to the second antigen, the first and second antigens are hemagglutinin or an immunogenic fragment or variant thereof, the self-replicating RNA molecules are formulated in lipid nanoparticles (LNP) or a cationic nanoemulsion (CNE) and as well as encoding a polypeptide comprising an antigen from influenza virus, each self-replicating RNA molecule encodes a RNA-dependent RNA polymerase which can transcribe RNA from the self-replicating RNA molecule.

In a further embodiment, an immunogenic composition of the invention comprises (i) a first self-replicating RNA molecule encoding a polypeptide comprising a first antigen (ii) a second self-replicating RNA molecule encoding a polypeptide comprising a second antigen, and (iii) a third self-replicating RNA molecule encoding a polypeptide comprising a third antigen, wherein:

- the first, second and third antigens are both from influenza virus but the first, second and third antigens are all from different strains of influenza virus,
- the first, second and third antigens are hemagglutinin or an immunogenic fragment or variant thereof and
- the self-replicating RNA molecules are formulated in lipid nanoparticles (LNP) or a cationic nanoemulsion (CNE).

In a further embodiment, an immunogenic composition of the invention comprises (i) a first self-replicating RNA molecule encoding a polypeptide comprising a first antigen (ii) a second self-replicating RNA molecule encoding a polypeptide comprising a second antigen, and (iii) a third self-replicating RNA molecule encoding a polypeptide comprising a third antigen, wherein:

- the first, second and third antigens are both from influenza virus but the first, second and third antigens are all from different strains of influenza virus,
- the first, second and third antigens are hemagglutinin or an immunogenic fragment or variant thereof,
- the self-replicating RNA molecules are formulated in lipid nanoparticles (LNP) or a cationic nanoemulsion (CNE) and
- as well as encoding a polypeptide comprising an antigen from influenza virus, each self-replicating RNA molecule encodes a RNA-dependent RNA polymerase which can transcribe RNA from the self-replicating RNA molecule.

Also provided is a method of preparing an immunogenic composition according to the invention wherein the self-replicating RNA molecules are complexed to a cationic oil-in-water emulsion, the method comprising: (i) providing an oil-in-water emulsion as described herein; (ii) providing an aqueous solution comprising the self-replicating RNA molecules; and (iii) combining the aqueous solution of (ii) and the oil-in-water emulsion of (i), thereby preparing the immunogenic composition. If desired, the aqueous solution comprising the RNA molecule may be a buffer. The buffer may comprise one or more salt, buffer, saccharide, or polymer. In an preferred embodiment, the buffer comprises 560 mM sucrose, 20 mM NaCl, and 10 mM citrate, which can be mixed with a cationic oil in water emulsion described herein to produce a final aqueous phase that comprises 280 mM sucrose, 10 mM NaCl and 10 mM citrate.

Also provided is a method of preparing an immunogenic composition according to the invention wherein the self-replicating RNA molecules are encapsulated in a lipid nanoparticle (LNP), the method comprising: (i) providing at least one lipid which forms nanoparticles; (ii) providing an aqueous solution comprising the self-replicating RNA molecules; and (iii) combining the aqueous solution of (ii) and the at least one lipid of (i), thereby preparing the composition.

LNP delivery systems and non-toxic biodegradable polymeric microparticles, and methods for their preparation are described in the following references: WO2012/006376 (LNP and microparticle delivery systems); Geall et al. (2012) PNAS USA. September 4; 109(36): 14604-9 (LNP delivery system); and WO2012/006359 (microparticle delivery systems). LNPs are non-virion liposome particles in which a nucleic acid molecule (e.g. RNA) can be encapsulated. The particles can include some external RNA (e.g. on the surface of the particles), but at least half of the RNA (and ideally all of it) is encapsulated. Liposomal particles can, for example, be formed of a mixture of zwitterionic, cationic and anionic lipids which can be saturated or unsaturated, for example; DSPC (zwitterionic, saturated), DlinDMA (cationic, unsaturated), and/or DMG (anionic, saturated). In some embodiments, the LNP comprises neutral lipids, cationic lipids, cholesterol and polyethylene glycol (PEG) and forms nanoparticles that encompass the self-amplifying RNA. Preferred LNPs for use with the invention include an amphiphilic lipid (helper lipid(s)) which can form liposomes, optionally in combination with at least one cationic lipid (such as DOTAP, DSDMA, DODMA, DLinDMA, DLenDMA, etc.). Useful helper lipids include zwitterionic lipids, such as DPPC, DOPC, DSPC, dodecylphosphocholine, 1,2-dioleoyl-sn-glycero-3-phosphatidylethanolamine (DOPE), and 1,2-diphytanoyl-sn-glycero-3-phosphoethanolamine (DPyPE); sterols, such as cholesterol; and PEGylated lipids, such as PEG-DMPE (PEG-conjugated 1, 2-dimyristoyl-Sn-glycero-3-phosphoethanolamine-N-[methoxy (polyethylene glycol)]) or PEG-DMG (PEG-conjugated 1,2-Dimyristoyl-sn-glycerol, methoxypolyethylene Glycol). In some embodiments, useful PEGylated lipids may be PEG2K-DMPE (PEG-conjugated 1, 2-dimyristoyl-Sn-glycero-3-phosphoethanolamine-N-[methoxy (polyethylene glycol)-2000]) or PEG2K-DMG (PEG-conjugated 1,2-Dimyristoyl-sn-glycerol, methoxypolyethylene Glycol-2000). A mixture of DSPC, DlinDMA, PEG-DMG and cholesterol is particularly effective. Other useful LNPs are described in the following references: WO2012/006376; WO2012/030901; WO2012/031046; WO2012/031043; WO2012/006378; WO2011/076807; WO2013/033563; WO2013/006825; WO2014/136086; WO2015/095340; WO2015/095346; WO2016/037053. In some embodiments, the LNPs are RV01 liposomes, see the following references: WO2012/006376 and Geall et al. (2012) PNAS USA. September 4; 109(36): 14604-9. In an embodiment, the LNPs are RV01 liposomes wherein the cationic lipid is DLinDMA.

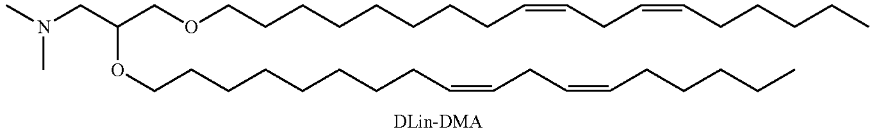 [SMILES: CCCCC/C=C\C/C=C\CCCCCCCCOCC(CN(C)C)OCCCCCCCC/C=C\C/C=C\CCCCC]

DLin-DMA

RV01

In some embodiments, the cationic lipids herein comprise the structure of Formula I:

Formula I

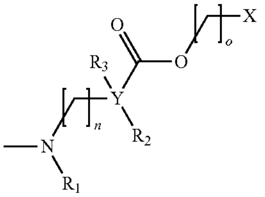

wherein n=an integer from 1 to 3 and (i) $R_1$ is $CH_3$, $R_2$ and $R_3$ are both H, and Y is C; or (ii) $R_1$ and $R_2$ are collectively $CH_2$—$CH_2$ and together with the nitrogen form a five-, six-, or seven-membered heterocycloalkyl, $R_3$ is $CH_3$, and Y is C; or (iii) $R_1$ is $CH_3$, $R_2$ and $R_3$ are both absent, and Y is O;

wherein o is 0 or 1;

wherein X is:

(i)

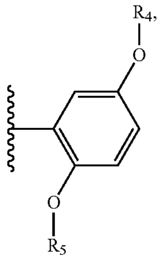

wherein $R_4$ and $R_5$ are independently a $C_{10-20}$ hydrocarbon chain having one or two cis alkene groups at either or both of the omega 6 and 9 positions; or (ii) —CH(—$R_6$)—$R_7$, wherein (1) $R_6$ is —$(CH_2)_p$—O—C(O)—$R_8$ or —$C_p$—$R_8$;

(2) $R_7$ is —$(CH_2)_{p'}$—O—C(O)—$R_8$' or —$C_{p'}$—$R_8$', (3) p and p' are independently 0, 1, 2, 3 or 4; and (4) $R_8$ and $R_{8'}$ are independently a (A) —$C_{8-20}$ hydrocarbon chain having one or two cis alkene groups at either or both of the omega 6 and 9 positions;

(B) —$C_{1-3}$—C(—O—$C_{6-12}$)—O—$C_{6-12}$ saturated or unsaturated hydrocarbon chain;

(C) —$C_{6-16}$ saturated hydrocarbon chain;

(D) —C(—$C_{6-16}$)—$C_{6-16}$ saturated or unsaturated hydrocarbon chain;

(E) —C[—C—O—C(O)—$C_{4-12}$]—C—O—C(O)—$C_{4-12}$ saturated or unsaturated hydrocarbon chain; and (F) —$C_{6-16}$ saturated or unsaturated hydrocarbon chain.

In an embodiment, $R_1$ is $CH_3$, $R_2$ and $R_3$ are both H, and Y is C. In some embodiments, $R_1$ and $R_2$ are collectively $CH_2$—$CH_2$ and together with the nitrogen form a five-, six-, or seven-membered heterocycloalkyl, $R_3$ is $CH_3$, and Y is C. In some embodiments, $R_1$ is $CH_3$, $R_2$ and $R_3$ are both absent, and Y is O.

In an embodiment, X is

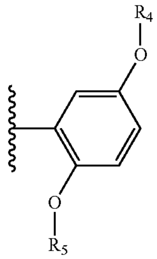

wherein $R_4$ and $R_5$ are independently a $C_{10-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is —$C_{1-3}$—C(—O—$C_{6-12}$)—O—$C_{6-12}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{6-16}$ saturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{6-16}$ saturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{6-16}$ saturated hydrocarbon chain; and $R_8$' is a —$C_6$-16 saturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{6-16}$ saturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{6-16}$ saturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; $R_8$ is a —$C_{6-16}$ saturated hydrocarbon chain; and $R_8$' is a —$C_6$-16 saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —($CH_2$)$_p$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —($CH_2$)$_p$—O—C(O)—$R_8$, $R_7$ is —($CH_2$)$_p$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —($CH_2$)$_p$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —($CH_2$)$_p$—O—C(O)—$R_8$, $R_7$ is —($CH_2$)$_p$—O—C(O)—$R_8$', p and p' are independently 0, 1, 2, 3 or 4; and $R_8$ is a —$C_{6-16}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —($CH_2$)$_p$—O—C(O)—$R_8$', p and p' are independently 0, 1, 2, 3 or 4; and $R_8$ is a —$C_{6-16}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —($CH_2$)$_p$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —($CH_2$)$_p$—O—C(O)—$R_8$, $R_7$—$C_{p'}$—$R_8$', p and p' are independently 0, 1, 2, 3 or 4; $R_8$ is —$C_{1-3}$—C(—O—$C_{6-12}$)—O—$C_{6-12}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —$C_{6-16}$ saturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —($CH_2$)$_p$—O—C(O)—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; $R_8$ is a —$C_{6-16}$ saturated hydrocarbon chain; and $R_8'$ is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C(—$C_{6-16}$)—$C_{6-16}$ saturated or unsaturated hydrocarbon chain; and $R_8'$ is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8'$ is a —$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$(CH_2)_p$—O—C(O)—$R_8$, $R_7$ is $C_{p'}$—$R_8'$, p and p' are independently 0, 1, 2, 3 or 4; and $R_8$ is a —$C_{6-16}$ saturated or unsaturated hydrocarbon chain; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —$C_{6-16}$ saturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$(CH_2)_p$—O—C(O)—$R_8$, $R_7$ is —$C_{p'}$—$R_8'$, p and p' are independently 0, 1, 2, 3 or 4; and $R_8$ is a —$C_{6-16}$ saturated or unsaturated hydrocarbon chain; and $R_8'$ is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_p$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8'$, p and p' are independently 0, 1, 2, 3 or 4; $R_8$ is a —$C_{8-20}$ hydrocarbon chain having one or two cis alkene groups at either or both of the omega 6 and 9 positions; and $R_8'$ is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is —$C_{1-3}$—C(—O—$C_{6-12}$)—O—$C_{6-12}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{6-16}$ saturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{6-16}$ saturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{6-16}$ saturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{6-16}$ saturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{6-16}$ saturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; $R_8$ is a —$C_{6-16}$ saturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_{p'}$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —$C_{6-16}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —$C_{6-16}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$(CH_2)_p$—O—C(O)—$R_8$', p and p' are independently 0, 1, 2, 3 or 4; and $R_8$ is a —$C_{6-16}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{8-20}$ hydrocarbon chain having one or two cis alkene groups at either or both of the omega 6 and 9 positions; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$—$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is —$C_{1-3}$—C(—O—$C_{6-12}$)—O—$C_{6-12}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$—$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$—$C_{p'}$—$R_8$', p and p' are independently 0, 1, 2, 3 or 4; $R_8$ is a —$C_{1-3}$—C(—O—$C_{6-12}$)—O—$C_{6-12}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; $R_8$ is a —$C_{6-16}$ saturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$C_p$—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$C_p$—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$C_p$—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$C_p$—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —C(—$C_{6-16}$)—$C_{6-16}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$—$C_{p'}$—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$—$C_{p'}$—$R_8$', p and p' are independently 0, 1, 2, 3 or 4; and $R_8$ is a —C[—C—O—C(O)—$C_{4-12}$]—C—O—C(O)—$C_{4-12}$ saturated or unsaturated hydrocarbon chain; and $R_8$' is a —$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —$C_{6-16}$ saturated or unsaturated hydrocarbon chain; and $R_8$' is a —$C_{8-20}$ hydrocarbon chain having one or two cis alkene groups at either or both of the omega 6 and 9 positions.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —$C_{6-16}$ saturated or unsaturated hydrocarbon chain; and $R_8$' is a —$C_{1-3}$—C(—O—$C_{6-12}$)—O—$C_{6-12}$ saturated or unsaturated hydrocarbon chain.

In an embodiment, X is —CH(—$R_6$)—$R_7$, $R_6$ is —$C_p$—$R_8$, $R_7$—$C_{p'}$—$R_8$', p and p' are independently 0, 1, 2, 3 or 4; and $R_8$ is a —$C_{6-16}$ saturated or unsaturated hydrocarbon chain; and $R_8$' is a —$C_{6-16}$ saturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —$C_{6-16}$ saturated or unsaturated hydrocarbon chain; and $R_8$' is a —C(—$C_{6-16}$)—$C_{6-16}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$'', p and p' are independently 0, 1, 2, 3 or 4; and $R_8$ is a —$C_{6-16}$ saturated or unsaturated hydrocarbon chain; and $R_8$' is a —C[—C—O—C(O)—$C_{4-12}$]—C—O—C(O)—$C_{4-12}$ saturated or unsaturated hydrocarbon chain.

In an embodiment, X is —CH(—$R_6$)—$R_7$, $R_6$ is —$C_p$—$R_8$, $R_7$ is —$C_{p'}$—$R_8$', p and p' are independently 0, 1, 2, 3 or 4; and $R_8$ is a —$C_{6-16}$ saturated or unsaturated hydrocarbon chain; and $R_8$' is a —$C_{6-16}$ saturated or unsaturated hydrocarbon chain.

In an embodiment, an exemplary cationic lipid is RV28 having the following structure: RV28
RV28
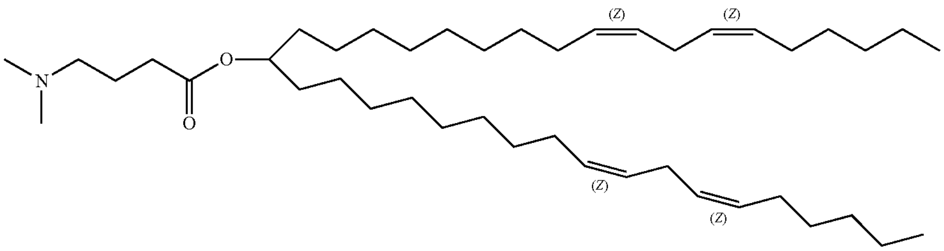
In an embodiment, an exemplary cationic lipid is RV31 having the following structure:
RV31
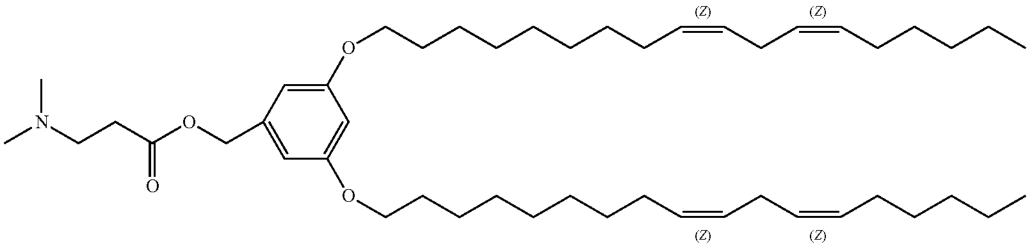
In an embodiment, an exemplary cationic lipid is RV33 having the following structure:
RV33
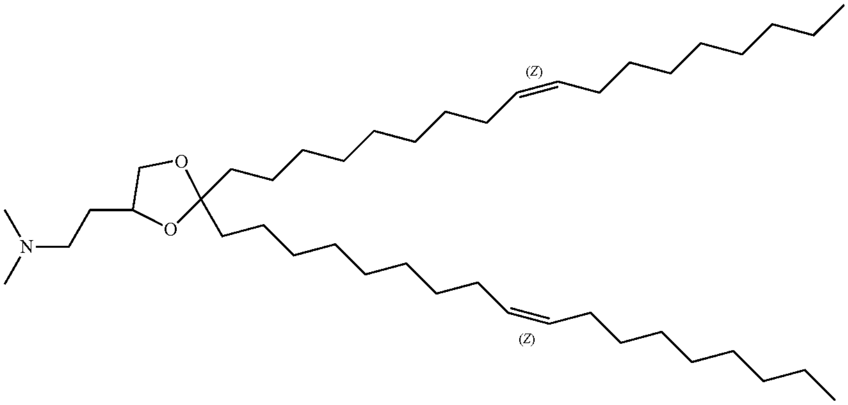

In an embodiment, an exemplary cationic lipid is RV37 having the following structure:
RV37
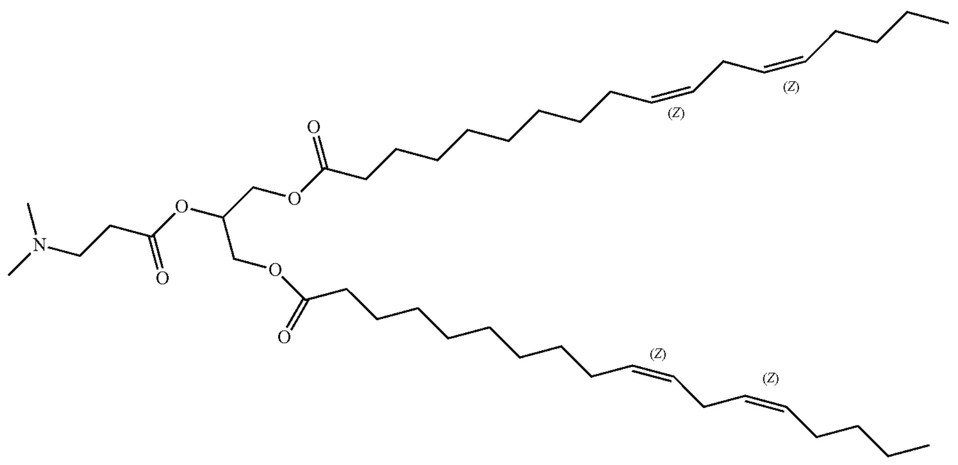
In an embodiment, the LNP comprises the cationic lipid RV39, i.e., 2,5-bis((9Z,12Z)-octadeca-9,12-dien-1-yloxy) benzyl 4-(dimethylamino)butanoate):
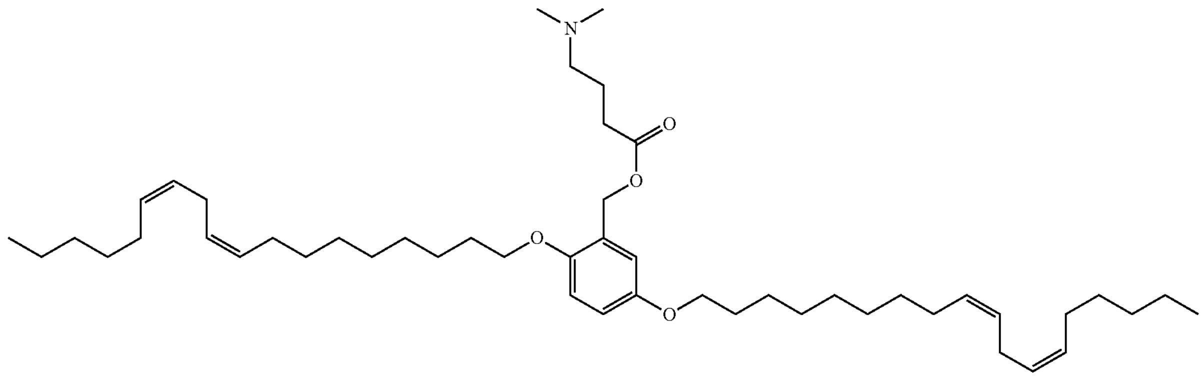 [SMILES: CCCCC/C=C\C/C=C\CCCCCCCCOc1ccc(OCCCCCCCC/C=C\C/C=C\CCCCC)c(COC(=O)CCCN(C)C)c1]
RV39 In an embodiment, an exemplary cationic lipid is RV42 having the following structure:
RV42
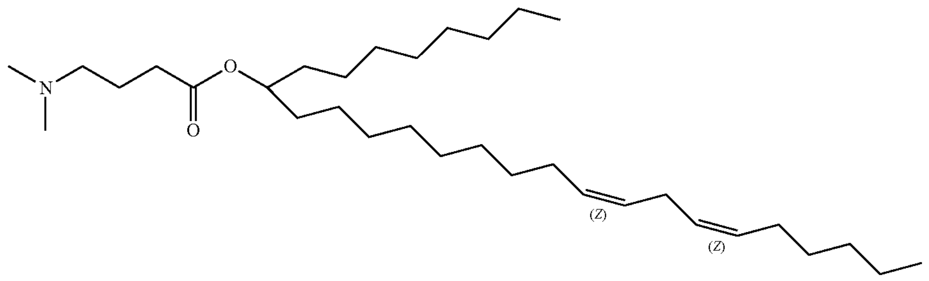

In an embodiment, an exemplary cationic lipid is RV44 having the following structure:
RV44
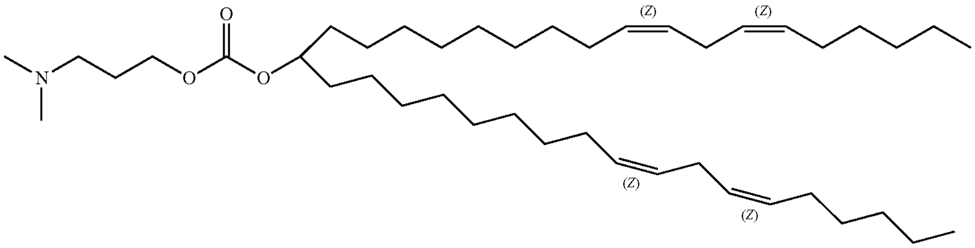
In an embodiment, an exemplary cationic lipid is RV73 having the following structure:
RV73
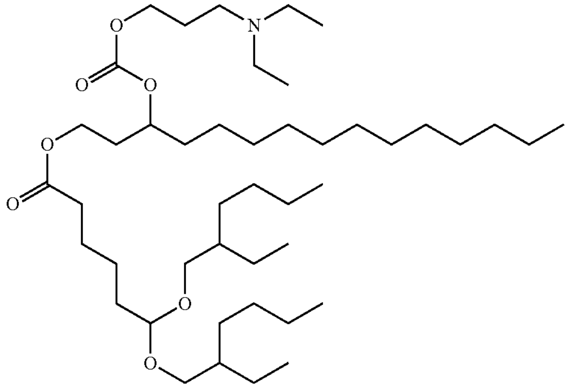
In an embodiment, an exemplary cationic lipid is RV75 having the following structure:
RV75
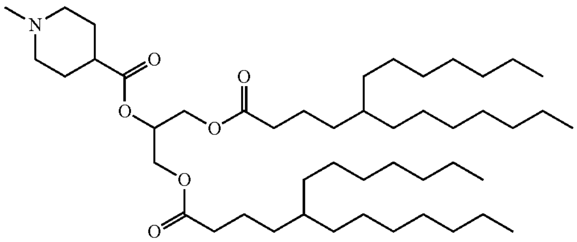
In an embodiment, an exemplary cationic lipid is RV81 having the following structure:
RV81
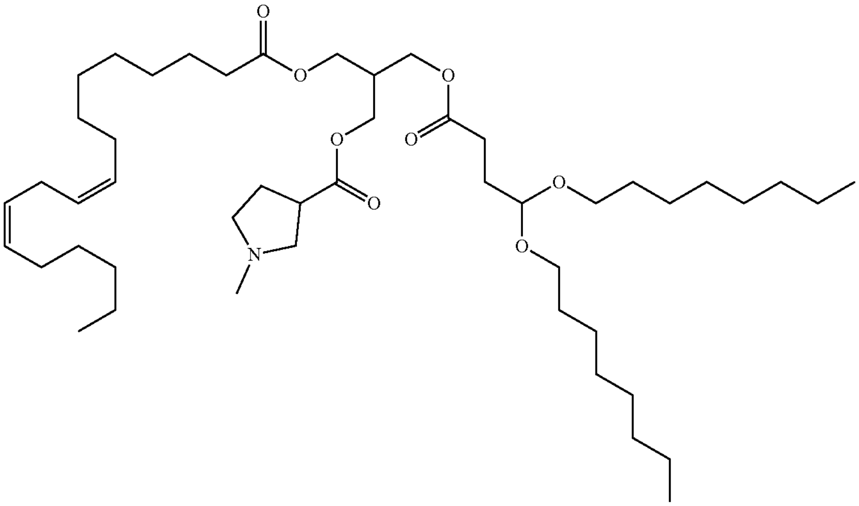

In an embodiment, an exemplary cationic lipid is RV84 having the following structure:
RV84
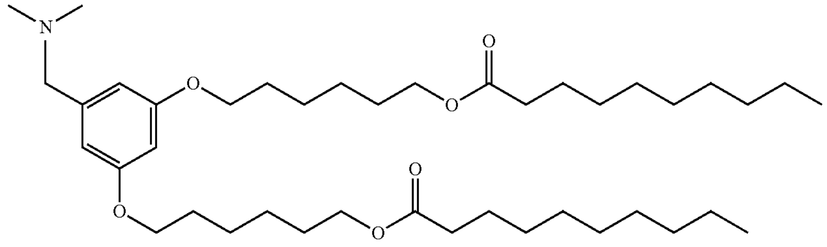
In an embodiment, an exemplary cationic lipid is RV85 having the following structure:
RV85
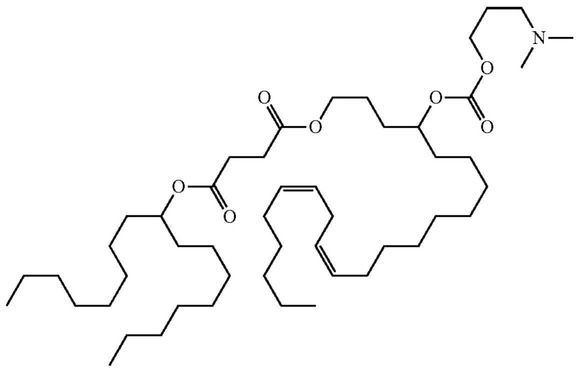
RV86
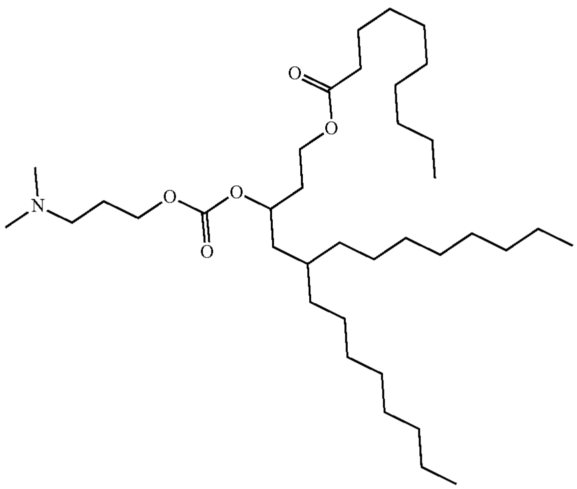
In an embodiment, an exemplary cationic lipid is RV86 having the following structure:
In an embodiment, an exemplary cationic lipid is RV88 having the following structure: RV88
RV88
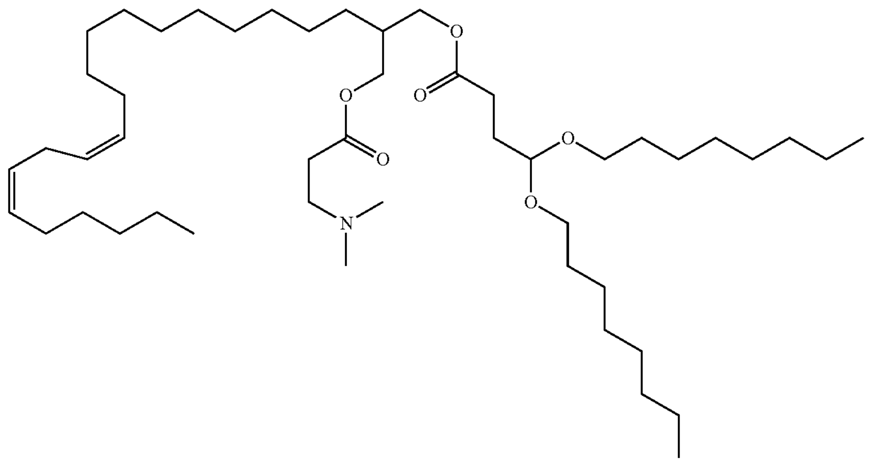

In an embodiment, an exemplary cationic lipid is RV91 having the following structure:
RV91
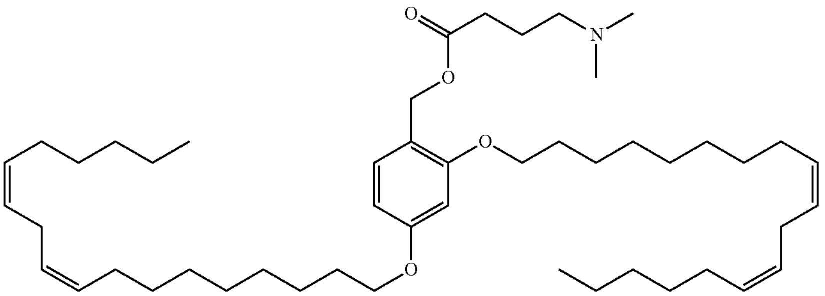
In an embodiment, an exemplary cationic lipid is RV92 having the following structure:
RV92
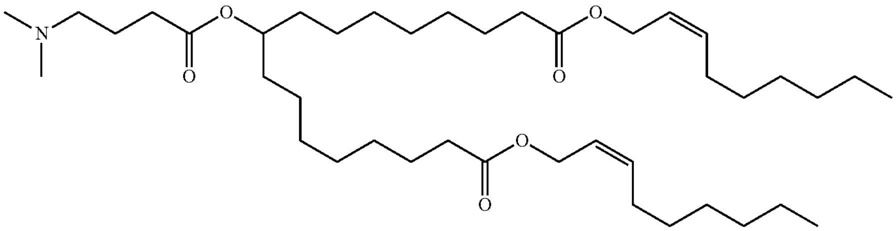
In an embodiment, an exemplary cationic lipid is RV93 having the following structure:
RV93
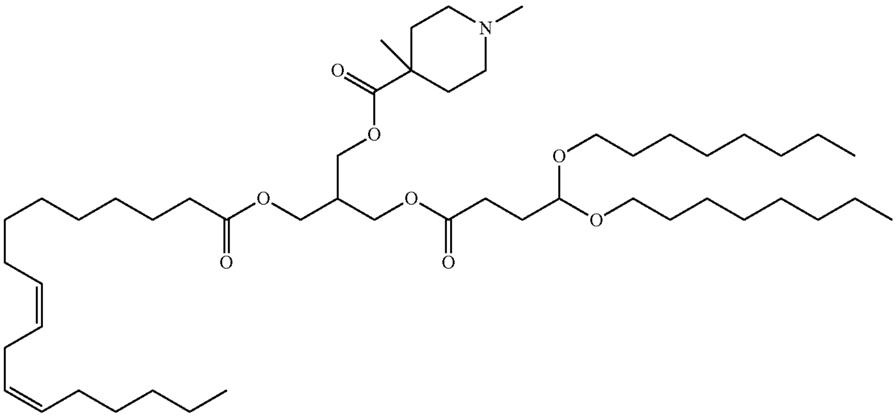

In an embodiment, an exemplary cationic lipid is 2-(5-((4-((1,4-dimethylpiperidine-4-carbonyl)oxy)hexadecyl)oxy)-5-oxopentyl)propane-1,3-diyl dioctanoate (RV94), having the following structure:
RV94
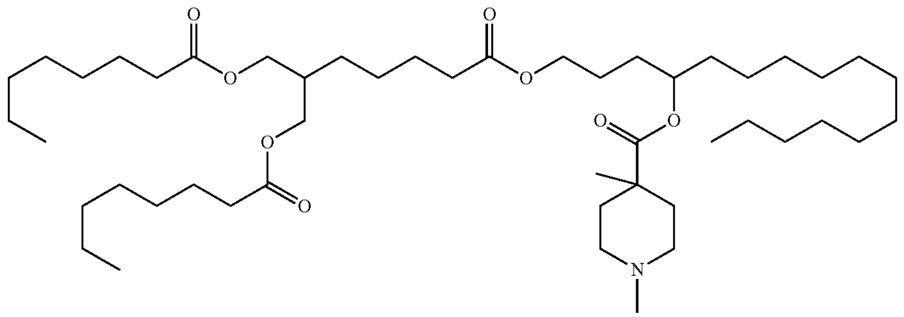
In an embodiment, an exemplary cationic lipid is RV95 having the following structure:
RV95
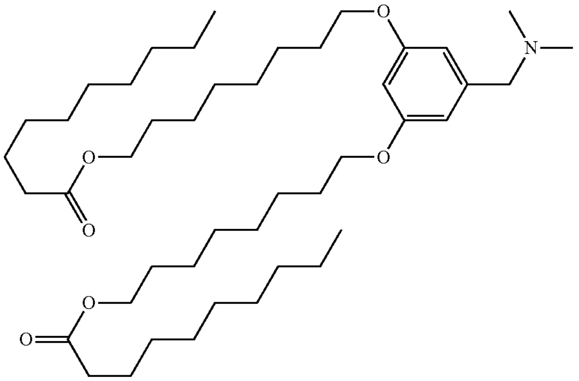
In an embodiment, an exemplary cationic lipid is RV96 having the following structure:
RV96
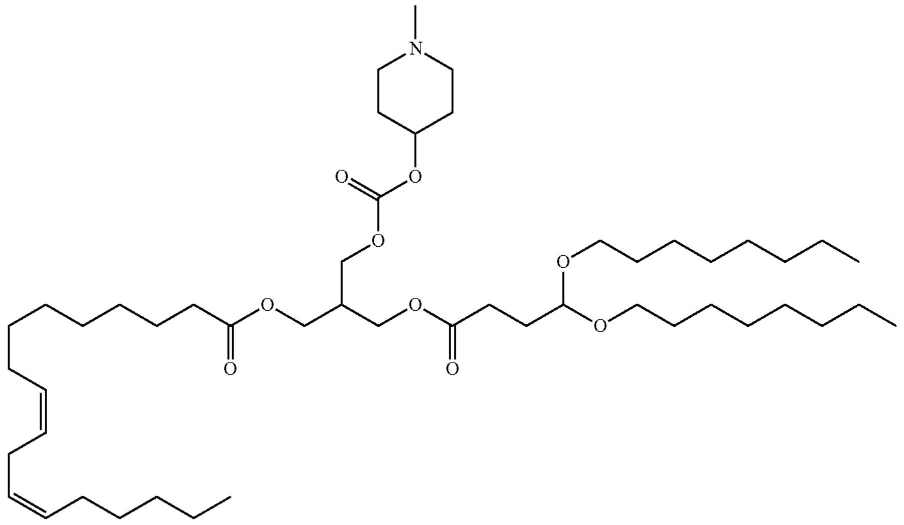

In an embodiment, an exemplary cationic lipid is RV97 having the following structure:
RV97
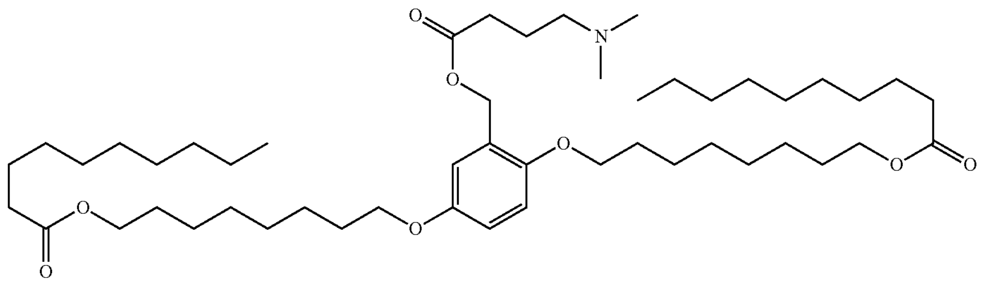
In an embodiment, an exemplary cationic lipid is RV99 having the following structure:
RV99
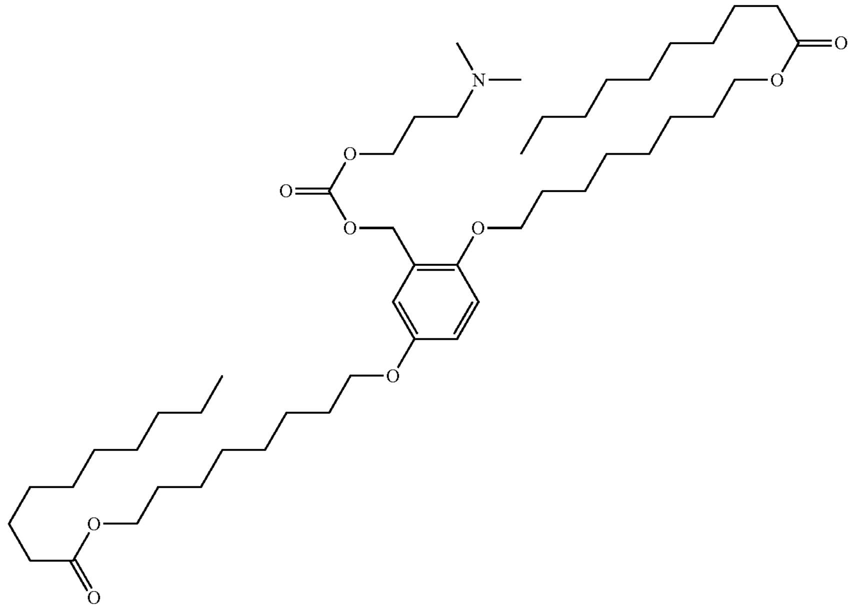

In an embodiment, an exemplary cationic lipid is RV101 having the following structure:

RV101

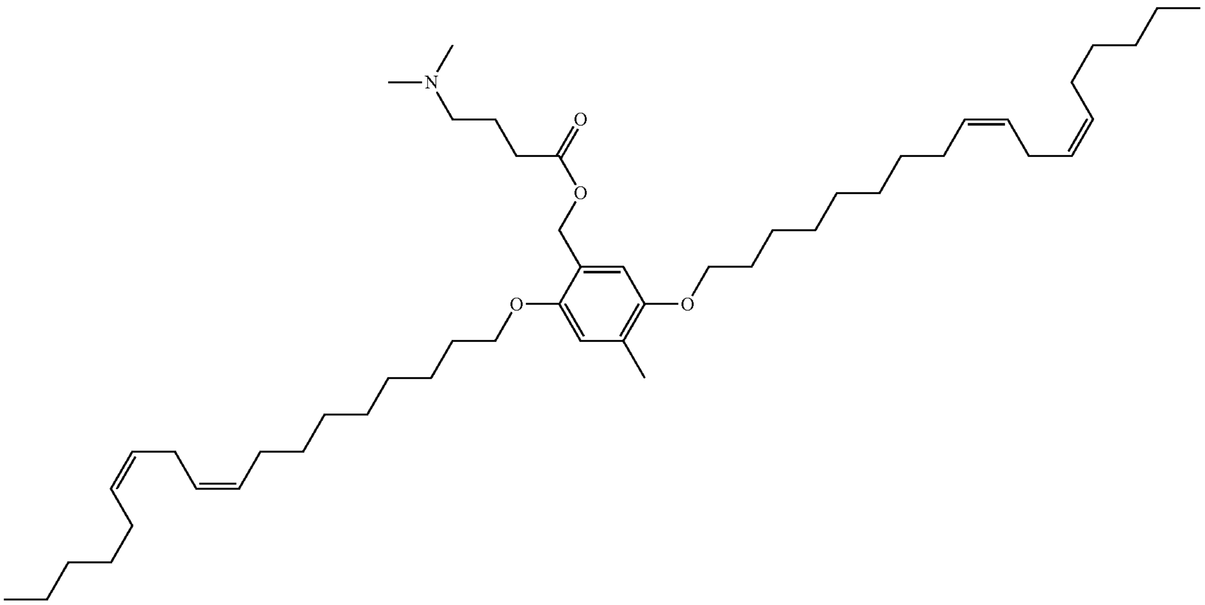

In an embodiment, the cationic lipid is selected from the group consisting of: RV28, RV31, RV33, RV37, RV39, RV42, RV44, RV73, RV75, RV81, RV84, RV85, RV86, RV88, RV91, RV92, RV93, RV94, RV95, RV96, RV97, RV99, and RV101. In an embodiment, the cationic lipid is selected from the group consisting of: RV39, RV88, and RV94.

Compositions and methods for the synthesis of compounds having Formula I and RV28, RV31, RV33, RV37, RV39, RV42, RV44, RV73, RV75, RV81, RV84, RV85, RV86, RV88, RV91, RV92, RV93, RV94, RV95, RV96, RV97, RV99, and RV101 can be found in PCT/US2014/070882 (publication number WO/2015/095340) and PCT/US2014/070891 (publication number WO/2015/095346), filed 17 Dec. 2014; as well as PCT/US2015/048535 (publication number WO/2016/037053), filed 4 Sep. 2015.

In some embodiments, the methods of manufacturing a non-viral delivery system comprising a liposome encapsulating an RNA comprise the following steps: (a) mixing (i) a first solution comprising a solvent, an ionizable cationic lipid, a zwitterionic lipid, a sterol, and a PEGylated lipid selected; and (ii) a second solution comprising water and the RNA; and (b) removing the solvent. The mixing may be carried out in a T-junction device, a microfluidic device, or the like, as described in WO2012031046 and/or PCT/IB2018/053850.

The immunogenic composition according to the invention may be a pharmaceutical composition e.g. a vaccine composition. Accordingly, the composition may also comprise a pharmaceutically acceptable carrier.

A "pharmaceutically acceptable carrier" includes any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The compositions may also contain a pharmaceutically acceptable diluent, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

Pharmaceutical compositions may include the immunogenic compositions, nucleic acid sequences, and/or polypeptide sequences described elsewhere herein in plain water (e.g. "w.f.i.") or in a buffer e.g. a phosphate buffer, a Tris buffer, a borate buffer, a succinate buffer, a histidine buffer, or a citrate buffer. Buffer salts will typically be included in the 5-20 mM range. Pharmaceutical compositions may have a pH between 5.0 and 9.5 e.g. between 6.0 and 8.0. Compositions may include sodium salts (e.g. sodium chloride) to give tonicity. A concentration of 10±2 mg/mL NaCl is typical, e.g. about 9 mg/mL. Compositions may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity. Pharmaceutical compositions may have an osmolality of between 200 mOsm/kg and 400 mOsm/kg, e.g. between 240-360 mOsm/kg, or between 290-310 mOsm/kg. Pharmaceutical compositions may include one or more preservatives, such as thiomersal or 2-phenoxyethanol. Mercury-free compositions are preferred, and preservative-free vaccines can be prepared. Pharmaceutical compositions may be aseptic or sterile. Pharmaceutical compositions may be non-pyrogenic e.g. containing <1 EU (endotoxin unit, a standard measure) per dose, and preferably <0.1 EU per dose. Pharmaceutical compositions may be gluten free. Pharmaceutical compositions may be prepared in unit dose form. In some embodiments a unit dose may have a volume of between 0.1-1.0 mL e.g. about 0.5 mL.

In some embodiments, the compositions disclosed herein are immunogenic composition that, when administered to a subject, induce a humoral and/or cellular antigen-specific immune response (i.e. an immune response which specifically recognizes a naturally occurring influenza virus antigen polypeptide). For example, an immunogenic composition may induce a memory T and/or B cell population relative to an untreated subject following influenza virus infection. In some embodiments, the subject is a vertebrate, such as a mammal e.g. a human or a veterinary mammal.

The immunogenic compositions of the invention can be formulated as vaccine compositions. The vaccine will comprise an immunologically effective amount of antigen. By "an immunologically effective amount" is intended that the administration of that amount to a subject, either in a single dose or as part of a series, is effective for inducing a measurable immune response against influenza virus in the subject. This amount varies depending upon the health and physical condition of the individual to be treated, age, the taxonomic group of individual to be treated (e.g. human, non-human primate, etc.), the capacity of the individual's immune system to synthesize antibodies, the degree of protection desired, the formulation of the composition or vaccine, the treating doctor's assessment of the medical situation, the severity of the disease, the potency of the compound administered, the mode of administration, and other relevant factors. It is expected that the amount will fall in a relatively broad range that can be determined through routine trials. Vaccines as disclosed herein may either be prophylactic (i.e. to prevent infection) or therapeutic (i.e. to treat infection), but will typically be prophylactic. In some embodiments, the vaccine compositions disclosed herein may induce an effective immune response against an influenza virus infection, i.e., a response sufficient for treatment or prevention of a influenza virus infection.

In some embodiments, the immunogenic composition of the invention further comprises an additional antigen. In some embodiments, the immunogenic composition is administered to a subject in combination with a further composition which comprises an additional antigen.

In a specific embodiment is provided a pharmaceutical composition (such as a vaccine composition) which comprises or consists of (i) from 3 to 10 self-replicating RNA molecules wherein each self-replicating RNA molecule encodes a polypeptide comprising an antigen from influenza virus, wherein each antigen is from a different strain of influenza virus to the other antigens and wherein the self-replicating RNA molecules are formulated in lipid nanoparticles (LNP) (iii) a pharmaceutical carrier, diluent and/or buffer and optionally (iii) an adjuvant.

For example, a vaccine composition is provided which comprises or consists of (i) from 3 to self-replicating RNA molecules formulated in lipid nanoparticles (LNP) and (ii) a pharmaceutical carrier, diluent and/or buffer, wherein:

- each self-replicating RNA molecule encodes a polypeptide comprising an antigen from influenza virus,
- each antigen is from a different strain of influenza virus to the other antigens and
- the LNP comprises a neutral lipid, a cationic lipid, cholesterol and polyethylene glycol (PEG) which form nanoparticles that encompass the self-replicating RNA. In certain embodiments, the neutral lipid is DSPC and the cationic lipid is DLinDMA.

An immunogenic composition of the present invention may also comprise, or be administered in conjunction with, one or more adjuvants (e.g. vaccine adjuvants). By adjuvant is intended that it is capable of increasing an immune response against an antigen compared to administration of said antigen alone. In some aspects, adjuvant compositions as disclosed herein further comprise one or more immunostimulants, for example, a saponin such as QS21.

Adjuvants which may be used in compositions of the invention include, but are not limited to: (A) Mineral-containing compositions, for example aluminum and calcium salts, such as aluminum phosphates. (B) Oil emulsions, for example squalene-in-water emulsions, such as MF59 or AS03. Complete Freund's adjuvant (CFA) and incomplete Freund's adjuvant (IF A) may also be used. (C) Saponin formulations. (D) Virosomes and virus-like particles (VLPs). (E) Bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. (F) Human immunomodulators, for example cytokines, such as interleukins, interferons, macrophage colony stimulating factor, and tumor necrosis factor. (G) Bioadhesives and mucoadhesives, such as esterified hyaluronic acid microspheres, cross-linked derivatives of poly(acrylic acid), polyvinyl alcohol, polyvinyl pyrollidone, polysaccharides and carboxymethylcellulose. (H) Microparticles, for example particles of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(a-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB). (I) Liposomes. (J) Polyoxyethylene ether and polyoxyethylene ester formulations. (K) Polyphosphazene (PCPP). (L) Muramyl peptides. (M) Imidazoquinolone compounds, for example Imiquamod and its homologues.

Combinations of one or more of the adjuvants identified above may also be used with the invention.

In a specific embodiment is provided a vaccine composition according to the invention Administration and Uses Methods of Use/Uses In some embodiments are provided methods for inducing an immune response against influenza virus infection in a subject in need thereof comprising a step of administering an immunologically effective amount of the immunogenic or pharmaceutical compositions as disclosed herein.

In some embodiments are provided the use of the compositions disclosed herein for inducing an immune response to an influenza virus antigen in a subject in need thereof. In some embodiments are provided the use of the compositions disclosed herein for inducing an immune response against an influenza virus infection in a subject. In some embodiments are provided use of the compositions as disclosed herein in the manufacture of a medicament that induces an immune response to a influenza virus infection in a subject.

By "subject" is intended a vertebrate, such as a mammal e.g. a human or a veterinary mammal. In some embodiments the subject is human. By "immune response" is intended a humoral and/or cellular antigen-specific immunological response (i.e. an immune response which specifically recognizes an antigen polypeptide) that can be demonstrated to neutralize influenza virus in vitro or control/reduce/eliminate infection virus infection in vivo. In some embodiments, the immune response is characterized by immunological memory against the influenza virus and/or an effective influenza virus-responsive memory T cell population.

In some embodiments, the compositions disclosed herein are for use in therapy or medicine. In a preferred embodiment, the therapy is a vaccine therapy. Preferably the therapy is a vaccine to prevent influenza virus infection. In some embodiments a composition disclosed herein is for use in preventing or treating influenza or for use in preventing or treating influenza virus infection in a subject in need thereof. In some embodiments, a composition disclosed herein is for use in inducing an immune response against a influenza virus infection in a subject in need thereof.

A composition described herein may be for use in preventing influenza virus infection by multiple different strains of influenza virus, or for inducing an immune response to an infection by any one of multiple different strains of influenza virus. For example, a composition may be for use in preventing or shortening influenza virus infection against two or more H1 and/or two or more H3 type strains of influenza virus. The composition may be for preventing or shortening influenza virus infection against both seasonal and pandemic strains of influenza virus. In some embodiments, the composition described herein may be for use in preventing influenza virus infection against homologous and/or heterologous strains of influenza virus. In one embodiment, the composition may be for use in preventing influenza virus infection against intrasubtypic and/or heterosubtypic strains of influenza virus.

Hence, in certain embodiments is provided an immunogenic or pharmaceutical composition as disclosed herein for use in preventing influenza virus infection against intrasubtypic strains of influenza virus.

In a specific embodiment, is provided a vaccine composition for use in preventing influenza virus infection against homologous and/or heterologous strains of influenza virus wherein the vaccine composition comprises (i) a first self-replicating RNA molecule encoding a polypeptide comprising a first antigen and (ii) a second self-replicating RNA molecule encoding a polypeptide comprising a second antigen, wherein:

- the first and second antigens are both from influenza virus but the first antigen is from a different strain of influenza virus to the second antigen,
- the first and second antigens are hemagglutinin or an immunogenic fragment or variant thereof and
- the self-replicating RNA molecules are formulated in lipid nanoparticles (LNP) or a cationic nanoemulsion (CNE).

In a specific embodiment is provided a vaccine composition for use in preventing influenza virus infection against homologous and/or heterologous strains of influenza virus wherein the vaccine composition comprises (i) a first self-replicating RNA molecule encoding a polypeptide comprising a first antigen and (ii) a second self-replicating RNA molecule encoding a polypeptide comprising a second antigen, wherein:

- the first and second antigens are both from influenza virus but the first antigen is from a different strain of influenza virus to the second antigen,
- the first and second antigens are hemagglutinin or an immunogenic fragment or variant thereof,
- the self-replicating RNA molecules are formulated in lipid nanoparticles (LNP) or a cationic nanoemulsion (CNE) and
- as well as encoding a polypeptide comprising an antigen from influenza virus, each self-replicating RNA molecule encodes a RNA-dependent RNA polymerase which can transcribe RNA from the self-replicating RNA molecule.

In a further specific embodiment is provided a vaccine composition for use in preventing influenza virus infection against homologous and/or heterologous intrasubtypic strains of influenza virus wherein the vaccine composition comprises (i) a first self-replicating RNA molecule encoding a polypeptide comprising a first antigen and (ii) a second self-replicating RNA molecule encoding a polypeptide comprising a second antigen, wherein:

- the first and second antigens are both from influenza virus but the first antigen is from a different strain of influenza virus to the second antigen,
- the first and second antigens are hemagglutinin or an immunogenic fragment or variant thereof and
- as well as encoding a polypeptide comprising an antigen from influenza virus, each self-replicating RNA molecule encodes a RNA-dependent RNA polymerase which can transcribe RNA from the self-replicating RNA molecule.

In a further specific embodiment is provided a vaccine composition for use in preventing influenza virus infection against homologous and/or heterologous intrasubtypic strains of influenza virus wherein the vaccine composition comprises (i) a first self-replicating RNA molecule encoding a polypeptide comprising a first antigen (ii) a second self-replicating RNA molecule encoding a polypeptide comprising a second antigen, and (iii) a third self-replicating RNA molecule encoding a polypeptide comprising a third antigen, wherein:

- the first, second and third antigens are both from influenza virus but the first, second and third antigens are all from different strains of influenza virus,
- the first, second and third antigens are hemagglutinin or an immunogenic fragment or variant thereof and
- the self-replicating RNA molecules are formulated in lipid nanoparticles (LNP) or a cationic nanoemulsion (CNE).

In a further specific embodiment is provided a vaccine composition for use in preventing influenza virus infection against homologous and/or heterologous intrasubtypic strains of influenza virus wherein the vaccine composition comprises (i) a first self-replicating RNA molecule encoding a polypeptide comprising a first antigen (ii) a second self-replicating RNA molecule encoding a polypeptide comprising a second antigen, and (iii) a third self-replicating RNA molecule encoding a polypeptide comprising a third antigen, wherein:

- the first, second and third antigens are both from influenza virus but the first, second and third antigens are all from different strains of influenza virus,
- the first, second and third antigens are hemagglutinin or an immunogenic fragment or variant thereof, and
- as well as encoding a polypeptide comprising an antigen from influenza virus, each self-replicating RNA molecule encodes a RNA-dependent RNA polymerase which can transcribe RNA from the self-replicating RNA molecule.

In a further specific embodiment is provided a vaccine composition for use in preventing influenza virus infection against homologous and/or heterologous intrasubtypic strains of influenza virus wherein the vaccine composition comprises (i) a first self-replicating RNA molecule encoding a polypeptide comprising a first antigen (ii) a second self-replicating RNA molecule encoding a polypeptide comprising a second antigen, and (iii) a third self-replicating RNA molecule encoding a polypeptide comprising a third antigen, wherein:

- the first, second and third antigens are both from influenza virus but the first, second and third antigens are all from different strains of influenza virus,
- the first, second and third antigens are hemagglutinin or an immunogenic fragment or variant thereof,
- the self-replicating RNA molecules are formulated in lipid nanoparticles (LNP) or a cationic nanoemulsion (CNE) and
- as well as encoding a polypeptide comprising an antigen from influenza virus, each self-replicating RNA molecule encodes a RNA-dependent RNA polymerase which can transcribe RNA from the self-replicating RNA molecule.

In some embodiments, methods are provided for preventing or shortening influenza virus infection and/or reducing or preventing the clinical symptoms upon influenza virus infection in a subject in need thereof, which comprises administering to said subject an immunologically effective amount of an immunogenic composition as provided herein.

In some embodiments, methods are provided for preventing or shortening influenza virus infection against multiple different strains of influenza virus. For example, the methods may be for preventing or shortening influenza virus infection against two or more H1 and/or two or more H3 type strains of influenza virus and optionally against two or more strains of influenza B virus. The methods may be for preventing or shortening influenza virus infection against both seasonal and pandemic strains of influenza virus. In some embodiments, the methods described herein may be for use in preventing influenza virus infection against homologous and/or heterologous strains of influenza virus.

In some embodiments is provided use of a composition disclosed herein in the manufacture of an immunogenic composition for preventing or shortening influenza virus infection in a subject and/or reducing or prevent the clinical symptoms upon influenza virus infection in a subject.

In some embodiments, the subject is a human subject. In specific embodiments, the human subject has been exposed, or is at risk of being exposed, to an influenza virus infection.

In some embodiments, multiple compositions comprising one or more self-replicating RNA molecules that encode a polypeptide comprising an antigen from influenza virus may be used. Hence, there is provided is a method of prevention and/or treatment against influenza disease, comprising (i) the administration of a first immunogenic composition comprising a first self-replicating RNA molecule and pharmaceutically acceptable carrier and (ii) simultaneous or sequential administration of a second immunogenic composition comprising a second self-replicating RNA molecule and pharmaceutically acceptable carrier, wherein the first and second self-replicating RNA molecules each encode a polypeptide encoding an antigen from influenza virus but the first self-replicating RNA molecule encodes an antigen from a different strain of influenza to that encoded by the second self-replicating RNA molecule.

The compositions may be administered sequentially, for example at substantially the same time such as at an interval of less than 10 hours, from 1 second to 10 hours or from 1 second to 1 hour, or at larger intervals of from 10 hours to 6 months, from 10 hours to 1 month, from 10 hours to 2 weeks, from 10 hours to 1 week or from 10 hours to 1 day. Preferably, the sequential administration is at an interval of from 1 second to 10 hours. The first or second immunogenic composition may comprise one or more additional (e.g. a 3rd, 4th, 5th, 6th, 7th, 8th, 9th and/or 10th) self-replicating RNA molecules each encoding a polypeptide comprising an antigen from influenza virus, but wherein the antigen in each self-replicating RNA molecule is from a different strain of influenza virus to the other antigens from influenza virus.

Hence, in a specific embodiment is provided is a method of prevention and/or treatment against influenza disease, comprising (i) the administration of a first immunogenic composition comprising a first self-replicating RNA molecule and pharmaceutically acceptable carrier and (ii) simultaneous or sequential administration of a second immunogenic composition comprising a second self-replicating RNA molecule and pharmaceutically acceptable carrier, wherein:

- the first and second self-replicating RNA molecules each encode a polypeptide encoding an antigen from influenza virus but the first self-replicating RNA molecule encodes an antigen from a different strain of influenza to that encoded by the second self-replicating RNA molecule
- the antigen from influenza virus is hemagglutinin or an immunogenic fragment or variant thereof and
- the second immunogenic composition is administered from 1 day to 6 months after the first immunogenic composition.

Also provided is a first immunogenic composition comprising a first self-replicating RNA molecule and a pharmaceutically acceptable carrier for use in a method of preventing influenza disease, said method comprising administration to a subject in need the first immunogenic composition followed by administration of a second immunogenic composition comprising a self-replicating RNA molecule and a pharmaceutically acceptable carrier, wherein the first and second self-replicating RNA molecules each encode a polypeptide comprising an antigen, wherein the antigen is from influenza virus but the antigen encoded by the first self-replicating RNA molecule is from a different strain of influenza virus to that encoded by the second self-replicating RNA molecule.

The compositions may be administered at an interval of less than 10 hours, from 1 second to hours or from 1 second to 1 hour, or at larger intervals of from 10 hours to 6 months, from 10 hours to 1 month, from 10 hours to 2 weeks, from 10 hours to 1 week or from 10 hours to 1 day.

The first/second immunogenic composition may comprise one or more additional (e.g. a 3rd, 4th, 5th, 6th, 7th, 8th, 9th and/or 10th) self-replicating RNA molecules each encoding a polypeptide comprising an antigen from influenza virus, but wherein the antigen in each self-replicating RNA molecule is from a different strain of influenza virus to the other antigens from influenza virus.

In a specific embodiment is provided a a first immunogenic composition comprising a first self-replicating RNA molecule and a pharmaceutically acceptable carrier for use in a method of preventing influenza disease, said method comprising administration to a subject in need the first immunogenic composition followed by administration of a second immunogenic composition comprising a self-replicating RNA molecule and a pharmaceutically acceptable carrier, wherein:

- the first and second self-replicating RNA molecules each encode a polypeptide comprising an antigen, wherein the antigen is from influenza virus but the antigen encoded by the first self-replicating RNA molecule is from a different strain of influenza virus to that encoded by the second self-replicating RNA molecule and the antigen from influenza virus is hemagglutinin or an immunogenic fragment or variant thereof and the second immunogenic composition is administered from 1 day to 6 months after the first immunogenic composition Routes of Administration/Dosages Compositions disclosed herein will generally be administered directly to a subject. Direct delivery may be accomplished by parenteral injection (e.g. subcutaneously, intraperitoneally, intravenously, intramuscularly, intradermally, or to the interstitial space of a tissue). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. The dose volume may be from 0.25 ml to 1 ml, in particular 0.5 ml or 0.7 ml. Slight adaptation of the dose volume will be made routinely depending on the RNA concentration in the original bulk sample and depending also on the delivery route, with smaller doses being given by the intranasal or interdermal route. A typical human intramuscular dose volume is 0.5 ml.

A dose of a self-replicating RNA vaccine may have about 50 μg to about 100 μg nucleic acid. In one embodiment, a vaccine dose contains 50, 55, 60, 65, 70, 75, 80, 85, 90, 95 or 100 μg self-replicating RNA. In other embodiments, a dose of a composition according to the invention may have <10 μg self-replicating RNA; e.g. from 1-10 μg, such as about 1 μg, 2.5 μg, 5 μg, 7.5 μg or 10 μg, but expression can be seen at much lower levels; e.g. using <1 μg/dose, <100 ng/dose, <10 ng/dose, <1 ng/dose, etc.

In preferred embodiments, a composition disclosed herein is administered to a subject at an effective dose, meaning a dose sufficient to achieve a desired immune response, such as induction of neutralizing antibodies to influenza virus and/or protection against influenza virus infection.

In some embodiments, a composition described herein (such as a vaccine composition) has an effective dose that is less than or equal to 50%, 40%, 30%, 20% or 10% of the effective dose of a DNA vaccine or vaccine composition encoding the same antigen. In some embodiments, a vaccine described herein has an effective dose that is one third or less of the effective dose of a DNA vaccine or vaccine composition encoding the same antigen.

Processes of Manufacture/Formulation

Processes for the manufacture of self-replicating RNA are provided herein. In some embodiments, the process of manufacturing a self-replicating RNA comprises a step of in vitro transcription (IVT) as described elsewhere herein. In some embodiments, the process of manufacturing a self-replicating RNA comprises a step of IVT to produce a RNA, and further comprises a step of combining the RNA with a non-viral delivery system as described elsewhere herein. In some embodiments, the process of manufacturing a self-replicating RNA comprises a step of IVT to produce a RNA, and further comprises a step of combining the RNA with a CNE or LNP delivery system as described elsewhere herein.

Sequence Identity

Identity or homology with respect to an amino acid sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity. Identity or homology with respect to a nucleic acid sequence is defined herein as the percentage of nucleotides in the candidate sequence that are identical with the reference nucleic acid sequence after aligning the sequences and introducing gaps, if necessary, to achieve the maximum percent sequence identity.

Sequence identity can be determined by standard methods that are commonly used to compare the similarity in position of the amino acids of two polypeptides. Using a computer program such as BLAST, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the shorter sequences in order to align the two sequences. The same methods used to compare polypeptides can also be used to calculate the percent identity of two polynucleotide sequences.

Where the present disclosure refers to a sequence by reference to a UniProt or Genbank accession code, the sequence referred to is the current version at the filing date of the present application.

General

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%.

The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. Embodiments described as comprising certain components are intended to include embodiments consisting of the indicated components.

The abbreviation, "e.g." is derived from the Latin exempli gratia, and is used herein to indicate a non-limiting example. Thus, the abbreviation "e.g." is synonymous with the term "for example."

The invention will be further described by reference to the following, non-limiting, figures and examples.

EXAMPLES

Example 1—Materials and Methods

Selection of Influenza H3N2 Vaccine Strains

Potential pandemic and seasonal strains of the influenza H3N2 subtypes were selected on the basis of three major criteria 1) major glycosylation sites 2) important seasonal and pandemic vaccine strains 3) cell adapted strains only. Sequence information for full length genes encoding for influenza HA proteins was obtained from the Global Initiative on Sharing All Influenza Data Epiflu database (www-.gisaid.org). All together 6 H3N2 HA gene segments from A/Bilthoven/16398/1968 (EPI362379), A/Bangkok/1/79 (EPI367158), A/Beijing/32/92 (EPI365898), A/Fujian/411/2002 (EPI362915), A/Brisbane/10/2007 (EPI362338) and A/Texas/50/2012 (EPI398417) were selected.

| Strains | EPI-Segment-ID* |
|---|---|
| A/California/07/2009 (H1N1) | EPI516528 |
| A/PR/8/34 (H1N1) | EPI131282 |
| A/turkey/Turkey/1/2005 (H5N1) | EPI102703 |
| A/Bilthoven/16398/1968 (H3N2) | EPI362379 |
| A/Bangkok/1/79 (H3N2) | EPI367158 |
| A/Beijing/32/92 (H3N2) | EPI365898 |
| A/Fujain/411/2002 (H3N2) | EPI362915 |
| A/Brisbane/10/2007 (H3N2) | EPI362338 |
| A/Texas/50/2012 (H3N2) | EPI398417 |
| A/Anhui/1/2013 (H7N9) | EPI539507 |
| A/Memphis/1/1971 (H3N2) | EPI137302 |
| A/Moscow/10/1999 (H3N2) | EPI103359 |
| A/Japan/305/1957 (H2N2) | EPI240974 |
| A/duck/Hongkong/562/1979 (H10N9) | EPI42118 |

*Source: Global Initiative on Sharing All Influenza Data Epiflu database (www.gisaid.org)

SAM Replicons and RNA Synthesis

Monocistronic SAM(HA) vaccine constructs, SAM (H1-Cal), SAM (H1-PR8), SAM (H5-turkey), SAM (H3-Biltho), SAM (H3-Bang), SAM (H3-Beij), SAM (H3-Fuj), SAM (H3-Bris), SAM (H3-Tex) and SAM (H7-Shan), were generated after cloning full length HA gene segment of A/California/07/2009 (H1N1), A/PR/8/1934 (H1N1), A/turkey/Turkey/5/2005 (H5N1), A/Bilthoven/16398/1968 (H3N2), A/Bangkok/1/79 (H3N2), A/Beijing/32/92 (H3N2), A/Fujian/411/2002 (H3N2), A/Brisbane/10/2007 (H3N2), A/Texas/50/2012 (H3N2) and A/Shanghai/1/2013 (H7N9), respectively in an alphavirus based SAM vector TC83. Similarly, a bicistronic SAM construct (FIG. 1*a*) harboring two HA genes, H5 and H1, was produced by cloning the second HA gene downstream of the full length 2A-driven sequence using a splicing by overlap extension (SOEing) method with monomeric HA forms as primary PCR templates. The primers used for the SOEIng PCRs are shown below:

catagtctagtcgacgccaccatggagaaaatagtgcttcttcttgc (SB63)
gtcgaagttcagggtctgcttcacgggggccacgatcttctgcttgtgccgg-gcctcccgcttggcccgaatgcaaattctgcattgt aacgatc (SB74)
gtgaagcagaccctgaacttcgacctgctgaagctggccggcgacgtg-gagagcaaccccggccccatgaaggcaatactagta gttctgc (SB76)
ggcgtagcggcggccgcttatcaaatacatattctacactgtagagaccca (SB66)

Self-amplifying mRNAs were prepared as previously described (Hekele et al Emerg Microbes Infect 2013; 2 doi:ARTN e52DOI 10.1038/emi.2013.54) Briefly, full length HA genes were either chemically synthesized (GeneArt, Thermo Fischer, USA) or amplified from the reverse-transcribed RNA genome of influenza H1N1 A/California/07/2009 using forward primer 5'-ATT CCC GTC GAC GCC ACC ATG AAG GCA ATA CTA GTA GTT CT-3' and reverse primer 5'-ATT TAC GCC TAG GTT ATC AAA TAC ATA TTC TAC ACT GTA GAG AC-3D. The full-length H5 HA gene (H5) from A/turkey/Turkey/01/2005 (H5N1) virus strain was also amplified. Further, H7 HA gene from A/Shanghai/2/2013 was amplified from a DNA fragment, assembled based on a previously described enzymatic isothermal assembly method with error correction (Dormitzer et al, Sci Transl Med 2013, 15; 5(185):185ra68), using forward primer 5'-AAT TAA GTC GAC GCC ACC ATG AAC ACT CAA ATC CTG GTA TTC G-3' and reverse primer 5'-AAT TAA TCT AGA TTA TCA TAT ACA AAT AGT GCA CCG CAT G-3'. Amplicons were cloned into the A836 TC83 vector shown as SEQ ID NO: [INSERT no. for TC83 sequence].

Plasmids were amplified in *Escherichia coli* and purified using Qiagen maxi Kits (Qiagen, Valencia, CA, USA). DNA was linearized immediately following the 3' end of the self-amplifying RNA sequence by restriction digestion with PmeI Linearized DNA plasmids were transcribed in to RNA using MEGAscript T7 Kit (Life Technologies) and purified by LiCl precipitation. RNA was then capped using the ScriptCap $m^7G$ capping system (Cell Script) and purified by 2.8 M LiCl precipitation before formulation. Protein expression was confirmed by Western blot analysis of transfected baby hamster kidney (BHK) cell lysate.

RNA Amplification and Protein Expression Analysis

RNA amplification efficiency was carried out, as previously reported (Magini et al, PLoS One 2016; 11(8): e0161193). Briefly, BHK cells were electroporated with 200 ng of RNA and incubated for overnight (15-17) hours at 37° C. and 5% $CO_2$. Next day, cells were collected and stained with Live/Dead Aqua (Invitrogen), APC-conjugated anti-double stranded (ds) RNA antibody (J2 monoclonal mouse antibody IgG2a kappa chain, Bioclass). Frequencies of dsRNA+ cells were analyzed by FACS CANTO II flow cytometer (BD Biosciences).

To confirm expression of HA from replicon RNA, $10^6$ BHK cells were transfected with 3 μg of each RNA using Lipofectamine 2000™ (LifeTechnologies, CA, USA). Cells were harvested 16 hours after transfection and lysed in 100 μL of 1× radio-immunoprecipitation assay (RIPA) buffer (Cell Signaling Technology, MA, USA) with complete protease inhibitor cocktail (Roche, Madison, WI, USA). Lysates were subjected to SDS-PAGE and blotted on to PVDF membrane. Protein expression was detected with HA-specific monoclonal or polyclonal antibodies.

LNP/RNA Formulation

Equal amount of RNAs were mixed prior to encapsulation in LNPs. Formulations were characterized for particle size, RNA concentration, encapsulation efficiency and RNA integrity (using gel electrophoresis) as previously described (Hekele et al, Emerg Microbes Infect 2013). Encapsulation of RNA within LNP was carried out as described previously (Geall et al Proc Natl Acad Sci USA 2012; 109:14604-9). DLinDMA was synthesized as previously described (Heyes et al, J Control Release 107:276-287). The 1,2-Diastearoyl-sn-glycero-3-phosphocholine (DSPC) was purchased from Genzyme. Cholesterol was obtained from Sigma-Aldrich. 1,2-dimyristoyl-sn-glycero-3-phosphoethanolamine-N-[methoxy(polyethylene glycol)-2000] (ammonium salt) (PEG DMG 2000) was obtained from Avanti Polar Lipids. An ethanol dilution process was used to produce the LNP formulation with the following molar ratios of lipid components: DSPC:cholesterol:PEG-DMG 2000:DLinDMA 10:48:2:40 molar percent. An 8:1 N:P molar ratio (nitrogen on DlinDMA to phosphate on RNA) and 100 mM citrate buffer (pH 6) were used for the formulations. In the first step of the in-line mixing, equal volumes of lipid (in ethanol) and RNA in buffer were mixed, through a T-junction via a KDS-220 syringe pump (kdScientific), and a third syringe with equal volume of buffer was added simultaneously to the lipid/RNA mixture. After 1 h equilibration at room temperature, the mixture was further diluted with 1:1 vol/vol citrate buffer. Next, the LNPs obtained ("RV01" LNPs) were concentrated and dialyzed against 1× PBS using tangential flow filtration (TFF) (Spectrum Labs) with polyethersulfone (PES) hollow fiber membranes with a 100-kDa pore size cutoff and 20 $cm^2$ surface area. For in vitro and in vivo experiments, formulations were diluted to the required RNA concentration with 1× PBS (Teknova).

In Vivo Models

Mice were housed in the GlaxoSmithKline (GSK) Vaccines Animal Facilities, in compliance with ARRIVE guidelines and with the GSK Animal Welfare Policy and Standards. Female BALB/c mice, aged 6-8 weeks, were obtained from Charles River Laboratories, Italy. To access breadth of immune responses, groups of 10 mice were immunized intramuscularly (i.m.) with each 0.1 μg of each LNP encapsulated monocistronic or bicistronic SAM RNA separately: SAM (H1-Cal); SAM (H5-turkey); SAM (H5-H1) or in combination of groups: SAM(H1)+SAM(H5); SAM(H3-Biltho)+SAM(H3-Bang)+SAM(H3-Fuj) [group 2]; SAM (H3-Beij)+SAM(H3-Bris)+SAM(H3-Tex) [group 3]; SAM (H1-Cal)+SAM(H1-PR8)+SAM(H5-turkey)+SAM (H7-Shan) [group 4]; SAM(H3-Biltho)+SAM(H3-Bang)+SAM (H3-Fuj)+SAM(H3-Beij)+SAM(H3-Bris)+SAM(H3-Tex) [group 5] and SAM(H3-Biltho)+SAM(H3-Bang)+SAM (H3-Fuj)+SAM(H3-Beij)+SAM(H3-Bris)+SAM(H3-Tex)+ SAM(H1-Cal)+SAM(H1-PR8)+SAM(H5-turkey)+SAM (H7-Shan) [group 6] twice at 3 week intervals (see FIG. 5). As control PBS was used [group 1]. Blood samples were collected 2 weeks after the second immunization for HA-specific humoral responses assessment. Spleens from 6 animals were collected form each group for evaluating $CD4^+$ and $CD8^+$ T cell responses.

Hemagglutination Inhibition Assay

Serum Ab titers measured by hemagglutination inhibition (HI) assays were performed according to standard procedure using a 0.5% suspension of adult turkey erythrocytes. To inactivate nonspecific inhibitors, all serum samples were pre-treated with receptor-destroying enzymes (DENKA, Tokyo, Japan) according to manufacturer's instructions. Duplicate of individual sera were serially 2-fold diluted in V-bottom microtiter plates to achieve serum final dilutions of 1:10. Diluted sera samples were incubated with an equal volume of strain-specific influenza antigen for 60 min at room temperature followed by 60 min incubation with 0.5% turkey red blood cell suspension. The outcomes were analyzed by visual inspection and HI titres calculated as the reciprocal of the last serum dilution at which the last complete agglutination occurred.

Intracellular Cytokine Staining

To characterize antigen-specific T-cell responses, single cell suspension of $1.5\times10^6$ splenocytes were cultured with H1-Cal or H5-turkey (JPT, Berlin, Germany) or H1-PR8 (Department of Biochemistry, University of Lausanne, Switzerland) peptide pools or CD4 restricted ALNNRFQIKGVELKS (for A/Memphis/1/1971, H3N2) (Fitzmaurice et al, Vaccine 1996; 14:553-60) peptides at 2.5 μg/ml and recombinant HA proteins at 5 μg/ml concentration (Sino Biologicals Inc.) in complete RPMI media containing brefeldin A in the presence of CD107a FITC (BD Biosciences, USA). For flow cytometry analysis, cells were then stained with Live/Dead Near InfraRed (Invitrogen, USA), anti-CD62L (BD Pharmingen), fixed and permeabilized with Cytofix/Cytoperm (BD Biosciences), and further incubated with anti-CD16/CD32 Fc-block (BD Biosciences). T-cells were stained with anti-CD3-PerCp-Cy5.5, anti-CD4-BV510, anti-CD8-PE-Texas Red, anti-CD44-240 V450, anti-IFN-γ Bv785, anti-IL-2-PEcy5, anti-TNF-BV605 (All from eBiosciences). Samples were then acquired on a LSRII special order flow cytometer (BD Biosciences) and data were analyzed using FlowJo software version 9.7.4 (TreeStar). Frequencies of antigen-specific T-cells were determined after subtracting the background measured in the corresponding negative control for each cytokine.

Statistical Analyses

All statistical analyses were performed using GraphPad Prism 5 software (GraphPad Software, La Jolla, USA). Mann-Whitney U test was used to analyze HI titers and T-cell frequencies. P value of less than 0.05 was considered significant.

Example 2—Generation and Characterisation of SAM Vaccines Expressing One or More Influenza HA Antigens Firstly, full length HA gene segments from H1N1 (A/California/07/2009) and H5N1 (A/turkey/Turkey/5/2005) were cloned into the TC83 alphavirus vector comprised of VEE/SINV (Venezuelan equine encephalitis-Sindbis virus) chimeric replicon containing T7 DNA polymerase promoter (Perri et al.; Journal of Virology October 2003, p 10394-10403) as monocistronic SAM (H1-Cal), SAM (H5-turkey) and bicistronic SAM (H5-H1) replicons. In the next step, 8 more monocistronic SAM (HA) replicons SAM (H1-PR8), SAM (H3-Biltho), SAM (H3-Bang), SAM (H3-Beij), SAM (H3-Fuj), SAM (H3-Bris), SAM (H3-Tex) and SAM (H7-Shan) were generated. In-vitro synthesis of RNAs from all the SAM replicons was carried out by enzymatic transcription reaction from linearized DNA. Self-amplification efficiency of RNA was measured by quantitative detection of the intracellular dsRNA in BHK cells, followed by flow cytometric analysis.

BHK cells positive for dsRNA after transfection with monocistronic and bicistronic SAM (HA) replicons were comparable with RNA of known potency. Protein expression ability of SAM replicons was tested by transfecting the BHK cells and then subjected to western blot analysis. Expression of influenza HA from H1, H5 (FIG. 1), H3 (FIG. 7), and H7 from monocistronic and bicistronic SAM (FIG. 1) replicons showed protein expression using HA-specific antibodies. Before mice immunization, SAM replicons were encapsulated in the LNP delivery system as described in Example 1. Mean particle size and polydispersity was measured by dynamic light scattering for all eleven LNP/RNA formulations. The Z average diameter of LNPs ranged from 137 to 163 nm with polydispersity index 0.01 to 0.14. Further SAM/LNP complexes were also tested for encapsulation efficiency and showed that LNPs were able to encapsulate approximately 95% of mRNA. LNP/RNA particle size and encapsulation efficiency data suggest that LNP are excellent delivery vehicles for nucleic acid delivery. Agarose gel electrophoresis showed that RNA integrity was maintained during formulation.

Example 3—Humoral Immune Responses Following Monocistronic SAM(H1-Cal), SAM(H5-Turkey) or Bicistronic SAM (H5-H1) Vaccines As previously mentioned, groups of 10 Balb/c mice vaccinated i.m. twice, 3 weeks apart, with 0.1 μg of SAM (H1-Cal), SAM (H5-turkey), a mixture of both SAM(H1)+SAM(H5) or SAM (H5-H1) and formulated with LNP. Serum samples were collected about 3 weeks after the first immunization and 2 weeks after the second immunization. However, only final serum samples were analyzed for antibody responses because previous results suggested that SAM vaccines can induce immune responses already at 3 weeks after a first immunization (Hekele et al, Emerg Microbes Infect, 2013; 2, e52).

Serum samples from vaccinated Balb/c mice were tested for the presence of HA-specific functional antibodies by HI assays. Animals that received monocistronic SAM(H1-Cal)/LNP or SAM(H5-turkey)/LNP vaccine candidates developed geometric mean titer (GMT) of 597 and 905, respectively against homologous A/California/07/2009 (H1N1) and A/turkey/Turkey/5/2005 (H5N1)(FIG. 2 *a* & b). Interestingly, HI GMTs of bicistronic of SAM(H5-H1)/LNP appeared more than two fold lower than monocistronic vaccines against A/California/07/2009 (H1N1) and A/turkey/Turkey/5/2005 (H5N1) viruses suggesting that combinations of two different influenza antigens in a single SAM vector is not effective in boosting functional antibody responses (FIG. 2 *a* & b). Moreover, the combination of SAM(H1)+SAM(H5)/LNP candidate vaccines induced comparable responses to monocistronic SAM(H1-Cal) or SAM(H5-turkey) and the difference was not statistically significant (FIG. 2 *a* & b). Next, we tested whether the combination of two different antigens can induce cross-reactive functional antibodies or not. Serum from vaccinated mice subjected for HI analysis with antigenically different A/PR/8/1934 (H1N1) and A/Perth/16/2009 (H3N2) virus strains. Cross-reactivity was not observed in any of the vaccinated groups (FIG. 2 *c* & d).

Discussion

A bicistronic SAM (HA) vector expressing HA from two different influenza subtypes (H1N1 and H5N1) was developed and the ability to induce cross-reactive immune responses tested. Existing reports suggest that both subtypes induced cross-protective immunity in humans and animals (Brazzoli et al, J Virol 2015; 90:332-44, Wrammert et al, J Exp Med 2011; 208:181-93, Sridhar et al, Front Immunol 2016; 7, Florek et al, J Virol 2014; 88:13418-28). Cross-reactive antibodies against antigenically distant heterologous strains A/PR/8/1934 (H1N1) and A/Perth/16/2009), were not detected after 2 doses of bicistronic SAM(H5-H1) or monocistronic SAM(H1-Cal), SAM(H5-turkey) or combinations of SAM(H1)+SAM(H5) vaccines. Absence of antibody mediated cross-reactivity was not surprising and is consistent with the obligation for an annual update of seasonal influenza vaccines. However, the strength of the antibody responses induced by bicistronic SAM (H5-H1) was lower than SAM(H1-Cal) or SAM(H5-turkey) ($<p=0.001$), suggesting that individual SAM (HA) replicons expressing influenza antigens are more effective. Interestingly, cross-reactive intrasubtypic and heterosubtypic $CD4^+$ and $CD8^+$ were detected. The results suggest that in the absence of cross reactive neutralizing antibodies, T cells may provide protection against antigenically different viruses.

Example 4—Cellular Immune Responses Following Monocistronic SAM(H1-Cal), SAM(H5-Turkey) or Bicistronic SAM (H5-H1) Vaccines To characterize functional T-cell responses induced by the vaccine candidates, Balb/c mice were immunized with 0.1 μg of SAM/LNP and splenocytes were collected 2 weeks after the second vaccination and stimulated in-vitro with peptide pools covering full length HA sequence from H1-Cal and H5-turkey. The frequencies of antigen-specific $CD4^+$ and $CD8^+$ cytokine producing (IFN-γ, TNFα and IL-2) T-cells were analyzed by flow cytometry. All vaccine groups elicited HA-specific $CD4^+$ T-cell responses with T helper (Th) cell profile Th0/Th1 phenotype (dominated by secretion of IFN-γ and combinations IFN-γ/TNF and IFN-γ/TNF/IL-2) (FIG. 2 *e, f* & g). Influenza HA-specific $CD8^+$ T-cells were also investigated and mostly HA-specific T-cells found positive for IFN-γ and TNF cytokines (FIG. 2 *h*, I &j). Further, expression of cell surface marker CD107a was also observed, specific for degranulation associated with cytotoxic activity. A significant number of $CD8^+$ T-cells were found positive for CD107a (FIG. 2 *k, l* & m). Splenocytes from Balb/c mice vaccinated with SAM (H1-Cal) and SAM (H5-turkey) were stimulated with peptide pools spanning full length HA from H1/PR/8 influenza virus for determination of heterologous T-cell responses. Stimulated $CD4^+$ and $CD8^+$ T-cells reacted with mismatched H1-PR8 peptide pools (FIG. 2 *g, j* & m) suggesting the presence of shared T-cell epitopes in HA antigens from heterologous virus strains. Cross-reactive T-cell responses against bicistronic vaccine candidates were not tested because of limitations in the amount of splenocytes.

Example 5—Vaccination with a Cocktail of SAM Vectors Expressing HA of H3, H1, H5 and H7 Influenza Subtypes Induction of Functional Antibodies In the present study, the immunogenicity of multivalent vaccines comprised of cocktails of 10 SAM replicons expressing HAs from four different influenza subtypes (H1N1, H3N2, H5N1 and H7N9) have been assessed. Cocktails of 3, 4, 6 or 10 different mRNAs (each 0.1 μg) were encapsulated in lipid nanoparticles (LNP). Groups of 10 Balb/c mice were immunized i.m. with multivalent SAM (HA) vaccine or PBS. Sera samples were collected 2 weeks after second immunization (day 35) and functional antibodies were studied by HI assays.

First, sera from vaccinated mice were analyzed with influenza HA viral antigens that were identical to those contained in the SAM (HA) cocktail vaccines (homologous responses) (FIG. 3 *a* to *g*). All vaccinated mice were shown to induce functional antibody responses. Functional antibody responses against the vaccine cocktail groups containing 3 SAM(HAs) (group 2 and 3) showed stronger responses than cocktail group 6 (containing 10 SAM(HAs).

To evaluate whether the multivalent vaccine could have role in protection against mismatched influenza virus, sera samples were analyzed with heterologous influenza virus antigens. Cross-reactive functional antibodies were found against all heterologous virus strains except H7N9 (A/Anhui/2013) (FIG. 3) Greater responses were observed among H3N2 subtypes. The magnitude of the HI responses against different vaccine cocktails was also analyzed. Compared to LNPs with 6 different RNAs (group 5) of the same subtypes, LNPs with 3 SAM RNAs (groups 2 and 3) boosted 1.1 to 2.7 times the antibody responses ($P<0.3006$) (FIG. 3 *d* to *g*).

While in the presence of SAM replicons from other subtypes (group 2 and 3 Vs 6) 3 SAM replicons boosted 1.3 to 2.6 time the responses (P<0.0252) (FIG. 3 *d* to *g*). No increase was found in LNP with 6 SAM RNAs (group 5) compared to 10 SAM RNAs (group 6). Between group 4 and 6 an increase of 1.7 to 4 times was detected (P<0.0094) (FIGS. 3*a* & *b*).

Induction $CD4^+$ Mediated Immune Responses

To determine whether multivalent SAM(HA) vaccine-induced $CD4^+$ T-cell responses provide protection against mismatched influenza virus, groups of mice were vaccinated with multivalent SAM (HA) vaccine twice, 3 weeks apart. $CD4^+$ T cells responses were analyzed by in-vitro stimulation of splenocytes from vaccinated Balb/c mice with full length recombinant HA proteins and peptide pools.

Firstly, $CD4^+$ T-cell responses against HA recombinant proteins or peptides from homologous influenza viruses were tested: A/Fujian/411/2002, A/Brisbane/10/2007, A/Texas/50/2012 (H3N2), A/turkey/Turkey/1/2005 (H5N1) and A/California/07/2009, A/PR/8/1934 (H1N1). Results demonstrated CD4+ T cell responses against all homologous influenza HAs (FIG. 4 *a* to *f*). Interestingly, stimulated CD4+ T cells with peptide pools from A/California/07/2009, A/PR/8/1934 (H1N1) and A/turkey/Turkey/1/2005 (H5N1) also induced responses in other groups where antigens from those strains were not included in the SAM multivalent vaccine (FIG. 4 *a* to *c*). To determine the cross-protection conferred by the multivalent SAM vaccines, we analyzed mice splenocytes with intrasubtypic and heterosubtypic virus strains. All SAM (HA) vaccine groups containing H3 (groups 2, 3, 5 and 6) HA induced cross reactive CD4+ T cell responses against distantly or closely related H3N2 influenza virus strains. These results suggest that intra-subtypic strains of the virus are sharing sufficient number of T cell epitopes. Furthermore, CD4+ T cell responses were detected against other subtypes from which HA antigens were not included in the SAM (HA) multivalent vaccines (FIG. 4 *k* & *l*). However, cell frequencies of cytokine expressing $CD4^+$ T cells were only <0.1%. CD4 T cell responses in group 6 with 10 SAM (HA) expressing HA antigens exhibit comparable responses to those with fewer SAM (HA) antigens suggesting the utility of a SAM vaccine platform for development of a multivalent influenza vaccine.

Discussion

Glycosylation pattern directly contributes to virulence and is partially responsible for distinct antigenicity of influenza viruses. Glycosylation sites present on the globular head domain of HA can tolerate substitutions without compromising functionality and antibodies generated are generally strain-specific with limited breadth of cross reactivity (Gomez Lorenzo et al, Chest 2013; 143:502-10). In contrast, the HA stem domain is highly conserved across several virus strains and in many studies antibodies directed against the stem are found with cross neutralizing properties (Sun et al, J Virol, 2013; 87:8756-66 and Nabel et al, Nat Med 2010; 16:1389-91). Therefore, HA is an attractive candidate for a multivalent influenza vaccine. In the present Examples, there is a focus on a multivalent vaccine containing H3N2 subtypes because of a higher variability in glycosylation in HA antigen. Mostly strains from past and present seasonal vaccines and also pandemic strains were selected. In particular, H3 strains were selected from 1968 to 2012 to try and capture the variability seen in glycosylation sites in the head.

The experiments described herein use a cocktail strategy by combining 3, 4, 6, or 10 SAM (HA) from H1, H3, H5 and H7 subtypes for exploring cross-protective B and T-cell immune responses in a Balb/c mice model. Sequences for particular strains are shown in Table 2. Multivalent SAM (HA) vaccines were tested for the induction of functional antibodies directed against homologous and heterologous influenza virus by HI assays. Homologous and intrasubtypic antibody responses were observed (FIGS. 3 *h, i, j* and *l*) because of high amino acid homology (see Table 1 below).

TABLE 1

| Amino-acid similarity (%) of HA gene segments among influenza subtypes | | | | | | | | | | | | |
|---|---|---|---|---|---|---|---|---|---|---|---|---|
| Strains | H1-Cal | H1-PR8 | H5 turkey | H3-Biltho | H3-Bang | H3-Beij | H3-Fuj | H3-Bris | H3-Tex | H7-Anh | H3-Mem | H3-Mos |
| H1-Cal | 100 | 82 | 62 | 43 | 43 | 44 | 42 | 43 | 42 | 41 | 43 | 42 |
| H1-PR8 | 82 | 100 | 65 | 42 | 42 | 42 | 41 | 41 | 41 | 41 | 43 | 41 |
| H5-turkey | 62 | 63 | 100 | 41 | 40 | 40 | 39 | 39 | 40 | 41 | 40 | 40 |
| H3-Biltho | 43 | 42 | 41 | 100 | 92 | 90 | 87 | 86 | 85 | 48 | 98 | 89 |
| H3-Bang | 43 | 42 | 40 | 92 | 100 | 95 | 90 | 90 | 89 | 47 | 93 | 92 |
| H3-Beij | 44 | 42 | 40 | 90 | 95 | 100 | 93 | 92 | 91 | 47 | 90 | 95 |
| H3-Fuj | 42 | 41 | 39 | 87 | 90 | 93 | 100 | 96 | 95 | 46 | 87 | 95 |
| H3-Bris | 43 | 41 | 39 | 86 | 90 | 92 | 96 | 100 | 97 | 46 | 87 | 93 |
| H3-Tex | 42 | 42 | 40 | 85 | 89 | 91 | 95 | 97 | 100 | 46 | 86 | 92 |
| H7-Anh | 41 | 41 | 41 | 48 | 47 | 47 | 46 | 46 | 46 | 100 | 47 | 47 |
| H3-Mem | 43 | 43 | 40 | 98 | 93 | 90 | 87 | 87 | 86 | 47 | 100 | 47 |
| H3-Mos | 42 | 41 | 40 | 89 | 92 | 95 | 95 | 93 | 92 | 47 | 89 | 100 |
| H2-Jap | 63 | 66 | 76 | 42 | 40 | 41 | 40 | 40 | 40 | 40 | 42 | 40 |
| H10-Ho | 43 | 43 | 42 | 52 | 51 | 51 | 49 | 50 | 49 | 65 | 52 | 50 |

ClustaAW (EMBL-EBI) tool was used for amino acid similarity search for full length HA gene sequences of H1-Cal (A/California/07/2009); H1-PR8 (A/PR/8/1934); H5-turkey (A/turkey/Turkey/5/2005); H3-Biltho (A/Bilthoven/16398/1968); H3-Bang (A/Bangkok2)/79); H3-Beij (A/Beijing/32/92); H3-Fuj (A/Fujian/411/2002); H3-Bris (A/Brisbane/10/2007); H3-Tex (A/Texas/50/2012); H7-Anh (A/Anhui/1/2013); H-3-Mem (A/Memphis/1/1971); H-3-Mos (A/Moscow/10/1999); H-2-Jap (A/Japan/305/1957); H10-Ho (A/duck/Hongkong/562/1979).

TABLE 2

| Strains | EPI-Segment-ID* |
|---|---|
| A/California/07/2009 (H1N1) | EPI516528 |
| A/PR/8/34 (H1N1) | EPI131282 |
| A/turkey/Turkey/1/2005 (H5N1) | EPI102703 |
| A/Bilthoven/16398/1968 (H3N2) | EPI362379 |
| A/Bangkok/1/79 (H3N2) | EPI367158 |

TABLE 2-continued

| Strains | EPI-Segment-ID* |
|---|---|
| A/Beijing/32/92 (H3N2) | EPI365898 |
| A/Fujain/411/2002 (H3N2) | EPI362915 |
| A/Brisbane/10/2007 (H3N2) | EPI362338 |
| A/Texas/50/2012 (H3N2) | EPI398417 |
| A/Anhui/1/2013 (H7N9) | EPI539507 |
| A/Memphis/1/1971 (H3N2) | EPI137302 |
| A/Moscow/10/1999 (H3N2) | EPI103359 |
| A/Japan/305/1957 (H2N2) | EPI240974 |
| A/duck/Hongkong/562/1979 (H10N9) | EPI42118 |

sequences obtained from Global Initiative on Sharing All Influenza Data Epiflu database (www.gisaid.org)

Despite the absence of cross-reactive functional antibodies against heterotypic virus strains, vaccination with SAM (HA) H3N2 multivalent vaccines showed cross protective $CD4^+$ T-cells against A/PR/8/1934 (H1N1), A/California/07/2009 (H1N1) and A/turkey/turkey/2005 (H5N1) (FIG. 4 *a* to *c*). Heterotypic $CD4^+$ T cell responses were also detected against H7N9, H10N9 and H2N2 but to a lesser extent.

In this study, an alternative vaccine platform technology, based on SAM technology, is used to deliver multiple influenza antigens simultaneously and induce protective immune responses. This vaccine platform technology can induce a broad spectrum of immune responses and deliver multiple influenza antigens simultaneously without compromising antiginicity. This technology might be beneficial for the development of a universal influenza vaccine.

CLAUSES

Clause 1. An immunogenic composition comprising: (i) a first self-replicating RNA molecule encoding a polypeptide comprising a first antigen and (ii) a second self-replicating RNA molecule encoding a polypeptide comprising a second antigen, wherein the first and second antigens are both from influenza virus but the first antigen is from a different strain of influenza virus to the second antigen.

Clause 2. The immunogenic composition of clause 1 wherein the first and second antigens are hemagglutinin (HA).

Clause 3. The immunogenic composition of clause 1 wherein the first and second antigens are an immunogenic fragment or variant of hemagglutinin (HA).

Clause 4. The immunogenic composition of any preceding clause wherein the first antigen is from a different subtype of influenza virus to the second antigen.

Clause 5. The immunogenic composition of any preceding clause wherein the first and second antigens are the only antigens derived from influenza virus in the self-replicating RNA molecules.

Clause 6. The immunogenic composition of any preceding clause further comprising: (iii) a third self-replicating RNA molecule encoding a polypeptide comprising a third antigen, wherein the third antigen is from influenza virus but is from a different strain of influenza virus to both the first and second antigens.

Clause 7. The immunogenic composition of clause 6 wherein the first, second and third antigens are the only antigens derived from influenza virus in the self-replicating RNA molecules.

Clause 8. The immunogenic composition of clause 6 or 7 further comprising: (iii) a fourth self-replicating RNA molecule encoding a polypeptide comprising a fourth antigen, wherein the fourth antigen is from influenza virus but is from a different strain of influenza virus to both the first, second and third antigens.

Clause 9. The immunogenic composition of any preceding clause wherein the first antigen is from influenza A subtype H1 and the second antigen is from a different H1 strain to the first antigen.

Clause 10. The immunogenic composition of any one of clauses 1 to 8 wherein the first and second antigens are from influenza A subtype H3, and wherein both antigens are derived from different strains of H3 influenza virus.

Clause 11. The immunogenic composition of clause 8 wherein the first and second antigens are from influenza A subtype H1 and the third and fourth antigens are from influenza A subtype H3, and wherein the first and second antigens are derived from different strains of H1 virus and the third and fourth antigens are from different strains of H3 influenza virus.

Clause 12. The immunogenic composition of clauses 9 or 11 wherein the antigens are from influenza subtype H1N1.

Clause 13. The immunogenic composition of clauses 10 or 11 wherein the antigens are from influenza subtype H3N2.

Clause 14. The immunogenic composition of any of clauses 8 to 13 further comprising one or more further self-replicating RNA molecules, wherein each further self-replicating RNA molecules encodes a polypeptide comprising a further antigen, wherein each further antigen is from influenza virus but is from a different strain of influenza virus to any of the other antigens in the composition.

Clause 15. The immunogenic composition of clause 14 wherein the composition comprises 5, 6, 7, 8, 9 or 10 further self-replicating RNA molecules.

Clause 16. The immunogenic composition of any preceding clause wherein the composition comprises six self-replicating RNA molecules, wherein each self-replicating RNA molecules encodes a polypeptide comprising an antigen from a different strain of influenza subtype H3N2.

Clause 17. The immunogenic composition of any preceding clause further comprising an adjuvant.

Clause 18. The immunogenic composition of any preceding clause wherein the self-replicating RNA molecule is a derived from an alphavirus.

Clause 19. The immunogenic composition of clause 18 wherein the alphavirus is selected from the group consisting of: Sindbis (SIN), Venezuelan equine encephalitis (VEE), Semliki Forest virus (SFV) and combinations thereof.

Clause 20. The immunogenic composition of any preceding clause wherein the self-replicating RNA molecules are monocistronic.

Clause 21. A pharmaceutical composition comprising an immunogenic composition according to any one of the preceding clauses and a pharmaceutically acceptable carrier.

Clause 22. The pharmaceutical composition of clause 21 further comprising a cationic lipid, a liposome, a microparticle, viral replicon particles (VRPs), an oil-in-water emulsion or a cationic nanoemulsion.

Clause 23. The pharmaceutical composition of clause 23 wherein the self-replicating RNA molecules are encapsulated in, bound to or adsorbed on a cationic lipid, a liposome, a microparticle, viral replicon particles (VRPs), an oil-in-water emulsion or a cationic nanoemulsion.

Clause 24. The immunogenic composition of any one of clauses 1 to 20 or the pharmaceutical composition of any one of clauses 21 to 23 wherein the self-replicating RNA molecules are formulated in lipid nanoparticles (LNP) or in a cationic nanoemulsion (CNE).

Clause 25. The immunogenic composition of any one of clauses 1 to 20 or the pharmaceutical composition of any one of clauses 21 to 23 for use as a vaccine.

Clause 26. The immunogenic composition of any one of clauses 1 to 20 or the pharmaceutical composition of any one of clauses 21 to 23 for use in the prevention of influenza.

Clause 27. A method of prevention and/or treatment against influenza disease, comprising the administration of an immunogenic composition according to any one of clauses 1 to 20 or the pharmaceutical composition of any one of clauses 21 to 23 to a person in need thereof.

Clause 28. A method for inducing an immune response in a subject comprising administering to the subject an effective amount of a pharmaceutical composition according to any one of clauses 21 to 23 or the immunogenic composition of any one of clauses 1 to 20.

Clause 29. A method of prevention and/or treatment against influenza disease, comprising (i) the administration of a first immunogenic composition comprising a first self-replicating RNA molecule and pharmaceutically acceptable carrier and (ii) simultaneous or sequential administration of a second immunogenic composition comprising a second self-replicating RNA molecule and pharmaceutically acceptable carrier, wherein the first and second self-replicating RNA molecules encode a polypeptide encoding an antigen from influenza virus but the first self-replicating RNA molecule encodes an antigen from a different strain of influenza to that encoded by the second self-replicating RNA molecule.

Clause 30. A first immunogenic composition comprising a first self-replicating RNA molecule and a pharmaceutically acceptable carrier for use in a method of preventing influenza disease, said method comprising administration to a subject in need the first immunogenic composition followed by administration of a second immunogenic composition comprising a self-replicating RNA molecule and a pharmaceutically acceptable carrier, wherein the first and second self-replicating RNA molecules each encode a polypeptide comprising an antigen, wherein the antigen is from influenza virus but the antigen encoded by the first self-replicating RNA molecule is from a different strain of influenza virus to that encoded by the second self-replicating RNA molecule.

Clause 31. The immunogenic composition for use according to clause 30 wherein the first and second immunogenic compositions are administered simultaneously, at substantially the same time or sequentially.

Clause 32. The immunogenic composition for use according to clause 30 wherein the first and second immunogenic compositions are administered sequentially with an interval of less than hours, from 1 second to 10 hours or from 1 second to 1 hour.

Clause 33. A method of preparing an immunogenic composition according to any one of clauses 1 to 20 or 24, the method comprising: (i) providing an oil-in-water emulsion; (ii) providing an aqueous solution comprising the self-replicating RNA molecules; and (iii) combining the aqueous solution of (ii) and the oil-in-water emulsion of (i), thereby preparing the composition.

Clause 34. A method of preparing an immunogenic composition according to any one of clauses 1 to 20 or 24, the method comprising: (i) providing at least one lipid which forms nanoparticles; (ii) providing an aqueous solution comprising the self-replicating RNA molecules; and (iii) combining the aqueous solution of (ii) and the at least one lipid of (i), thereby preparing the composition.

Sequence Listings

```
SEQ ID NO: 1: Nucleotide cDNA sequence of A836 TC83 VEE/SINV (Venezuelan equine encephalitis-
Sindbis virus) chimeric replicon containing T7 DNA polymerase promoter
ataggcggcgcatgagagaagcccagaccaattacctacccaaaatggagaaagttcacgttgacatcgaggaagacagcccattcctcag

agctttgcagcggagcttcccgcagtttgaggtagaagccaagcaggtcactgataatgaccatgctaatgccagagcgttttcgcatctggctt

caaaactgatcgaaacggaggtggacccatccgacacgatccttgacattggaagtgcgcccgcccgcagaatgtattctaagcacaagtatc

attgtatctgtccgatgagatgtgcggaagatccggacagattgtataagtatgcaactaagctgaagaaaaactgtaaggaaataactgata

aggaattggacaagaaaatgaaggagctcgccgccgtcatgagcgaccctgacctggaaactgagactatgtgcctccacgacgacgagtc

gtgtcgctacgaagggcaagtcgctgtttaccaggatgtatacgcggttgacggaccgacaagtctctatcaccaagccaataagggagttag

agtcgcctactggataggctttgacaccaccccttttatgtttaagaacttggctggagcatatccatcatactctaccaactgggccgacgaaac

cgtgttaacggctcgtaacataggcctatgcagctctgacgttatggagcggtcacgtagagggatgtccattcttagaaagaagtatttgaaa

ccatccaacaatgttctattctctgttggctcgaccatctaccacgagaagagggacttactgaggagctggcacctgccgtctgtatttcacttac

gtggcaagcaaaattacacatgtcggtgtgagactatagttagttgcgacgggtacgtcgttaaaagaatagctatcagtccaggcctgtatgg

gaagccttcaggctatgctgctacgatgcaccgcgagggattcttgtgctgcaaagtgacagacacattgaacggggagagggtctcttttccc

gtgtgcacgtatgtgccagctacattgtgtgaccaaatgactggcatactggcaacagatgtcagtgcggacgacgcgcaaaaactgctggtt

gggctcaaccagcgtatagtcgtcaacggtcgcacccagagaaacaccaataccatgaaaaattacctttgcccgtagtggcccaggcattt

gctaggtgggcaaaggaatataaggaagatcaagaagatgaaaggccactaggactacgagatagacagttagtcatggggtgttgttgg
```

-continued gcttttagaaggcacaagataacatctatttataagcgcccggatacccaaaccatcatcaaagtgaacagcgatttccactcattcgtgctgcc caggataggcagtaacacattggagatcgggctgagaacaagaatcaggaaaatgttagaggagcacaaggagccgtcacctctcattacc gccgaggacgtacaagaagctaagtgcgcagccgatgaggctaaggaggtgcgtgaagccgaggagttgcgcgcagctctaccacctttg gcagctgatgttgaggagcccactctggaagccgatgtcgacttgatgttacaagaggctggggccggctcagtggagacacctcgtggcttg ataaaggttaccagctacgatggcgaggacaagatcggctcttacgctgtgctttctccgcaggctgtactcaagagtgaaaaattatcttgcat ccaccctctcgctgaacaagtcatagtgataacacactctggccgaaaagggcgttatgccgtggaaccataccatggtaaagtagtggtgcc agagggacatgcaatacccgtccaggactttcaagctctgagtgaaagtgccaccattgtgtacaacgaacgtgagttcgtaaacaggtacct gcaccatattgccacacatggaggagcgctgaacactgatgaagaatattacaaaactgtcaagcccagcgagcacgacggcgaatacctgt acgacatcgacaggaaacagtgcgtcaagaaagaactagtcactgggctagggctcacaggcgagctggtggatcctcccttccatgaattc gcctacgagagtctgagaacacgaccagccgctccttaccaagtaccaaccataggggtgtatggcgtgccaggatcaggcaagtctggcat cattaaaagcgcagtcaccaaaaaagatctagtggtgagcgccaagaaagaaaactgtgcagaaattataagggacgtcaagaaaatgaa agggctggacgtcaatgccagaactgtggactcagtgctcttgaatggatgcaaacaccccgtagagaccctgtatattgacgaagcttttgct tgtcatgcaggtactctcagagcgctcatagccattataagacctaaaaaggcagtgctctgcggggatcccaaacagtgcggtttttttaacat gatgtgcctgaaagtgcattttaaccacgagatttgcacacaagtcttccacaaaagcatctctcgccgttgcactaaatctgtgacttcggtcgt ctcaaccttgttttacgacaaaaaaatgagaacgacgaatccgaaagagactaagattgtgattgacactaccggcagtaccaaacctaagca ggacgatctcattctcacttgtttcagagggtgggtgaagcagttgcaaatagattacaaaggcaacgaaataatgacggcagctgcctctca agggctgacccgtaaaggtgtgtatgccgttcggtacaaggtgaatgaaaatcctctgtacgcacccacctcagaacatgtgaacgtcctactg acccgcacggaggaccgcatcgtgtggaaaacactagccggcgacccatggataaaaacactgactgccaagtaccctgggaatttcactgc cacgatagaggagtggcaagcagagcatgatgccatcatgaggcacatcttggagagaccggaccctaccgacgtcttccagaataaggca aacgtgtgttgggccaaggctttagtgccggtgctgaagaccgctggcatagacatgaccactgaacaatggaacactgtggattattttgaaa cggacaaagctcactcagcagagatagtattgaaccaactatgcgtgaggttctttggactcgatctggactccggtctattttctgcacccactg ttccgttatccattaggaataatcactgggataactccccgtcgcctaacatgtacgggctgaataaagaagtggtccgtcagctctctcgcagg tacccacaactgcctcgggcagttgccactggaagagtctatgacatgaacactggtacactgcgcaattatgatccgcgcataaacctagtac ctgtaaacagaagactgcctcatgctttagtcctccaccataatgaacacccacagagtgacttttcttcattcgtcagcaaattgaagggcaga actgtcctggtggtcggggaaaagttgtccgtcccaggcaaaatggttgactggttgtcagaccggcctgaggctaccttcagagctcggctg gatttaggcatcccaggtgatgtgcccaaatatgacataatatttgttaatgtgaggaccccatataaataccatcactatcagcagtgtgaaga ccatgccattaagcttagcatgttgaccaagaaagcttgtctgcatctgaatcccggcggaacctgtgtcagcataggttatggttacgctgaca gggccagcgaaagcatcattggtgctatagcgcggcagttcaagttttcccgggtatgcaaaccgaaatcctcacttgaagagacggaagttc tgtttgtattcattgggtacgatcgcaaggcccgtacgcacaatccttacaagctttcatcaaccttgaccaacatttatacaggttccagactcca cgaagccggatgtgcaccctcatatcatgtggtgcgaggggatattgccacggccaccgaaggagtgattataaatgctgctaacagcaaag gacaacctggcggaggggtgtgcggagcgctgtataagaaattcccggaaagcttcgatttacagccgatcgaagtaggaaaagcgcgact ggtcaaaggtgcagctaaacatatcattcatgccgtaggaccaaacttcaacaaagtttcggaggttgaaggtgacaaacagttggcagagg cttatgagtccatcgctaagattgtcaacgataacaattacaagtcagtagcgattccactgttgtccaccggcatcttttccgggaacaaagatc gactaacccaatcattgaaccatttgctgacagctttagacaccactgatgcagatgtagccatatactgcagggacaagaaatgggaaatga ctctcaaggaagcagtggctaggagagaagcagtggaggagatatgcatatccgacgactcttcagtgacagaacctgatgcagagctggt gagggtgcatccgaagagttctttggctggaaggaagggctacagcacaagcgatggcaaaactttctcatatttggaagggaccaagtttca ccaggcggccaaggatatagcagaaattaatgccatgtggcccgttgcaacggaggccaatgagcaggtatgcatgtatatcctcggagaaa gcatgagcagtattaggtcgaaatgccccgtcgaagagtcggaagcctccacaccacctagcacgctgccttgcttgtgcatccatgccatgac tccagaaagagtacagcgcctaaaagcctcacgtccagaacaaattactgtgtgctcatcctttccattgccgaagtatagaatcactggtgtgc agaagatccaatgctcccagcctatattgttctcaccgaaagtgcctgcgtatattcatccaaggaagtatctcgtggaaacaccaccggtagac -continued gagactccggagccatcggcagagaaccaatccacagaggggacacctgaacaaccaccacttataaccgaggatgagaccaggactaga acgcctgagccgatcatcatcgaagaggaagaagaggatagcataagtttgctgtcagatggcccgacccaccaggtgctgcaagtcgagg cagacattcacgggccgccctctgtatctagctcatcctggtccattcctcatgcatccgactttgatgtggacagtttatccatacttgacaccctg gagggagctagcgtgaccagcggggcaacgtcagccgagactaactcttacttcgcaaagagtatggagtttctggcgcgaccggtgcctgc gcctcgaacagtattcaggaaccctccacatcccgctccgcgcacaagaacaccgtcacttgcacccagcagggcctgctcgagaaccagcct agtttccaccccgccaggcgtgaatagggtgatcactagagaggagctcgaggcgcttaccccgtcacgcactcctagcaggtcggtctcgag aaccagcctggtctccaacccgccaggcgtaaatagggtgattacaagagaggagtttgaggcgttcgtagcacaacaacaatgacggtttg atgcgggtgcatacatcttttcctccgacaccggtcaagggcatttacaacaaaaatcagtaaggcaaacggtgctatccgaagtggtgttgga gaggaccgaattggagatttcgtatgccccgcgcctcgaccaagaaaaagaagaattactacgcaagaaattacagttaaatcccacacctg ctaacagaagcagataccagtccaggaaggtggagaacatgaaagccataacagctagacgtattctgcaaggcctagggcattatttgaa ggcagaaggaaaagtggagtgctaccgaaccctgcatcctgttcctttgtattcatctagtgtgaaccgtgccttttcaagccccaaggtcgcag tggaagcctgtaacgccatgttgaaagagaactttccgactgtggcttcttactgtattattccagagtacgatgcctatttggacatggttgacg gagcttcatgctgcttagacactgccagtttttgccctgcaaagctgcgcagctttccaaagaaacactcctatttggaacccacaatacgatcg gcagtgccttcagcgatccagaacacgctccagaacgtcctggcagctgccacaaaaagaaattgcaatgtcacgcaaatgagagaattgcc cgtattggattcggcggcctttaatgtggaatgcttcaagaaatatgcgtgtaataatgaatattgggaaacgtttaaagaaaccccatcagg cttactgaagaaaacgtggtaaattacattaccaaattaaaaggaccaaaagctgctgctctttttgcgaagacacataatttgaatatgttgca ggacataccaatggacaggtttgtaatggacttaaagagagacgtgaaagtgactccaggaacaaaacatactgaagaacggcccaaggta caggtgatccaggctgccgatccgctagcaacagcgtatctgtgcggaatccaccgagagctggttaggagattaaatgcggtcctgcttccg aacattcatacactgtttgatatgtcggctgaagactttgacgctattatagccgagcacttccagcctggggattgtgttctggaaactgacatc gcgtcgtttgataaaagtgaggacgacgccatggctctgaccgcgttaatgattctggaagacttaggtgtggacgcagagctgttgacgctg attgaggcggctttcggcgaaatttcatcaatacatttgcccactaaaactaaatttaaattcggagccatgatgaaatctggaatgttcctcaca ctgtttgtgaacacagtcattaacattgtaatcgcaagcagagtgttgagagaacggctaaccggatcaccatgtgcagcattcattggagatg acaatatcgtgaaaggagtcaaatcggacaaattaatggcagacaggtgcgccacctggttgaatatggaagtcaagattatagatgctgtg gtgggcgagaaagcgccttatttctgtggagggtttattttgtgtgactccgtgaccggcacagcgtgccgtgtggcagacccccctaaaaaggc tgtttaagcttggcaaacctctggcagcagacgatgaacatgatgatgacaggagaagggcattgcatgaagagtcaacacgctggaaccg agtgggtattctttcagagctgtgcaaggcagtagaatcaaggtatgaaaccgtaggaacttccatcatagttatggccatgactactctagcta gcagtgttaaatcattcagctacctgagaggggcccctataactctctacggctaacctgaatggactacgacatagtctagtccgccaagatg gagaaaatagtgcttcttcttgcaatagtcagccttgttaaaagtgatcagatttgcattggttaccatgcaaacaactcgacagagcaggttga cacaataatggaaaagaacgtcactgttacacacgcccaagacatactggaaaagacacacaacgggaaactctgcgatctagatggagtg aagcctctaattttaagagattgtagtgtagctggatggctcctcgggaacccaatgtgtgacgaattcctcaatgtgccggaatggtcttacata gtggagaagatcaatccagccaatgacctctgttacccagggaatttcaacgactatgaagaactgaaacacctattgagcagaataaaccat tttgagaaaattcagatcatccccaaaagttcttggtcagatcatgaagcctcagcaggggtgagctcagcatgtccataccagggaaggtcct cctttttttagaaatgtggtatggcttatcaaaaaggacaatgcatacccaacaataaagagaagttacaataataccaaccaagaagatcttttg gtattgtgggggattcaccatccaaatgatgcggcagagcagacaaggctctatcaaaacccaactacctatatttccgttgggacatcaacac taaaccagagattggtaccaaaaatagccactagatctaaggtaaacgggcaaagtggaaggatggagttcttttggacaattttaaaaccga atgatgcaataaactttgagagtaatggaaatttcattgctccagaaaatgcatacaaaattgtcaagaaaggggactcaacaattatgaaaa gtgagttggaatatggtaactgcaacaccaagtgtcaaactccaataggggcgataaactctagtatgccattccacaacatccaccctctcac catcggggaatgccccaaatatgtgaaatcaagcagattagtccttgctactgggctcagaaatagccctcaacgagagacacgaggactatt tggagctatagcaggttttatagagggaggatggcagggaatggtagatggttggtatgggtaccaccatagcaacgagcaggggagtggg tacgctgcagacaaagaatccactcaaaaggcaatagatggagtcaccaataaggtcaactcgatcattgacaaaatgaacactcagtttga ggctgttggaagggaatttaataacttagaaaggagaatagaaaatttaaacaagaagatggaagacggattcctagatgtctggacttata -continued atgctgaacttctggttctcatggaaaatgagagaactctagactttcatgactcaaatgtcaagaacctttacgacaaggtccgactacagctt agggataatgcaaaggagcttggtaacggttgtttcgagttctatcacagatgtgataatgaatgtatggaaagtgtaagaaacggaacgtat gactacccgcagtattcagaagaagcaagattaaaaagagaggaaataagtggagtaaaattggaatcaataggaacttaccaaatactgt caatttattcaacagtggcgagctccctagcactggcaatcatggtggctggtctatctttatggatgtgctccaatggatcgttacaatgcagaa tttgcatttaaggcgcgcccacccagcggccgcatacagcagcaattggcaagctgcttacatagaactcgcggcgattggcatgccgccttaa aatttttattttattttttcttttcttttccgaatcggattttgtttttaatatttcaaaaaaaaaaaaaaaaaaaaaaaaaaaaaaaaaaaaaaaaaaga agagcgtttaaacacgtgatatctggcctcatgggccttcctttcactgcccgctttccagtcgggaaacctgtcgtgccagctgcattaacatgg tcatagctgtttccttgcgtattgggcgctctccgcttcctcgctcactgactcgctgcgctcggtcgttcgggtaaagcctggggtgcctaatgag caaaaggccagcaaaaggccaggaaccgtaaaaaggccgcgttgctggcgtttttccataggctccgcccccctgacgagcatcacaaaaat cgacgctcaagtcagaggtggcgaaacccgacaggactataaagataccaggcgtttccccctggaagctccctcgtgcgctctcctgttccg accctgccgcttaccggatacctgtccgcctttctcccttcgggaagcgtggcgctttctcatagctcacgctgtaggtatctcagttcggtgtagg tcgttcgctccaagctgggctgtgtgcacgaaccccccgttcagcccgaccgctgcgccttatccggtaactatcgtcttgagtccaacccggta agacacgacttatcgccactggcagcagccactggtaacaggattagcagagcgaggtatgtaggcggtgctacagagttcttgaagtggtg gcctaactacggctacactagaagaacagtatttggtatctgcgctctgctgaagccagttaccttcggaaaaagagttggtagctcttgatccg gcaaacaaaccaccgctggtagcggtggtttttttgtttgcaagcagcagattacgcgcagaaaaaaaggatctcaagaagatcctttgatcttt tctacggggtctgacgctcagtggaacgaaaactcacgttaagggattttggtcatgaatacacggtgcctgactgcgttagcaatttaactgtg ataaactaccgcattaaagcttatcgatgataagctgtcaaacatgagaattcttagaaaaactcatcgagcatcaaatgaaactgcaatttatt catatcaggattatcaataccatatttttgaaaaagccgtttctgtaatgaaggagaaaactcaccgaggcagttccataggatggcaagatcct ggtatcggtctgcgattccgactcgtccaacatcaatacaacctattaatttcccctcgtcaaaaataaggttatcaagtgagaaatcaccatgag tgacgactgaatccggtgagaatggcaaaagcttatgcatttctttccagacttgttcaacaggccagccattacgctcgtcatcaaaatcactc gcatcaaccaaaccgttattcattcgtgattgcgcctgagcgagacgaaatacgcgatcgctgttaaaaggacaattacaaacaggaatcgaa tgcaaccggcgcaggaacactgccagcgcatcaacaatattttcacctgaatcaggatattcttctaatacctggaatgctgttttcccggggatc gcagtggtgagtaaccatgcatcatcaggagtacggataaaatgcttgatggtcggaagaggcataaattccgtcagccagtttagtctgacc atctcatctgtaacatcattggcaacgctacctttgccatgtttcagaaacaactctggcgcatcgggcttcccatacaatcgatagattgtcgcac ctgattgcccgacattatcgcgagcccatttatacccatataaatcagcatccatgttggaatttaatcgcggcctcgagcaagacgtttcccgtt gaatatggctcataacaccccttgtattactgtttatgtaagcagacagttttattgttcatgagcggatacatatttgaatgtatttagaaaaataa acaaataggggttccgcgcacatttccccgaaaagtgccacctaaattgtaagcgttaatattttgttaaaattcgcgttaaatttttgttaaatca gctcattttttaaccaataggccgaaatcggcaaaatcccttataaatcaaaagaatagaccgagatagggttgagtggccgctacagggcgc tcccattcgccattcaggctgcgcaactgttgggaagggcgtttcggtgcgggcctcttcgctattacgccagctggcgaaagggggatgtgct gcaaggcgattaagttgggtaacgccagggttttcccagtcacacgcgtaatacgactcactatag SEQ ID NO: 2: Nucleotide cDNA sequence of A836 TC83 VEE/SINV chimeric replicon without insert
ataggcggcgcatgagagaagcccagaccaattacctacccaaaatggagaaagttcacgttgacatcgaggaagacagcccattcctcag agctttgcagcggagcttcccgcagtttgaggtagaagccaagcaggtcactgataatgaccatgctaatgccagagcgttttcgcatctggctt caaaactgatcgaaacggaggtggacccatccgacacgatccttgacattggaagtgcgcccgcccgcagaatgtattctaagcacaagtatc attgtatctgtccgatgagatgtgcggaagatccggacagattgtataagtatgcaactaagctgaagaaaaactgtaaggaaataactgata aggaattggacaagaaaatgaaggagctcgccgccgtcatgagcgaccctgacctggaaactgagactatgtgcctccacgacgacgagtc gtgtcgctacgaagggcaagtcgctgtttaccaggatgtatacgcggttgacggaccgacaagtctctatcaccaagccaataagggagttag agtcgcctactggataggctttgacaccaccccttttatgtttaagaacttggctggagcatatccatcatactctaccaactgggccgacgaaac cgtgttaacggctcgtaacataggcctatgcagctctgacgttatggagcggtcacgtagagggatgtccattcttagaaagaagtatttgaaa ccatccaacaatgttctattctctgttggctcgaccatctaccacgagaagagggacttactgaggagctggcacctgccgtctgtatttcacttac gtggcaagcaaaattacacatgtcggtgtgagactatagttagttgcgacgggtacgtcgttaaaagaatagctatcagtccaggcctgtatgg -continued gaagccttcaggctatgctgctacgatgcaccgcgagggattcttgtgctgcaaagtgacagacacattgaacggggagagggtctcttttccc gtgtgcacgtatgtgccagctacattgtgtgaccaaatgactggcatactggcaacagatgtcagtgcggacgacgcgcaaaaactgctggtt gggctcaaccagcgtatagtcgtcaacggtcgcacccagagaaacaccaataccatgaaaaattaccttttgcccgtagtggcccaggcattt gctaggtgggcaaaggaatataaggaagatcaagaagatgaaaggccactaggactacgagatagacagttagtcatggggtgttgttgg gcttttagaaggcacaagataacatctatttataagcgcccggatacccaaaccatcatcaaagtgaacagcgatttccactcattcgtgctgcc caggataggcagtaacacattggagatcgggctgagaacaagaatcaggaaaatgttagaggagcacaaggagccgtcacctctcattacc gccgaggacgtacaagaagctaagtgcgcagccgatgaggctaaggaggtgcgtgaagccgaggagttgcgcgcagctctaccacctttg gcagctgatgttgaggagcccactctggaagccgatgtcgacttgatgttacaagaggctggggccggctcagtggagacacctcgtggcttg ataaaggttaccagctacgatggcgaggacaagatcggctcttacgctgtgctttctccgcaggctgtactcaagagtgaaaaattatcttgcat ccaccctctcgctgaacaagtcatagtgataacacactctggccgaaaagggcgttatgccgtggaaccataccatggtaaagtagtggtgcc agagggacatgcaatacccgtccaggactttcaagctctgagtgaaagtgccaccattgtgtacaacgaacgtgagttcgtaaacaggtacct gcaccatattgccacacatggaggagcgctgaacactgatgaagaatattacaaaactgtcaagcccagcgagcacgacggcgaatacctgt acgacatcgacaggaaacagtgcgtcaagaaagaactagtcactgggctagggctcacaggcgagctggtggatcctcccttccatgaattc gcctacgagagtctgagaacacgaccagccgctccttaccaagtaccaaccataggggtgtatggcgtgccaggatcaggcaagtctggcat cattaaaagcgcagtcaccaaaaaagatctagtggtgagcgccaagaaagaaaactgtgcagaaattataagggacgtcaagaaaatgaa agggctggacgtcaatgccagaactgtggactcagtgctcttgaatggatgcaaacaccccgtagagaccctgtatattgacgaagcttttgct tgtcatgcaggtactctcagagcgctcatagccattataagacctaaaaaggcagtgctctgcggggatcccaaacagtgcggtttttttaacat gatgtgcctgaaagtgcattttaaccacgagatttgcacacaagtcttccacaaaagcatctctcgccgttgcactaaatctgtgacttcggtcgt ctcaaccttgttttacgacaaaaaaatgagaacgacgaatccgaaagagactaagattgtgattgacactaccggcagtaccaaacctaagca ggacgatctcattctcacttgtttcagagggtgggtgaagcagttgcaaatagattacaaaggcaacgaaataatgacggcagctgcctctca agggctgacccgtaaaggtgtgtatgccgttcggtacaaggtgaatgaaaatcctctgtacgcacccacctcagaacatgtgaacgtcctactg acccgcacggaggaccgcatcgtgtggaaaacactagccggcgacccatggataaaaacactgactgccaagtaccctgggaatttcactgc cacgatagaggagtggcaagcagagcatgatgccatcatgaggcacatcttggagagaccggaccctaccgacgtcttccagaataaggca aacgtgtgttgggccaaggctttagtgccggtgctgaagaccgctggcatagacatgaccactgaacaatggaacactgtggattattttgaaa cggacaaagctcactcagcagagatagtattgaaccaactatgcgtgaggttctttggactcgatctggactccggtctattttctgcacccactg ttccgttatccattaggaataatcactgggataactccccgtcgcctaacatgtacgggctgaataaagaagtggtccgtcagctctctcgcagg tacccacaactgcctcgggcagttgccactggaagagtctatgacatgaacactggtacactgcgcaattatgatccgcgcataaacctagtac ctgtaaacagaagactgcctcatgctttagtcctccaccataatgaacacccacagagtgacttttcttcattcgtcagcaaattgaagggcaga actgtcctggtggtcggggaaaagttgtccgtcccaggcaaaatggttgactggttgtcagaccggcctgaggctaccttcagagctcggctg gatttaggcatcccaggtgatgtgcccaaatatgacataatatttgttaatgtgaggaccccatataaataccatcactatcagcagtgtgaaga ccatgccattaagcttagcatgttgaccaagaaagcttgtctgcatctgaatcccggcggaacctgtgtcagcataggttatggttacgctgaca gggccagcgaaagcatcattggtgctatagcgcggcagttcaagttttcccgggtatgcaaaccgaaatcctcacttgaagagacggaagttc tgtttgtattcattgggtacgatcgcaaggcccgtacgcacaatccttacaagctttcatcaaccttgaccaacatttatacaggttccagactcca cgaagccggatgtgcaccctcatatcatgtggtgcgaggggatattgccacggccaccgaaggagtgattataaatgctgctaacagcaaag gacaacctggcggaggggtgtgcggagcgctgtataagaaattcccggaaagcttcgatttacagccgatcgaagtaggaaaagcgcgact ggtcaaaggtgcagctaaacatatcattcatgccgtaggaccaaacttcaacaaagtttcggaggttgaaggtgacaaacagttggcagagg cttatgagtccatcgctaagattgtcaacgataacaattacaagtcagtagcgattccactgttgtccaccggcatcttttccgggaacaaagatc gactaacccaatcattgaaccatttgctgacagctttagacaccactgatgcagatgtagccatatactgcagggacaagaaatgggaaatga ctctcaaggaagcagtggctaggagagaagcagtggaggagatatgcatatccgacgactcttcagtgacagaacctgatgcagagctggt gagggtgcatccgaagagttctttggctggaaggaagggctacagcacaagcgatggcaaaactttctcatatttggaagggaccaagtttca -continued ccaggcggccaaggatatagcagaaattaatgccatgtggcccgttgcaacggaggccaatgagcaggtatgcatgtatatcctcggagaaa gcatgagcagtattaggtcgaaatgccccgtcgaagagtcggaagcctccacaccacctagcacgctgccttgcttgtgcatccatgccatgac tccagaaagagtacagcgcctaaaagcctcacgtccagaacaaattactgtgtgctcatcctttccattgccgaagtatagaatcactggtgtgc agaagatccaatgctcccagcctatattgttctcaccgaaagtgcctgcgtatattcatccaaggaagtatctcgtggaaacaccaccggtagac gagactccggagccatcggcagagaaccaatccacagaggggacacctgaacaaccaccacttataaccgaggatgagaccaggactaga acgcctgagccgatcatcatcgaagaggaagaagaggatagcataagtttgctgtcagatggcccgacccaccaggtgctgcaagtcgagg cagacattcacgggccgccctctgtatctagctcatcctggtccattcctcatgcatccgactttgatgtggacagtttatccatacttgacaccctg gagggagctagcgtgaccagcggggcaacgtcagccgagactaactcttacttcgcaaagagtatggagtttctggcgcgaccggtgcctgc gcctcgaacagtattcaggaaccctccacatcccgctccgcgcacaagaacaccgtcacttgcacccagcagggcctgctcgagaaccagcct agtttccaccccgccaggcgtgaatagggtgatcactagagaggagctcgaggcgcttaccccgtcacgcactcctagcaggtcggtctcgag aaccagcctggtctccaacccgccaggcgtaaatagggtgattacaagagaggagtttgaggcgttcgtagcacaacaacaatgacggtttg atgcgggtgcatacatcttttcctccgacaccggtcaagggcatttacaacaaaaatcagtaaggcaaacggtgctatccgaagtggtgttgga gaggaccgaattggagatttcgtatgccccgcgcctcgaccaagaaaaagaagaattactacgcaagaaattacagttaaatcccacacctg ctaacagaagcagataccagtccaggaaggtggagaacatgaaagccataacagctagacgtattctgcaaggcctagggcattatttgaa ggcagaaggaaaagtggagtgctaccgaaccctgcatcctgttcctttgtattcatctagtgtgaaccgtgccttttcaagccccaaggtcgcag tggaagcctgtaacgccatgttgaaagagaactttccgactgtggcttcttactgtattattccagagtacgatgcctatttggacatggttgacg gagcttcatgctgcttagacactgccagtttttgccctgcaaagctgcgcagctttccaaagaaacactcctatttggaacccacaatacgatcg gcagtgccttcagcgatccagaacacgctccagaacgtcctggcagctgccacaaaaagaaattgcaatgtcacgcaaatgagagaattgcc cgtattggattcggcggcctttaatgtggaatgcttcaagaaatatgcgtgtaataatgaatattgggaaacgtttaaagaaaaccccatcagg cttactgaagaaaacgtggtaaattacattaccaaattaaaaggaccaaaagctgctgctctttttgcgaagacacataatttgaatatgttgca ggacataccaatggacaggtttgtaatggacttaaagagagacgtgaaagtgactccaggaacaaaacatactgaagaacggcccaaggta caggtgatccaggctgccgatccgctagcaacagcgtatctgtgcggaatccaccgagagctggttaggagattaaatgcggtcctgcttccg aacattcatacactgtttgatatgtcggctgaagactttgacgctattatagccgagcacttccagcctggggattgtgttctggaaactgacatc gcgtcgtttgataaaagtgaggacgacgccatggctctgaccgcgttaatgattctggaagacttaggtgtggacgcagagctgttgacgctg attgaggcggctttcggcgaaatttcatcaatacatttgcccactaaaactaaatttaaattcggagccatgatgaaatctggaatgttcctcaca ctgtttgtgaacacagtcattaacattgtaatcgcaagcagagtgttgagagaacggctaaccggatcaccatgtgcagcattcattggagatg acaatatcgtgaaaggagtcaaatcggacaaattaatggcagacaggtgcgccacctggttgaatatggaagtcaagattatagatgctgtg gtgggcgagaaagcgccttatttctgtggagggtttattttgtgtgactccgtgaccggcacagcgtgccgtgtggcagacccccctaaaaaggc tgtttaagcttggcaaacctctggcagcagacgatgaacatgatgatgacaggagaagggcattgcatgaagagtcaacacgctggaaccg agtgggtattctttcagagctgtgcaaggcagtagaatcaaggtatgaaaccgtaggaacttccatcatagttatggccatgactactctagcta gcagtgttaaatcattcagctacctgagaggggcccctataactctctacggctaacctgaatggactacgacatagtctagtccgccaagggc gcgcccacccagcggccgcatacagcagcaattggcaagctgcttacatagaactcgcggcgattggcatgccgccttaaaatttttattttattt ttcttttcttttccgaatcggatttgtttttaatatttcaaaaaaaaaaaaaaaaaaaaaaaaaaaaaaaaaaaaaaaaagaagagcgtttaaac acgtgatatctggcctcatgggccttcctttcactgcccgctttccagtcgggaaacctgtcgtgccagctgcattaacatggtcatagctgtttcct tgcgtattgggcgctctccgcttcctcgctcactgactcgctgcgctcggtcgttcgggtaaagcctggggtgcctaatgagcaaaaggccagc aaaaggccaggaaccgtaaaaaggccgcgttgctggcgtttttccataggctccgcccccctgacgagcatcacaaaaatcgacgctcaagtc agaggtggcgaaacccgacaggactataaagataccaggcgtttccccctggaagctccctcgtgcgctctcctgttccgaccctgccgcttac cggatacctgtccgcctttctcccttcgggaagcgtggcgctttctcatagctcacgctgtaggtatctcagttcggtgtaggtcgttcgctccaag ctgggctgtgtgcacgaaccccccgttcagcccgaccgctgcgccttatccggtaactatcgtcttgagtccaacccggtaagacacgacttatc gccactggcagcagccactggtaacaggattagcagagcgaggtatgtaggcggtgctacagagttcttgaagtggtggcctaactacggct acactagaagaacagtatttggtatctgcgctctgctgaagccagttaccttcggaaaaagagttggtagctcttgatccggcaaacaaaccac -continued cgctggtagcggtggtttttttgtttgcaagcagcagattacgcgcagaaaaaaaggatctcaagaagatcctttgatcttttctacggggtctga cgctcagtggaacgaaaactcacgttaagggattttggtcatgaatacacggtgcctgactgcgttagcaatttaactgtgataaactaccgcat taaagcttatcgatgataagctgtcaaacatgagaattcttagaaaaactcatcgagcatcaaatgaaactgcaatttattcatatcaggattatc aataccatatttttgaaaaagccgtttctgtaatgaaggagaaaactcaccgaggcagttccataggatggcaagatcctggtatcggtctgcg attccgactcgtccaacatcaatacaacctattaatttcccctcgtcaaaaataaggttatcaagtgagaaatcaccatgagtgacgactgaatc cggtgagaatggcaaaagcttatgcatttctttccagacttgttcaacaggccagccattacgctcgtcatcaaaatcactcgcatcaaccaaac cgttattcattcgtgattgcgcctgagcgagacgaaatacgcgatcgctgttaaaaggacaattacaaacaggaatcgaatgcaaccggcgca ggaacactgccagcgcatcaacaatattttcacctgaatcaggatattcttctaatacctggaatgctgttttcccggggatcgcagtggtgagta accatgcatcatcaggagtacggataaaatgcttgatggtcggaagaggcataaattccgtcagccagtttagtctgaccatctcatctgtaaca tcattggcaacgctacctttgccatgtttcagaaacaactctggcgcatcgggcttcccatacaatcgatagattgtcgcacctgattgcccgaca ttatcgcgagcccatttatacccatataaatcagcatccatgttggaatttaatcgcggcctcgagcaagacgtttcccgttgaatatggctcataa caccccttgtattactgtttatgtaagcagacagttttattgttcatgagcggatacatatttgaatgtatttagaaaaataaacaaataggggttc cgcgcacatttccccgaaaagtgccacctaaattgtaagcgttaatattttgttaaaattcgcgttaaatttttgttaaatcagctcattttttaacca ataggccgaaatcggcaaaatcccttataaatcaaaagaatagaccgagatagggttgagtggccgctacagggcgctcccattcgccattca ggctgcgcaactgttgggaagggcgtttcggtgcgggcctcttcgctattacgccagctggcgaaaggggggatgtgctgcaaggcgattaagt tgggtaacgccagggttttcccagtcacacgcgtaatacgactcactatag SEQ ID NO: 3: nucleotide cDNA sequence of hemagglutinin (HA) from influenza virus A/California/07/2009 (H1N1)
atgaaggcaatactagtagttctgctatatacatttgcaaccgcaaatgcagacacattatgtataggttatcatgcgaacaattcaacagacac tgtagacacagtactagaaaagaatgtaacagtaacacactctgttaaccttctagaagacaagcataacgggaaactatgcaaactaagag gggtagccccattgcatttgggtaaatgtaacattgctggctggatcctgggaaatccagagtgtgaatcactctccacagcaagctcatggtcc tacattgtggaaacacctagttcagacaatggaacgtgttacccaggagatttcatcgattatgaggagctaagagagcaattgagctcagtgt catcatttgaaaggtttgagatattccccaagacaagttcatggcccaatcatgactcgaacaaaggtgtaacggcagcatgtcctcatgctgg agcaaaaagcttctacaaaaatttaatatggctagttaaaaaaggaaattcatacccaaagctcagcaaatcctacattaatgataaagggaa agaagtcctcgtgctatggggcattcaccatccatctactagtgctgaccaacaaagtctctatcagaatgcagatgcatatgtttttgtggggtc atcaagatacagcaagacgttcaagccggaaatagcaataagacccaaagtgagggatcgagaagggagaatgaactattactggacact agtagagccgggagacaaaataacattcgaagcaactggaaatctagtggtaccgagatatgcattcgcaatggaaagaaatgctggatct ggtattatcatttcagatacaccagtccacgattgcaatacaacttgtcaaacacccaagggtgctataaacaccagcctcccatttcagaatata catccgatcacaattggaaaatgtccaaaatatgtaaaaagcacaaaattgagactggccacaggattgaggaatatcccgtctattcaatcta gaggcctatttggggccattgccggtttcattgaagggggtggacagggatggtagatggatggtacggttatcaccatcaaaatgagcag gggtcaggatatgcagccgacctgaagagcacacagaatgccattgacgagattactaacaaagtaaattctgttattgaaaagatgaatac acagttcacagcagtaggtaaagagttcaaccacctggaaaaaagaatagagaatttaaataaaaaagttgatgatggtttcctggacatttg gacttacaatgccgaactgttggttctattggaaaatgaaagaactttggactaccacgattcaaatgtgaagaacttatatgaaaaggtaaga agccagctaaaaaacaatgccaaggaaattggaaacggctgctttgaattttaccacaaatgcgataacacgtgcatggaaagtgtcaaaaa tgggacttatgactacccaaaatactcagaggaagcaaaattaaacagagaagaaatagatggggtaaagctggaatcaacaaggatttac cagattttggcgatctattcaactgtcgccagttcattggtactggtagtctccctgggggcaatcagtttctggatgtgctctaatgggtctctaca gtgtagaatatgtatttgataa SEQ ID NO: 4: amino acid sequence of HA from influenza virus A/California/07/2009 (H1N1)
MKAILVVLLYTFATANADTLCIGYHANNSTDTVDTVLEKNVTVTHSVNLLEDKHNGKLCKLRGVAPLHLGKCNIA

GWILGNPECESLSTASSWSYIVETPSSDNGTCYPGDFIDYEELREQLSSVSSFERFEIFPKTSSWPNHDSNKGVT

AACPHAGAKSFYKNLIWLVKKGNSYPKLSKSYINDKGKEVLVLWGIHHPSTSADQQSLYQNADAYVFVGSSRYS

KTFKPEIAIRPKVRDREGRMNYYWTLVEPGDKITFEATGNLVVPRYAFAMERNAGSGIIISDTPVHDCNTTCQTP

-continued

KGAINTSLPFQNIHPITIGKCPKYVKSTKLRLATGLRNIPSIQSRGLFGAIAGFIEGGWTGMVDGWYGYHHQNEQ

GSGYAADLKSTQNAIDEITNKVNSVIEKMNTQFTAVGKEFNHLEKRIENLNKKVDDGFLDIWTYNAELLVLLENE

RTLDYHDSNVKNLYEKVRSQLKNNAKEIGNGCFEFYHKCDNTCMESVKNGTYDYPKYSEEAKLNREEIDGVKLE

STRIYQILAIYSTVASSLVLVVSLGAISFWMCSNGSLQCRICI

SEQ ID NO: 5: nucleotide DNA sequence of HA from influenza virus A/PR/8/34 (H1N1)
ATGAAGGCAAACCTACTGGTCCTGTTATGTGCACTTGCAGCTGCAGATGCAGACACAATATGTATAGGCTAC

CATACGAACAATTCAACCGACACTGTTGACACAGTACTCGAGAAGAATGTGACAGTGACACACTCTGTTAACC

TGCTCGAAGACAGCCACAACGGAAAACTATGTAGATTAAAAGGAATAGCCCCACTACAATTGGGGAAATGTA

ACATCGCCGGATGGCTCTTGGGAAACCCAGAATGCGACCCACTGCTTCCAGTGAGATCATGGTCCTACATTG

TAGAAACACCAAACTCTGAGAATGGAATATGTTATCCAGGAGATTTCATCGACTATGAGGAGCTGAGGGAGC

AATTGAGCTCAGTGTCATCATTCGAAAGATTCGAAATATTTCCCAAAGAAAGCTCATGGCCCAACCACAACAC

AAACGGAGTAACGGCAGCATGCTCCCATGAGGGGAAAAGCAGTTTTTACAGAAATTTGCTATGGCTGACGGA

GAAGGAGGGCTCATACCCAAAGCTGAAAAATTCTTATGTGAACAAAAAAGGGAAAGAAGTCCTTGTACTGTG

GGGTATTCATCACCCGCCTAACAGTAAGGAACAACAGAATCTCTATCAGAATGAAAATGCTTATGTCTCTGTA

GTGACTTCAAATTATAACAGGAGATTTACCCCGGAAATAGCAGAAAGACCCAAAGTAAGAGATCAAGCTGGG

AGGATGAACTATTACTGGACCTTGCTAAAACCCGGAGACACAATAATATTTGAGGCAAATGGAAATCTAATAG

CACCAATGTATGCTTTCGCACTGAGTAGAGGCTTTGGGTCCGGCATCATCACCTCAAACGCATCAATGCATG

AGTGTAACACGAAGTGTCAAACACCCCTGGGAGCTATAAACAGCAGTCTCCCTTACCAGAATATACACCCAGT

CACAATAGGAGAGTGCCCAAAATACGTCAGGAGTGCCAAATTGAGGATGGTTACAGGACTAAGGAACATTCC

GTCCATTCAATCCAGAGGTCTATTTGGAGCCATTGCCGGTTTTATTGAAGGGGGATGGACTGGAATGATAGA

TGGATGGTATGGTTATCATCATCAGAATGAACAGGGATCAGGCTATGCAGCGGATCAAAAAAGCACACAAAA

TGCCATTAACGGGATTACAAACAAGGTGAACACTGTTATCGAGAAAATGAACATTCAATTCACAGCTGTGGG

TAAAGAATTCAACAAATTAGAAAAAAGGATGGAAAATTTAAATAAAAAAGTTGATGATGGATTTCTGGACATT

TGGACATATAATGCAGAATTGTTAGTTCTACTGGAAAATGAAAGGACTCTGGAATTCCATGACTCAAATGTGA

AGAATCTGTATGAGAAAGTAAAAAGCCAATTAAAGAATAATGCCAAAGAAATCGGAAATGGATGTTTTGAGT

TCTACCACAAGTGTGACAATGAATGCATGGAAAGTGTAAGAAATGGGACTTATGATTATCCCAAATATTCAGA

AGAGTCAAAGTTGAACAGGGAAAAGGTAGATGGAGTGAAATTGGAATCAATGGGGATCTATCAGATTCTGGC

GATCTACTCAACTGTCGCCAGTTCACTGGTGCTTTTGGTCTCCCTGGGGGCAATCAGTTTCTGGATGTGTTC

TAATGGATCTTTGCAGTGCAGAATATGCATCTGATAA

SEQ ID NO: 6: amino acid sequence of HA from influenza virus A/PR/8/34 (H1N1)
MKANLLVLLCALAAADADTICIGYHTNNSTDTVDTVLEKNVTVTHSVNLLEDSHNGKLCRLKGIAPLQLGKCNIA

GWLLGNPECDPLLPVRSWSYIVETPNSENGICYPGDFIDYEELREQLSSVSSFERFEIFPKESSWPNHNTNGVTA

ACSHEGKSSFYRNLLWLTEKEGSYPKLKNSYVNKKGKEVLVLWGIHHPPNSKEQQNLYQNENAYVSVVTSNYNR

RFTPEIAERPKVRDQAGRMNYYWTLLKPGDTIIFEANGNLIAPMYAFALSRGFGSGIITSNASMHECNTKCQTPL

GAINSSLPYQNIHPVTIGECPKYVRSAKLRMVTGLRNIPSIQSRGLFGAIAGFIEGGWTGMIDGWYGYHHQNEQ

GSGYAADQKSTQNAINGITNKVNTVIEKMNIQFTAVGKEFNKLEKRMENLNKKVDDGFLDIWTYNAELLVLLEN

ERTLEFHDSNVKNLYEKVKSQLKNNAKEIGNGCFEFYHKCDNECMESVRNGTYDYPKYSEESKLNREKVDGVKL

ESMGIYQILAIYSTVASSLVLLVSLGAISFWMCSNGSLQCRICI

SEQ ID NO: 7: nucleotide cDNA sequence of HA from influenza virus A/Bilthoven/16398/1968 (H3N2)
GGGCCCCTATAACTCTCTACGGCTAACCTGAATGGACTACGACATAGTCTAGTCCGCCAAGATGAAGACCAT

CATTGCCCTGAGCTACATCTTCTGCCTGGCCCTGGGACAGGACCTGCCCGGCAACGACAATAGCACCGCCAC

CCTGTGTCTGGGCCACCACGCCGTGCCTAACGGCACCCTGGTGAAAACCATCACCGACGACCAGATCGAAGT

-continued

GACCAACGCCACCGAGCTGGTGCAGAGCAGCAGCACCGGCAAGATCTGCAACAACCCCCACCGGATCCTGGA

CGGCATCAACTGCACCCTGATCGACGCCCTGCTGGGCGACCCCCACTGCGACGTGTTCCAGGACGAGACATG

GGACCTGTTCGTGGAAAGAAGCAAGGCCTTCAGCAACTGCTACCCCTACGACGTGCCCGACTACGCCAGCCT

GAGAAGCCTGGTGGCCAGCAGCGGCACACTGGAATTCATCACCGAGGGCTTCACCTGGACCGGCGTGACCC

AGAACGGCGGCAGCAACGCCTGCAAGAGAGGCCCTGGCAGCGGCTTCTTCAGCAGACTGAACTGGCTGACC

AAGAGCGGCAGCACCTACCCCGTGCTGAACGTGACCATGCCCAACAACGACAACTTCGACAAGCTGTACATC

TGGGGCGTGCACCACCCCAGCACCAACCAGGAACAGACCAGCCTGTACGTGCAGGCCAGCGGCAGAGTGAC

CGTGTCCACCAGAAGAAGCCAGCAGACCATCATCCCCAACATCGGCAGCAGACCCTGGGTCCGCGGCCTGAG

CAGCCGGATCAGCATCTACTGGACCATCGTGAAGCCCGGCGACGTGCTGGTGATCAACAGCAACGGCAACCT

GATCGCCCCCAGAGGCTACTTCAAGATGCGGACCGGCAAGAGCAGCATCATGCGGAGCGACGCCCCCATCGA

TACCTGCATCAGCGAGTGCATCACCCCCAACGGCAGCATCCCCAACGACAAGCCCTTCCAGAACGTGAACAA

GATCACCTACGGCGCCTGCCCCAAATACGTGAAGCAGAACACCCTGAAGCTGGCCACCGGCATGCGGAACGT

GCCCGAGAAGCAGACCAGAGGCCTGTTCGGCGCCATTGCCGGCTTCATCGAGAACGGCTGGGAGGGCATGA

TCGACGGTTGGTACGGCTTCCGGCACCAGAACAGCGAGGGCACAGGACAGGCCGCCGACCTGAAGTCTACC

CAGGCCGCCATCGACCAGATCAACGGCAAGCTGAACAGAGTGATCGAAAAGACCAACGAGAAGTTCCACCAG

ATCGAGAAAGAATTCAGCGAGGTGGAAGGCCGGATCCAGGACCTGGAAAAGTACGTGGAAGATACCAAGAT

CGACCTGTGGTCCTACAACGCCGAGCTGCTGGTGGCCCTGGAAAACCAGCACACCATCGACCTGACCGACAG

CGAGATGAACAAGCTGTTCGAGAAAACCAGACGGCAGCTGCGCGAGAACGCCGAGGACATGGGCAACGGCT

GCTTCAAGATCTACCACAAGTGCGACAATGCCTGCATCGAGAGCATCCGGAACGGCACCTACGACCACGACG

TGTACAGGGACGAGGCCCTGAACAACCGGTTCCAGATCAAGGGCGTGGAACTGAAGTCCGGCTACAAGGAC

TGGATCCTGTGGATCAGCTTCGCCATCAGCTGCTTTCTGCTGTGCGTGGTGCTGCTGGGCTTCATCATGTGG

GCCTGCCAGCGGGGCAACATCCGGTGCAACATCTGCATTTAAGGCGCGCCCACCCAGCGGCCGC

SEQ ID NO: 8: amino acid sequence of HA from influenza virus A/Bilthoven/16398/1968 (H3N2)
MKTIIALSYIFCLALGQDLPGNDNSTATLCLGHHAVPNGTLVKTITDDQIEVTNATELVQSSSTGKICNNPHRILD

GINCTLIDALLGDPHCDVFQDETWDLFVERSKAFSNCYPYDVPDYASLRSLVASSGTLEFITEGFTWTGVTQNG

GSNACKRGPGSGFFSRLNWLTKSGSTYPVLNVTMPNNDNFDKLYIWGVHHPSTNQEQTSLYVQASGRVTVSTR

RSQQTIIPNIGSRPWVRGLSSRISIYWTIVKPGDVLVINSNGNLIAPRGYFKMRTGKSSIMRSDAPIDTCISECITP

NGSIPNDKPFQNVNKITYGACPKYVKQNTLKLATGMRNVPEKQTRGLFGAIAGFIENGWEGMIDGWYGFRHQN

SEGTGQAADLKSTQAAIDQINGKLNRVIEKTNEKFHQIEKEFSEVEGRIQDLEKYVEDTKIDLWSYNAELLVALEN

QHTIDLTDSEMNKLFEKTRRQLRENAEDMGNGCFKIYHKCDNACIESIRNGTYDHDVYRDEALNNRFQIKGVEL

KSGYKDWILWISFAISCFLLCVVLLGFIMWACQRGNIRCNICI

SEQ ID NO: 9: nucleotide cDNA sequence of HA from influenza virus A/Bangkok/1/79 (H3N2)
GGGCCCCTATAACTCTCTACGGCTAACCTGAATGGACTACGACATAGTCTAGTCCGCCAAGATGAAGACCAT

CATTGCCCTGAGCTACATCTTCTGCCTGGTGTTCGCCCAGAACCTGCCCGGCAACGACAATAGCACCGCCAC

CCTGTGTCTGGGCCACCACGCCGTGCCTAACGGCACCCTGGTGAAAACCATCACCAACGACCAGATCGAAGT

GACCAACGCCACCGAGCTGGTGCAGAGCAGCAGCACCGGCAGAATCTGCGACAGCCCCCACCGGATCCTGGA

CGGCAAGAACTGCACCCTGATCGACGCCCTGCTGGGCGACCCCCACTGCGACGGCTTCCAGAACGAGAAGTG

GGACCTGTTCGTGGAAAGAAGCAAGGCCTTCAGCAACTGCTACCCCTACGACGTGCCCGACTACGCCAGCCT

GAGAAGCCTGGTGGCCAGCAGCGGCACACTGGAATTCATCAACGAGGGCTTCAACTGGACCGGCGTGACCC

AGAGCGGCGGCAGCTATGCCTGCAAGAGAGGCAGCGACAAGAGCTTCTTCAGCAGACTGAACTGGCTGTAC

GAGAGCGAGAGCAAGTACCCCGTGCTGAACGTGACCATGCCCAACAACGGCAACTTCGACAAGCTGTACATC

-continued

TGGGGCGTGCACCACCCCAGCACCGACAAAGAACAGACCAACCTGTACGTGCGGGCCAGCGGCAGAGTGAC

CGTGTCCACCAAGAGAAGCCAGCAGACCATCATCCCCAACATCGGCAGCAGACCCTGGGTCCGCGGCCTGAG

CAGCGGCATCAGCATCTACTGGACCATCGTGAAGCCCGGCGACATCCTGCTGATCAACAGCAACGGCAACCT

GATCGCCCCCAGAGGCTACTTCAAGATCCGGACCGGCAAGAGCAGCATCATGCGGAGCGACGCCCCCATCGG

GACCTGCAGCAGCGAGTGCATCACCCCCAACGGCAGCATCCCCAACGACAAGCCCTTCCAGAACGTGAACAA

GATCACCTACGGCGCCTGCCCCAAATACGTGAAGCAGAACACCCTGAAGCTGGCCACCGGCATGCGGAACGT

GCCCGAGAAGCAGACCAGAGGCATCTTCGGCGCCATTGCCGGCTTCATCGAGAACGGCTGGGAGGGCATGG

TGGACGGTTGGTACGGCTTCCGGCACCAGAACAGCGAGGGCACAGGACAGGCCGCCGACCTGAAGTCTACC

CAGGCCGCCATCGACCAGATCAACGGCAAGCTGAACAGAGTGATCGAAAAGACCAACGAGAAGTTCCACCAG

ATCGAGAAAGAATTCAGCGAGGTGGAAGGCCGGATCCAGGACCTGGAAAAGTACGTGGAAGATACCAAGAT

CGACCTGTGGTCCTACAACGCCGAGCTGCTGGTGGCCCTGGAAAACCAGCACACCATCGACCTGACCGACAG

CGAGATGAACAAGCTGTTCGAGAAAACCAGACGGCAGCTGCGCGAGAACGCCGAGGACATGGGCAACGGCT

GCTTCAAGATCTACCACAAGTGCGACAATGCCTGCATCGGCAGCATCCGGAACGGCACCTACGACCACGACG

TGTACAGGGACGAGGCCCTGAACAACCGGTTCCAGATCAAGGGCGTGGAACTGAAGTCCGGCTACAAGGAC

TGGATCCTGTGGATCAGCTTCGCCATCAGCTGCTTTCTGCTGTGCGTGGTGCTGCTGGGCTTCATCATGTGG

GCCTGCCAGAAAGGCAACATCCGGTGCAACATCTGCATTTAAGGCGCGCCCACCCAGCGGCCGC

SEQ ID NO: 10: amino acid sequence of HA from influenza virus A/Bangkok/1/79 (H3N2)
MKTIIALSYIFCLVFAQNLPGNDNSTATLCLGHHAVPNGTLVKTITNDQIEVTNATELVQSSSTGRICDSPHRILD

GKNCTLIDALLGDPHCDGFQNEKWDLFVERSKAFSNCYPYDVPDYASLRSLVASSGTLEFINEGFNWTGVTQSG

GSYACKRGSDKSFFSRLNWLYESESKYPVLNVTMPNNGNFDKLYIWGVHHPSTDKEQTNLYVRASGRVTVSTK

RSQQTIIPNIGSRPWVRGLSSGISIYWTIVKPGDILLINSNGNLIAPRGYFKIRTGKSSIMRSDAPIGTCSSECITPN

GSIPNDKPFQNVNKITYGACPKYVKQNTLKLATGMRNVPEKQTRGIFGAIAGFIENGWEGMVDGWYGFRHQNS

EGTGQAADLKSTQAAIDQINGKLNRVIEKTNEKFHQIEKEFSEVEGRIQDLEKYVEDTKIDLWSYNAELLVALEN

QHTIDLTDSEMNKLFEKTRRQLRENAEDMGNGCFKIYHKCDNACIGSIRNGTYDHDVYRDEALNNRFQIKGVEL

KSGYKDWILWISFAISCFLLCVVLLGFIMWACQKGNIRCNICI

SEQ ID NO: 11: nucleotide cDNA sequence of HA from influenza virus A/Beijing/32/92 (H3N2)
GGGCCCCTATAACTCTCTACGGCTAACCTGAATGGACTACGACATAGTCTAGTCCGCCAAGATGAAGACCAT

CATTGCCCTGAGCTACATCCTGTGCCTGGTGTTCGCCCAGAAGCTGCCCGGCAACGACAATAGCACCGCCAC

CCTGTGTCTGGGCCACCACGCCGTGCCTAACGGCACCCTGGTGAAAACCATCACCAACGACCAGATCGAAGT

GACCAACGCCACCGAGCTGGTGCAGAGCAGCAGCACCGGCAGAATCTGCGACAGCCCCCACCGGATCCTGGA

CGGCAAGAACTGCACCCTGATCGACGCCCTGCTGGGCGACCCCCACTGCGACGGCTTCCAGAACAAAGAGTG

GGACCTGTTCGTGGAAAGAAGCAAGGCCTACAGCAACTGCTACCCCTACGACGTGCCCGACTACGCCAGCCT

GAGAAGCCTGGTGGCCAGCAGCGGCACACTGGAATTCATCAACGAGGACTTCAACTGGACCGGCGTGGCCC

AGGATGGCGGCAGCTATGCCTGCAAGAGAGGCAGCGTGAACAGCTTCTTCAGCAGACTGAACTGGCTGCACA

AGAGCGAGTACAAGTACCCCGCCCTGAACGTGACCATGCCCAACAACGGCAAGTTCGACAAGCTGTACATCT

GGGGCGTGCACCACCCCAGCACCGACAGGGACCAGACCAGCCTGTACGTGCGGGCCAGCGGCAGAGTGACC

GTGTCCACCAAGAGAAGCCAGCAGACCGTGACCCCCAACATCGGCAGCAGACCCTGGGTCCGCGGCCAGAGC

AGCCGGATCAGCATCTACTGGACCATCGTGAAGCCCGGCGACATCCTGCTGATCAACAGCACAGGCAACCTG

ATCGCCCCCAGAGGCTACTTCAAGATCCGGAACGGCAAGAGCAGCATCATGCGGAGCGACGCCCCCATCGGG

ACCTGCAGCAGCGAGTGCATCACCCCCAACGGCAGCATCCCCAACGACAAGCCCTTCCAGAACGTGAACCGG

ATCACCTACGGCGCCTGCCCCAGATACGTGAAGCAGAACACCCTGAAGCTGGCCACCGGCATGCGGAACGTG

CCCGAGAAGCAGACCAGAGGCATCTTCGGCGCCATTGCCGGCTTCATCGAGAACGGCTGGGAGGGCATGGT

-continued

GGACGGTTGGTACGGCTTCCGGCACCAGAACAGCGAGGGCACAGGACAGGCCGCCGACCTGAAGTCTACCC

AGGCCGCCATCGACCAGATCAACGGCAAGCTGAACAGACTGATCGAAAAGACCAACGAGAAGTTCCACCAGA

TCGAGAAAGAATTCAGCGAGGTGGAAGGCCGGATCCAGGACCTGGAAAAGTACGTGGAAGATACCAAGATC

GACCTGTGGTCCTACAACGCCGAGCTGCTGGTGGCCCTGGAAAACCAGCACACCATCGACCTGACCGACAGC

GAGATGAACAAGCTGTTCGAGAAAACCAGAAAGCAGCTGCGCGAGAACGCCGAGGACATGGGCAACGGCTG

CTTCAAGATCTACCACAAGTGCGACAATGCCTGCATCGGCAGCATCCGGAACGGCACCTACGACCACGACGT

GTACAGGGACGAGGCCCTGAACAACCGGTTCCAGATCAAGGGCGTGGAACTGAAGTCCGGCTACAAGGACT

GGATCCTGTGGATCAGCTTCGCCATCAGCTGCTTTCTGCTGTGCGTGGTGCTGCTGGGCTTCATCATGTGGG

CCTGCCAGAAAGGCAACATCCGGTGCAACATCTGCATTTAAGGCGCGCCCACCCAGCGGCCGC

SEQ ID NO: 12: amino acid sequence of HA from influenza virus A/Beijing/32/92 (H3N2)
MKTIIALSYILCLVFAQKLPGNDNSTATLCLGHHAVPNGTLVKTITNDQIEVTNATELVQSSSTGRICDSPHRILD

GKNCTLIDALLGDPHCDGFQNKEWDLFVERSKAYSNCYPYDVPDYASLRSLVASSGTLEFINEDFNWTGVAQDG

GSYACKRGSVNSFFSRLNWLHKSEYKYPALNVTMPNNGKFDKLYIWGVHHPSTDRDQTSLYVRASGRVTVSTK

RSQQTVTPNIGSRPWVRGQSSRISIYWTIVKPGDILLINSTGNLIAPRGYFKIRNGKSSIMRSDAPIGTCSSECITP

NGSIPNDKPFQNVNRITYGACPRYVKQNTLKLATGMRNVPEKQTRGIFGAIAGFIENGWEGMVDGWYGFRHQN

SEGTGQAADLKSTQAAIDQINGKLNRLIEKTNEKFHQIEKEFSEVEGRIQDLEKYVEDTKIDLWSYNAELLVALEN

QHTIDLTDSEMNKLFEKTRKQLRENAEDMGNGCFKIYHKCDNACIGSIRNGTYDHDVYRDEALNNRFQIKGVEL

KSGYKDWILWISFAISCFLLCVVLLGFIMWACQKGNIRCNICI

SEQ ID NO: 13: nucleotide cDNA sequence of HA from influenza virus A/Fujain/411/2002 (H3N2)
GGGCCCCTATAACTCTCTACGGCTAACCTGAATGGACTACGACATAGTCTAGTCCGCCAAGATGAAGACCAT

CATTGCCCTGAGCTACATCCTGTGCCTGGTGTTCGCCCAGAAGCTGCCCGGCAACGACAATAGCACCGCCAC

CCTGTGTCTGGGCCACCACGCCGTGCCTAACGGCACCATCGTGAAAACCATCACCAACGACCAGATCGAAGT

GACCAACGCCACCGAGCTGGTGCAGAGCAGCAGCACCGGCGGCATCTGCGACAGCCCCCACCAGATCCTGGA

CGGCGAGAACTGCACCCTGATCGACGCCCTGCTGGGCGACCCCCAGTGCGACGGCTTCCAGAACAAGAAATG

GGACCTGTTCGTGGAAAGAAGCAAGGCCTACAGCAACTGCTACCCCTACGACGTGCCCGACTACGCCAGCCT

GAGAAGCCTGGTGGCCAGCAGCGGCACACTGGAATTCAACAACGAGAGCTTCAACTGGACCGGCGTGACCCA

GAACGGCACCAGCAGCGCCTGCAAGAGAAGAAGCAACAAGAGCTTCTTCAGCAGACTGAACTGGCTGACCCA

CCTGAAGTACAAGTACCCCGCCCTGAACGTGACCATGCCCAACAACGAAAAGTTCGACAAGCTGTACATCTG

GGGCGTGCTGCACCCCGGCACCGACAGCGACCAGATCAGCCTGTACGCCCAGGCCAGCGGCAGAATCACCG

TGTCCACCAAGAGAAGCCAGCAGACCGTGATCCCCAACATCGGCAGCAGACCCAGAGTCCGCGGCGTGAGCA

GCCGGATCAGCATCTACTGGACCATCGTGAAGCCCGGCGACATCCTGCTGATCAACAGCACCGGCAACCTGA

TCGCCCCCAGAGGCTACTTCAAGATTCGGAGCGGCAAGAGCAGCATCATGCGGAGCGACGCCCCCATCGGCA

AGTGCAACAGCGAGTGCATCACCCCCAACGGCAGCATCCCCAACGACAAGCCCTTCCAGAACGTGAACCGGA

TCACCTACGGCGCCTGCCCCCGGTACATCAAGCAGAACACCCTGAAGCTGGCCACCGGCATGCGGAACGTGC

CCGAGAAGCAGACCAGAGGCATCTTCGGCGCCATTGCCGGCTTCATCGAGAACGGCTGGGAGGGCATGGTG

GACGGTTGGTACGGCTTCCGGCACCAGAACAGCGAGGGCACAGGACAGGCCGCCGACCTGAAGTCTACCCA

GGCCGCCATCAACCAGATCAACGGCAAGCTGAACAGACTGATCGGCAAGACCAACGAGAAGTTCCACCAGAT

CGAGAAAGAATTCAGCGAGGTGGAAGGCCGGATCCAGGACCTGGAAAAGTACGTGGAAGATACCAAGATCG

ACCTGTGGTCCTACAACGCCGAGCTGCTGGTGGCCCTGGAAAACCAGCACACCATCGACCTGACCGACAGCG

AGATGAACAAGCTGTTCGAGCGGACCAAGAAGCAGCTGCGCGAGAACGCCGAGGACATGGGCAACGGCTGC

TTCAAGATCTACCACAAGTGCGACAATGCCTGCATCGGCAGCATCCGGAACGGCACCTACGACCACGACGTG

-continued

TACAGGGACGAGGCCCTGAACAACCGGTTCCAGATCAAGGGCGTGGAACTGAAGTCCGGCTACAAGGACTG

GATCCTGTGGATCAGCTTCGCCATCAGCTGCTTTCTGCTGTGCGTGGCCCTGCTGGGCTTCATCATGTGGGC

CTGCCAGAAAGGCAACATCCGGTGCAACATCTGCATTTAAGGCGCGCCCACCCAGCGGCCGC

SEQ ID NO: 14: amino acid sequence of HA from influenza virus A/Fujain/411/2002 (H3N2)
MKTIIALSYILCLVFAQKLPGNDNSTATLCLGHHAVPNGTIVKTITNDQIEVTNATELVQSSSTGGICDSPHQILD

GENCTLIDALLGDPQCDGFQNKKWDLFVERSKAYSNCYPYDVPDYASLRSLVASSGTLEFNNESFNWTGVTQN

GTSSACKRRSNKSFFSRLNWLTHLKYKYPALNVTMPNNEKFDKLYIWGVLHPGTDSDQISLYAQASGRITVSTK

RSQQTVIPNIGSRPRVRGVSSRISIYWTIVKPGDILLINSTGNLIAPRGYFKIRSGKSSIMRSDAPIGKCNSECITPN

GSIPNDKPFQNVNRITYGACPRYIKQNTLKLATGMRNVPEKQTRGIFGAIAGFIENGWEGMVDGWYGFRHQNS

EGTGQAADLKSTQAAINQINGKLNRLIGKTNEKFHQIEKEFSEVEGRIQDLEKYVEDTKIDLWSYNAELLVALEN

QHTIDLTDSEMNKLFERTKKQLRENAEDMGNGCFKIYHKCDNACIGSIRNGTYDHDVYRDEALNNRFQIKGVEL

KSGYKDWILWISFAISCFLLCVALLGFIMWACQKGNIRCNICI

SEQ ID NO: 15: nucleotide cDNA sequence of HA from influenza virus A/Brisbane/10/2007 (H3N2)
GGGCCCCTATAACTCTCTACGGCTAACCTGAATGGACTACGACATAGTCTAGTCCGCCAAGATGAAGACCAT

CATTGCCCTGAGCTACATCCTGTGCCTGGTGTTCACCCAGAAGCTGCCCGGCAACGACAATAGCACCGCCAC

CCTGTGTCTGGGCCACCACGCCGTGCCTAACGGCACCATCGTGAAAACCATCACCAACGACCAGATCGAAGT

GACCAACGCCACCGAGCTGGTGCAGAGCAGCAGCACCGGCGAGATCTGCGACAGCCCCCACCAGATCCTGGA

CGGCGAGAACTGCACCCTGATCGACGCCCTGCTGGGCGACCCCCAGTGCGACGGCTTCCAGAACAAGAAATG

GGACCTGTTCGTGGAAAGAAGCAAGGCCTACAGCAACTGCTACCCCTACGACGTGCCCGACTACGCCAGCCT

GAGAAGCCTGGTGGCCAGCAGCGGCACACTGGAATTCAACAACGAGAGCTTCAACTGGACCGGCGTGACCCA

GAACGGCACCAGCAGCGCCTGCATCAGAAGAAGCAACAACAGCTTCTTCAGCAGACTGAACTGGCTGACCCA

CCTGAAGTTCAAGTACCCCGCCCTGAACGTGACCATGCCCAACAACGAAAAGTTCGACAAGCTGTACATCTG

GGGCGTGCACCACCCCGGCACCGACAACGATCAGATCTTCCCATACGCCCAGGCCAGCGGCAGAATCACCGT

GTCCACCAAGAGAAGCCAGCAGACCGTGATCCCCAACATCGGCAGCAGACCCAGAGTCCGCAACATCCCCAG

CCGGATCAGCATCTACTGGACCATCGTGAAGCCCGGCGACATCCTGCTGATCAACAGCACCGGCAACCTGAT

CGCCCCCAGAGGCTACTTCAAGATTCGGAGCGGCAAGAGCAGCATCATGCGGAGCGACGCCCCCATCGGCAA

GTGCAACAGCGAGTGCATCACCCCCAACGGCAGCATCCCCAACGACAAGCCCTTCCAGAACGTGAACCGGAT

CACCTACGGCGCCTGCCCCAGATACGTGAAGCAGAACACCCTGAAGCTGGCCACCGGCATGCGGAACGTGCC

CGAGAAGCAGACCAGAGGCATCTTCGGCGCCATTGCCGGCTTCATCGAGAACGGCTGGGAGGGCATGGTGG

ACGGTTGGTACGGCTTCCGGCACCAGAACAGCGAGGGCATTGGACAGGCCGCCGACCTGAAGTCTACCCAG

GCCGCCATCGACCAGATCAACGGCAAGCTGAACAGACTGATCGGCAAGACCAACGAGAAGTTCCACCAGATC

GAGAAAGAATTCAGCGAGGTGGAAGGCCGGATCCAGGACCTGGAAAAGTACGTGGAAGATACCAAGATCGA

CCTGTGGTCCTACAACGCCGAGCTGCTGGTGGCCCTGGAAAACCAGCACACCATCGACCTGACCGACAGCGA

GATGAACAAGCTGTTCGAGAAAACCAAGAAGCAGCTGCGCGAGAACGCCGAGGACATGGGCAACGGCTGCT

TCAAGATCTACCACAAGTGCGACAATGCCTGCATCGGCAGCATCCGGAACGGCACCTACGACCACAACGTGT

ACAGGGACGAGGCCCTGAACAACCGGTTCCAGATCAAGGGCGTGGAACTGAAGTCCGGCTACAAGGACTGG

ATCCTGTGGATCAGCTTCGCCATCAGCTGCTTTCTGCTGTGCGTGGCCCTGCTGGGCTTCATCATGTGGGCC

TGCCAGAAAGGCAACATCCGGTGCAACATCTGCATTTAAGGCGCGCCCACCCAGCGGCCGC

SEQ ID NO: 16: amino acid sequence of HA from influenza virus A/Brisbane/10/2007 (H3N2)
MKTIIALSYILCLVFTQKLPGNDNSTATLCLGHHAVPNGTIVKTITNDQIEVTNATELVQSSSTGEICDSPHQILDG

ENCTLIDALLGDPQCDGFQNKKWDLFVERSKAYSNCYPYDVPDYASLRSLVASSGTLEFNNESFNWTGVTQNGT

SSACIRRSNNSFFSRLNWLTHLKFKYPALNVTMPNNEKFDKLYIWGVHHPGTDNDQIFPYAQASGRITVSTKRS

-continued

QQTVIPNIGSRPRVRNIPSRISIYWTIVKPGDILLINSTGNLIAPRGYFKIRSGKSSIMRSDAPIGKCNSECITPNGS

IPNDKPFQNVNRITYGACPRYVKQNTLKLATGMRNVPEKQTRGIFGAIAGFIENGWEGMVDGWYGFRHQNSEG

IGQAADLKSTQAAIDQINGKLNRLIGKTNEKFHQIEKEFSEVEGRIQDLEKYVEDTKIDLWSYNAELLVALENQHT

IDLTDSEMNKLFEKTKKQLRENAEDMGNGCFKIYHKCDNACIGSIRNGTYDHNVYRDEALNNRFQIKGVELKSG

YKDWILWISFAISCFLLCVALLGFIMWACQKGNIRCNICI

SEQ ID NO: 17: nucleotide cDNA sequence of HA from influenza virus A/Texas/50/2012 (H3N2)
GGGCCCCTATAACTCTCTACGGCTAACCTGAATGGACTACGACATAGTCTAGTCCGCCAAGATGAAGACCAT

CATTGCCCTGAGCTACATCCTGTGCCTGGTGTTCGCCCAGAAGCTGCCCGGCAACGACAATAGCACCGCCAC

CCTGTGTCTGGGCCACCACGCCGTGCCTAACGGCACCATCGTGAAAACCATCACCAACGACCGGATCGAAGT

GACCAACGCCACCGAGCTGGTGCAGAACAGCAGCATCGGCGAGATCTGCGACAGCCCCCACCAGATCCTGGA

CGGCGAGAACTGCACCCTGATCGACGCCCTGCTGGGCGACCCCCAGTGCGACGGCTTCCAGAACAAGAAATG

GGACCTGTTCGTGGAAAGAAGCAAGGCCTACAGCAACTGCTACCCCTACGACGTGCCCGACTACGCCAGCCT

GAGAAGCCTGGTGGCCAGCAGCGGCACACTGGAATTCAACAACGAGAGCTTCAACTGGAACGGCGTGACCCA

GAACGGCACCAGCAGCGCCTGCATCAGAAGAAGCAACAACAGCTTCTTCAGCAGACTGAACTGGCTGACCCA

CCTGAACTTCAAGTACCCCGCCCTGAACGTGACCATGCCCAACAACGAGCAGTTCGACAAGCTGTACATCTG

GGGCGTGCACCACCCCGGCACCGACAAGGACCAGATCTTCCTGTACGCCCAGCCCAGCGGCAGAATCACCGT

GTCCACCAAGAGAAGCCAGCAGGCCGTGATCCCCAACATCGGCAGCAGACCCCGGATCCGCAACATCCCCAG

CCGGATCAGCATCTACTGGACCATCGTGAAGCCCGGCGACATCCTGCTGATCAACAGCACCGGCAACCTGAT

CGCCCCCAGAGGCTACTTCAAGATTCGGAGCGGCAAGAGCAGCATCATGCGGAGCGACGCCCCCATCGGCAA

GTGCAAGAGCGAGTGCATCACCCCCAACGGCAGCATCCCCAACGACAAGCCCTTCCAGAACGTGAACCGGAT

CACCTACGGCGCCTGCCCCAGATACGTGAAGCAGAGCACCCTGAAGCTGGCCACCGGCATGCGGAACGTGCC

CGAGAAGCAGACCAGAGGCATCTTCGGCGCCATTGCCGGCTTCATCGAGAACGGCTGGGAGGGCATGGTGG

ACGGTTGGTACGGCTTCCGGCACCAGAACAGCGAGGGCAGAGGACAGGCCGCCGACCTGAAGTCTACCCAG

GCCGCCATCGACCAGATCAACGGCAAGCTGAACAGACTGATCGGCAAGACCAACGAGAAGTTCCACCAGATC

GAGAAAGAATTCAGCGAGGTGGAAGGCCGGATCCAGGACCTGGAAAAGTACGTGGAAGATACCAAGATCGA

CCTGTGGTCCTACAACGCCGAGCTGCTGGTGGCCCTGGAAAACCAGCACACCATCGACCTGACCGACAGCGA

GATGAACAAGCTGTTCGAGAAAACCAAGAAGCAGCTGCGCGAGAACGCCGAGGACATGGGCAACGGCTGCT

TCAAGATCTACCACAAGTGCGACAATGCCTGCATCGGCAGCATCCGGAACGGCACCTACGACCACGACGTGT

ACAGGGACGAGGCCCTGAACAACCGGTTCCAGATCAAGGGCGTGGAACTGAAGTCCGGCTACAAGGACTGG

ATCCTGTGGATCAGCTTCGCCATCAGCTGCTTTCTGCTGTGCGTGGCCCTGCTGGGCTTCATCATGTGGGCC

TGCCAGAAAGGCAACATCCGGTGCAACATCTGCATTTAAGGCGCGCCCACCCAGCGGCCGC

SEQ ID NO: 18: amino acid sequence of HA from influenza virus A/Texas/50/2012
(H3N2)MKTIIALSYILCLVFAQKLPGNDNSTATLCLGHHAVPNGTIVKTITNDRIEVTNATELVQNSSIGEICDSP

HQILDGENCTLIDALLGDPQCDGFQNKKWDLFVERSKAYSNCYPYDVPDYASLRSLVASSGTLEFNNESFNWNG

VTQNGTSSACIRRSNNSFFSRLNWLTHLNFKYPALNVTMPNNEQFDKLYIWGVHHPGTDKDQIFLYAQPSGRIT

VSTKRSQQAVIPNIGSRPRIRNIPSRISIYWTIVKPGDILLINSTGNLIAPRGYFKIRSGKSSIMRSDAPIGKCKSECI

TPNGSIPNDKPFQNVNRITYGACPRYVKQSTLKLATGMRNVPEKQTRGIFGAIAGFIENGWEGMVDGWYGFRH

QNSEGRGQAADLKSTQAAIDQINGKLNRLIGKTNEKFHQIEKEFSEVEGRIQDLEKYVEDTKIDLWSYNAELLVA

LENQHTIDLTDSEMNKLFEKTKKQLRENAEDMGNGCFKIYHKCDNACIGSIRNGTYDHDVYRDEALNNRFQIKG

VELKSGYKDWILWISFAISCFLLCVALLGFIMWACQKGNIRCNICI

-continued

SEQ ID NO: 19: nucleotide cDNA sequence of HA from influenza virus A/turkey/Turkey/1/2005 (H5N1)

atggagaaaatagtgcttcttcttgcaatagtcagccttgttaaaagtgatcagatttgcattggttaccatgcaaacaactcgacagagcaggtt gacacaataatggaaaagaacgtcactgttacacacgcccaagacatactggaaaagacacacaacgggaaactctgcgatctagatggag tgaagcctctaattttaagagattgtagtgtagctggatggctcctcgggaacccaatgtgtgacgaattcctcaatgtgccggaatggtcttaca tagtggagaagatcaatccagccaatgacctctgttacccagggaatttcaacgactatgaagaactgaaacacctattgagcagaataaacc attttgagaaaattcagatcatccccaaaagttcttggtcagatcatgaagcctcagcaggggtgagctcagcatgtccataccagggaaggtc ctcctttttagaaatgtggtatggcttatcaaaaaggacaatgcatacccaacaataaagagaagttacaataataccaaccaagaagatcttt tggtattgtgggggattcaccatccaaatgatgcggcagagcagacaaggctctatcaaaacccaactacctatatttccgttgggacatcaac actaaaccagagattggtaccaaaaatagccactagatctaaggtaaacgggcaaagtggaaggatggagttcttttggacaattttaaaacc gaatgatgcaataaactttgagagtaatggaaatttcattgctccagaaaatgcatacaaaattgtcaagaaaggggactcaacaattatgaa aagtgagttggaatatggtaactgcaacaccaagtgtcaaactccaataggggcgataaactctagtatgccattccacaacatccaccctctc accatcggggaatgccccaaatatgtgaaatcaagcagattagtccttgctactgggctcagaaatagccctcaacgagagacacgaggact atttggagctatagcaggttttatagagggaggatggcagggaatggtagatggttggtatgggtaccaccatagcaacgagcaggggagt gggtacgctgcagacaaagaatccactcaaaaggcaatagatggagtcaccaataaggtcaactcgatcattgacaaaatgaacactcagtt tgaggctgttggaagggaatttaataacttagaaaggagaatagaaaatttaaacaagaagatggaagacggattcctagatgtctggactt ataatgctgaacttctggttctcatggaaaatgagagaactctagactttcatgactcaaatgtcaagaacctttacgacaaggtccgactacag cttagggataatgcaaaggagcttggtaacggttgtttcgagttctatcacagatgtgataatgaatgtatggaaagtgtaagaaacggaacgt atgactacccgcagtattcagaagaagcaagattaaaaagagaggaaataagtggagtaaaattggaatcaataggaacttaccaaatact gtcaatttattcaacagtggcgagctccctagcactggcaatcatggtggctggtctatctttatggatgtgctccaatggatcgttacaatgcag aatttgcatttaa SEQ ID NO: 20: amino acid sequence of HA from influenza virus A/turkey/Turkey/1/2005 (H5N1)

MEKIVLLLAIVSLVKSDQICIGYHANNSTEQVDTIMEKNVTVTHAQDILEKTHNGKLCDLDGVKPLILRDCSVAG

WLLGNPMCDEFLNVPEWSYIVEKINPANDLCYPGNFNDYEELKHLLSRINHFEKIQIIPKSSWSDHEASAGVSSA

CPYQGRSSFFRNVVWLIKKDNAYPTIKRSYNNTNQEDLLVLWGIHHPNDAAEQTRLYQNPTTYISVGTSTLNQR

LVPKIATRSKVNGQSGRMEFFWTILKPNDAINFESNGNFIAPENAYKIVKKGDSTIMKSELEYGNCNTKCQTPIGA

INSSMPFHNIHPLTIGECPKYVKSSRLVLATGLRNSPQRETRGLFGAIAGFIEGGWQGMVDGWYGYHHSNEQGS

GYAADKESTQKAIDGVTNKVNSIIDKMNTQFEAVGREFNNLERRIENLNKKMEDGFLDVWTYNAELLVLMENER

TLDFHDSNVKNLYDKVRLQLRDNAKELGNGCFEFYHRCDNECMESVRNGTYDYPQYSEEARLKREEISGVKLESI

GTYQILSIYSTVASSLALAIMVAGLSLWMCSNGSLQCRICI

SEQ ID NO: 21: nucleotide cDNA sequence of HA from influenza virus A/Shanghai/2/2013 (H7N9)

ATGAACACTCAAATCCTGGTATTCGCTCTGATTGCGATCATTCCAACAAATGCAGACAAAATCTGCCTCGGAC

ATCATGCCGTGTCAAACGGAACCAAAGTAAACACATTAACTGAAAGAGGAGTGGAAGTCGTCAATGCAACTG

AAACAGTGGAACGAACAAACATCCCCAGGATCTGCTCAAAAGGGAAAAGGACAGTTGACCTCGGTCAATGTG

GACTCCTGGGGACAATCACTGGACCACCTCAATGTGACCAATTCCTAGAATTTTCAGCCGATTTAATTATTGA

GAGGCGAGAAGGAAGTGATGTCTGTTATCCTGGGAAATTCGTGAATGAAGAAGCTCTGAGGCAAATTCTCAG

AGAATCAGGCGGAATTGACAAGGAAGCAATGGGATTCACATACAGTGGAATAAGAACTAATGGAGCAACCAG

TGCATGTAGGAGATCAGGATCTTCATTCTATGCAGAAATGAAATGGCTCCTGTCAAACACAGATAATGCTGC

ATTCCCGCAGATGACTAAGTCATATAAAAATACAAGAAAAAGCCCAGCTCTAATAGTATGGGGGATCCATCAT

TCCGTATCAACTGCAGAGCAAACCAAGCTATATGGGAGTGGAAACAAACTGGTGACAGTTGGGAGTTCTAAT

TATCAACAATCTTTTGTACCGAGTCCAGGAGCGAGACCACAAGTTAATGGTCTATCTGGAAGAATTGACTTTC

ATTGGCTAATGCTAAATCCCAATGATACAGTCACTTTCAGTTTCAATGGGGCTTTCATAGCTCCAGACCGTGC

AAGCTTCCTGAGAGGAAAATCTATGGGAATCCAGAGTGGAGTACAGGTTGATGCCAATTGTGAAGGGGACTG

-continued

CTATCATAGTGGAGGGACAATAATAAGTAACTTGCCATTTCAGAACATAGATAGCAGGGCAGTTGGAAAATG

TCCGAGATATGTTAAGCAAAGGAGTCTGCTGCTAGCAACAGGGATGAAGAATGTTCCTGAGATTCCAAAAGG

AAGAGGCCTATTTGGTGCTATAGCGGGTTTCATTGAAAATGGATGGGAAGGCCTAATTGATGGTTGGTATGG

TTTCAGACACCAGAATGCACAGGGAGAGGGAACTGCTGCAGATTACAAAAGCACTCAATCGGCAATTGATCA

AATAACAGGAAAATTAAACCGGCTTATAGAAAAAACCAACCAACAATTTGAGTTGATAGACAATGAATTCAAT

GAGGTAGAGAAGCAAATCGGTAATGTGATAAATTGGACCAGAGATTCTATAACAGAAGTGTGGTCATACAAT

GCTGAACTCTTGGTAGCAATGGAGAACCAGCATACAATTGATCTGGCTGATTCAGAAATGGACAAACTGTAC

GAACGAGTGAAAAGACAGCTGAGAGAGAATGCTGAAGAAGATGGCACTGGTTGCTTTGAAATATTTCACAAG

TGTGATGATGACTGTATGGCCAGTATTAGAAATAACACCTATGATCACAGCAAATACAGGGAAGAGGCAA

SEQ ID NO: 22: amino acid sequence of HA from influenza virus A/Shanghai/2/2013 (H7N9)
MNTQILVFALIAIIPTNADKICLGHHAVSNGTKVNTLTERGVEVVNATETVERTNIPRICSKGKRTVDLGQCGLLG

TITGPPQCDQFLEFSADLIIERREGSDVCYPGKFVNEEALRQILRESGGIDKEAMGFTYSGIRTNGATSACRRSGS

SFYAEMKWLLSNTDNAAFPQMTKSYKNTRKSPALIVWGIHHSVSTAEQTKLYGSGNKLVTVGSSNYQQSFVPSP

GARPQVNGLSGRIDFHWLMLNPNDTVTFSFNGAFIAPDRASFLRGKSMGIQSGVQVDANCEGDCYHSGGTIISN

LPFQNIDSRAVGKCPRYVKQRSLLLATGMKNVPEIPKGRGLFGAIAGFIENGWEGLIDGWYGFRHQNAQGEGTA

ADYKSTQSAIDQITGKLNRLIEKTNQQFELIDNEFNEVEKQIGNVINWTRDSITEVWSYNAELLVAMENQHTIDL

ADSEMDKLYERVKRQLRENAEEDGTGCFEIFHKCDDDCMASIRNNTYDHSKYREEAX

SEQ ID NO: 23: forward primer for influenza H1N1 A/California/07/2009 insert
ATTCCCGTCGACGCCACCATGAAGGCAATACTAGTAGTTCT SEQ ID NO: 24 reverse primer for influenza H1N1 A/California/07/2009 insert
ATTTACGCCTAGGTTATCAAATACATATTCTACACTGTAGAGAC SEQ ID NO: 25: forward primer for H7 HA gene from A/Shanghai/2/2013
AATTAAGTCGACGCCACCATGAACACTCAAATCCTGGTATTCG SEQ ID NO: 26: reverse primer for H7 HA gene from A/Shanghai/2/2013
AATTAATCTAGATTATCATATACAAATAGTGCACCGCATG SEQ ID NO: 27 peptide
ALNNRFQIKGVELKS SEQ ID NO: 28 SB63 primer
catagtctagtcgacgccaccatggagaaaatagtgcttcttcttgc SEQ ID NO: 29 SB74 primer
gtcgaagttcagggtctgcttcacgggggccacgatcttctgcttgtgccgggcctcccgcttggcccgaatgcaaattctgcattgtaacgatc SEQ ID NO: 30 SB76 primer
gtgaagcagaccctgaacttcgacctgctgaagctggccggcgacgtggagagcaaccccggccccatgaaggcaatactagtagttctgc SEQ ID NO: 31 SB66 primer
ggcgtagcggcggccgcttatcaaatacatattctacactgtagagaccca

---

The invention claimed is:

1. An immunogenic composition comprising:

(i) a first self-replicating RNA molecule encoding a polypeptide comprising a first antigen and (ii) a second self-replicating RNA molecule encoding a polypeptide comprising a second antigen, wherein the first and second antigens are both from influenza virus, but the first antigen is from a different strain of influenza virus to the second antigen as follows:

(a) the first antigen is HA from influenza A subtype H1 or an immunogenic fragment or variant thereof, and the second antigen is HA from a different H1 strain to the first antigen or an immunogenic fragment or variant thereof; or (b) the first antigen is HA from influenza A subtype H3 or an immunogenic fragment or variant thereof, and the second antigen is HA from a different H3 strain to the first antigen or an immunogenic fragment or variant thereof.

2. The immunogenic composition of claim 1, wherein the first and second antigens are the only antigens from influenza virus in the self-replicating RNA molecules.

3. The immunogenic composition of claim 1, further comprising: (iii) a third self-replicating RNA molecule encoding a polypeptide comprising a third antigen, wherein the third antigen is from influenza virus, but is from a different strain of influenza virus to both the first and second antigens.

4. The immunogenic composition of claim 3, wherein the first, second, and third antigens are the only antigens from influenza virus in the self-replicating RNA molecules.

5. The immunogenic composition of claim 3, further comprising: (iv) a fourth self-replicating RNA molecule encoding a polypeptide comprising a fourth antigen, wherein the fourth antigen is from influenza virus, but is from a different strain of influenza virus to the first, second, and third antigens.

6. The immunogenic composition of claim 5, wherein the first and second antigens are HA from influenza A subtype H1 or an immunogenic fragment or variant thereof and the third and fourth antigens are from influenza A subtype H3 or an immunogenic fragment or variant thereof.

7. The immunogenic composition of claim 1, further comprising an adjuvant.

8. The immunogenic composition of claim 1, wherein the self-replicating RNA molecule is derived from an alphavirus.

9. The immunogenic composition of claim 8, wherein the alphavirus is selected from the group consisting of: Sindbis (SIN), Venezuelan equine encephalitis (VEE), Semliki Forest virus (SFV), and combinations thereof.

10. A pharmaceutical composition comprising the immunogenic composition of claim 1 and a pharmaceutically acceptable carrier comprising a cationic lipid.

11. A method of prevention and/or treatment against influenza disease, comprising administering an effective amount of the immunogenic composition of claim 1 to a person in need thereof.

12. A method for inducing an immune response in a subject comprising administering to the subject an effective amount of the pharmaceutical composition claim 10.

13. A method of prevention and/or treatment against influenza disease, comprising the steps of:

(i) administering an effective amount to a person in need of a first immunogenic composition comprising a first self-replicating RNA molecule encoding a polypeptide comprising a first antigen and pharmaceutically acceptable carrier; and (ii) simultaneous, at substantially the same time, or sequential administration of a second immunogenic composition comprising a second self-replicating RNA molecule encoding a polypeptide comprising a second antigen and pharmaceutically acceptable carrier, wherein the first and second antigens are both from influenza virus, but the first antigen is from a different strain of influenza to the second antigen as follows:

(a) the first antigen is HA from influenza A subtype H1 or an immunogenic fragment or variant thereof and the second antigen is HA from a different H1 strain to the first antigen or an immunogenic fragment or variant thereof; or (b) the first antigen is HA from influenza A subtype H3 or an immunogenic fragment or variant thereof and the second antigen is HA from a different H3 strain to the first antigen or an immunogenic fragment or variant thereof.

14. A method of preparing the immunogenic composition of claim 1, the method comprising: (i) providing at least one lipid which forms nanoparticles; (ii) providing an aqueous solution comprising the self-replicating RNA molecules; and (iii) combining the aqueous solution of (ii) and the at least one lipid of (i), thereby preparing the composition.

15. An immunogenic composition comprising multiple self-replicating RNA molecule populations, wherein each self-replicating RNA molecule population encodes a polypeptide comprising an HA antigen from a different strain of the influenza H3N2 subtype.

16. The immunogenic composition of claim 15, comprising six self-replicating RNA molecules, wherein: (i) a first self-replicating RNA molecule encodes a polypeptide comprising a first antigen from A/Bilthoven/16398/1968, (ii) a second self-replicating RNA molecule encodes a polypeptide comprising a second antigen from A/Bangkok/1/79, (iii) a third self-replicating RNA molecule encodes a polypeptide comprising a third antigen from A/Beijing/32/92, (iv) a fourth self-replicating RNA molecule encodes a polypeptide comprising a fourth antigen from A/Fujian/411/2002, (v) a fifth self-replicating RNA molecule encodes a polypeptide comprising a fifth antigen from A/Brisbane/10/2007, and (vi) a sixth self-replicating RNA molecule encodes a polypeptide comprising a sixth antigen from A/Texas/50/2012.

* * * * *

SEQUENCE LISTING

<160> NUMBER OF SEQ ID NOS: 31

<210> SEQ ID NO 1
<211> LENGTH: 11688
<212> TYPE: DNA
<213> ORGANISM: Artificial Sequence
<220> FEATURE:
<223> OTHER INFORMATION: Nucleotide cDNA sequence of A836 TC83 VEE/SINV
(Venezuelan equine encephalitis-Sindbis virus) chimeric replicon
containing T7 DNA polymerase promoter

<400> SEQUENCE: 1
ataggcggcg catgagagaa gcccagacca attacctacc caaaatggag aaagttcacg 60

```
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
```

-continued

```
ttgacgaagc ttttgcttgt catgcaggta ctctcagagc gctcatagcc attataagac   2460
ctaaaaaggc agtgctctgc ggggatccca aacagtgcgg ttttttaac atgatgtgcc   2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc   4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
```

```
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
```

-continued

```
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatggagaaa atagtgcttc ttcttgcaat agtcagcctt gttaaaagtg atcagatttg   7620
cattggttac catgcaaaca actcgacaga gcaggttgac acaataatgg aaaagaacgt   7680
cactgttaca cacgcccaag acatactgga aaagacacac aacgggaaac tctgcgatct   7740
agatggagtg aagcctctaa ttttaagaga ttgtagtgta gctggatggc tcctcgggaa   7800
cccaatgtgt gacgaattcc tcaatgtgcc ggaatggtct tacatagtgg agaagatcaa   7860
tccagccaat gacctctgtt acccaggga tttcaacgac tatgaagaac tgaaacacct   7920
attgagcaga ataaaccatt ttgagaaaat tcagatcatc cccaaaagtt cttggtcaga   7980
tcatgaagcc tcagcagggg tgagctcagc atgtccatac cagggaaggt cctccttttt   8040
tagaaatgtg gtatggctta tcaaaaagga caatgcatac ccaacaataa agagaagtta   8100
caataatacc aaccaagaag atcttttggt attgtggggg attcaccatc caaatgatgc   8160
ggcagagcag acaaggctct atcaaaaccc aactacctat atttccgttg ggacatcaac   8220
actaaaccag agattggtac caaaaatagc cactagatct aaggtaaacg ggcaaagtgg   8280
aaggatggag ttcttttgga caattttaaa accgaatgat gcaataaact ttgagagtaa   8340
tggaaatttc attgctccag aaaatgcata caaaattgtc aagaaagggg actcaacaat   8400
tatgaaaagt gagttggaat atggtaactg caacaccaag tgtcaaactc caataggggc   8460
gataaactct agtatgccat tccacaacat ccaccctctc accatcgggg aatgccccaa   8520
atatgtgaaa tcaagcagat tagtccttgc tactgggctc agaaatagcc ctcaacgaga   8580
gacacgagga ctatttggag ctatagcagg ttttatagag ggaggatggc agggaatggt   8640
agatggttgg tatgggtacc accatagcaa cgagcagggg agtgggtacg ctgcagacaa   8700
agaatccact caaaaggcaa tagatggagt caccaataag gtcaactcga tcattgacaa   8760
aatgaacact cagtttgagg ctgttggaag ggaatttaat aacttagaaa ggagaataga   8820
aaatttaaac aagaagatgg aagacggatt cctagatgtc tggacttata atgctgaact   8880
tctggttctc atggaaaatg agagaactct agactttcat gactcaaatg tcaagaacct   8940
ttacgacaag gtccgactac agcttaggga taatgcaaag gagcttggta acggttgttt   9000
cgagttctat cacagatgtg ataatgaatg tatggaaagt gtaagaaacg gaacgtatga   9060
ctacccgcag tattcagaag aagcaagatt aaaaagagag gaaataagtg gagtaaaatt   9120
ggaatcaata ggaacttacc aaatactgtc aatttattca acagtggcga gctccctagc   9180
actggcaatc atggtggctg gtctatcttt atggatgtgc tccaatggat cgttacaatg   9240
cagaatttgc atttaaggcg cgcccaccca gcggccgcat acagcagcaa ttggcaagct   9300
gcttacatag aactcgcggc gattggcatg ccgccttaaa atttttattt tattttttctt   9360
ttcttttccg aatcggattt tgtttttaat atttcaaaaa aaaaaaaaaa aaaaaaaaaa   9420
aaaaaaaaaa aaaaagaaga gcgtttaaac acgtgatatc tggcctcatg ggccttcctt   9480
tcactgcccg ctttccagtc gggaaacctg tcgtgccagc tgcattaaca tggtcatagc   9540
```

```
tgtttccttg cgtattgggc gctctccgct tcctcgctca ctgactcgct gcgctcggtc   9600
gttcgggtaa agcctggggt gcctaatgag caaaaggcca gcaaaaggcc aggaaccgta   9660
aaaaggccgc gttgctggcg tttttccata ggctccgccc ccctgacgag catcacaaaa   9720
atcgacgctc aagtcagagg tggcgaaacc cgacaggact ataaagatac caggcgtttc   9780
cccctggaag ctccctcgtg cgctctcctg ttccgaccct gccgcttacc ggatacctgt   9840
ccgcctttct cccttcggga agcgtggcgc tttctcatag ctcacgctgt aggtatctca   9900
gttcggtgta ggtcgttcgc tccaagctgg gctgtgtgca cgaacccccc gttcagcccg   9960
accgctgcgc cttatccggt aactatcgtc ttgagtccaa cccggtaaga cacgacttat  10020
cgccactggc agcagccact ggtaacagga ttagcagagc gaggtatgta ggcggtgcta  10080
cagagttctt gaagtggtgg cctaactacg gctacactag aagaacagta tttggtatct  10140
gcgctctgct gaagccagtt accttcggaa aaagagttgg tagctcttga tccggcaaac  10200
aaaccaccgc tggtagcggt ggtttttttg tttgcaagca gcagattacg cgcagaaaaa  10260
aaggatctca agaagatcct ttgatctttt ctacggggtc tgacgctcag tggaacgaaa  10320
actcacgtta agggattttg gtcatgaata cacggtgcct gactgcgtta gcaatttaac  10380
tgtgataaac taccgcatta aagcttatcg atgataagct gtcaaacatg agaattctta  10440
gaaaaactca tcgagcatca aatgaaactg caatttattc atatcaggat tatcaatacc  10500
atatttttga aaaagccgtt tctgtaatga aggagaaaac tcaccgaggc agttccatag  10560
gatggcaaga tcctggtatc ggtctgcgat tccgactcgt ccaacatcaa tacaacctat  10620
taatttcccc tcgtcaaaaa taaggttatc aagtgagaaa tcaccatgag tgacgactga  10680
atccggtgag aatggcaaaa gcttatgcat ttctttccag acttgttcaa caggccagcc  10740
attacgctcg tcatcaaaat cactcgcatc aaccaaaccg ttattcattc gtgattgcgc  10800
ctgagcgaga cgaaatacgc gatcgctgtt aaaaggacaa ttacaaacag gaatcgaatg  10860
caaccggcgc aggaacactg ccagcgcatc aacaatattt tcacctgaat caggatattc  10920
ttctaatacc tggaatgctg ttttcccggg gatcgcagtg gtgagtaacc atgcatcatc  10980
aggagtacgg ataaaatgct tgatggtcgg aagaggcata aattccgtca gccagtttag  11040
tctgaccatc tcatctgtaa catcattggc aacgctacct ttgccatgtt tcagaaacaa  11100
ctctggcgca tcgggcttcc catacaatcg atagattgtc gcacctgatt gcccgacatt  11160
atcgcgagcc catttatacc catataaatc agcatccatg ttggaattta atcgcggcct  11220
cgagcaagac gtttcccgtt gaatatggct cataacaccc cttgtattac tgtttatgta  11280
agcagacagt tttattgttc atgagcggat acatatttga atgtatttag aaaaataaac  11340
aaataggggt tccgcgcaca tttccccgaa aagtgccacc taaattgtaa gcgttaatat  11400
tttgttaaaa ttcgcgttaa atttttgtta aatcagctca ttttttaacc aataggccga  11460
aatcggcaaa atcccttata aatcaaaaga atagaccgag atagggttga gtggccgcta  11520
cagggcgctc ccattcgcca ttcaggctgc gcaactgttg ggaagggcgt ttcggtgcgg  11580
gcctcttcgc tattacgcca gctggcgaaa gggggatgtg ctgcaaggcg attaagttgg  11640
gtaacgccag ggttttccca gtcacacgcg taatacgact cactatag              11688
```

<210> SEQ ID NO 2
<211> LENGTH: 9993
<212> TYPE: DNA
<213> ORGANISM: Artificial Sequence
<220> FEATURE:

-continued

<223> OTHER INFORMATION: Nucleotide cDNA sequence of A836 TC83 VEE/SINV chimeric replicon without insert

<400> SEQUENCE: 2

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
```

-continued

```
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc    2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgaggggga tattgccacg gccaccgaag  4080
gagtgattat aaatgctgct aacagcaaag gacaacctgg cggagggggtg tgcggagcgc  4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
```

-continued

```
caagcgatgg caaaactttc tcatatttgg aagggaccaa gtttcaccag gcggccaagg   4680

atatagcaga aattaatgcc atgtggcccg ttgcaacgga ggccaatgag caggtatgca   4740

tgtatatcct cggagaaagc atgagcagta ttaggtcgaa atgccccgtc gaagagtcgg   4800

aagcctccac accacctagc acgctgcctt gcttgtgcat ccatgccatg actccagaaa   4860

gagtacagcg cctaaaagcc tcacgtccag aacaaattac tgtgtgctca tcctttccat   4920

tgccgaagta tagaatcact ggtgtgcaga agatccaatg ctcccagcct atattgttct   4980

caccgaaagt gcctgcgtat attcatccaa ggaagtatct cgtggaaaca ccaccggtag   5040

acgagactcc ggagccatcg gcagagaacc aatccacaga ggggacacct gaacaaccac   5100

cacttataac cgaggatgag accaggacta gaacgcctga gccgatcatc atcgaagagg   5160

aagaagagga tagcataagt ttgctgtcag atggcccgac ccaccaggtg ctgcaagtcg   5220

aggcagacat tcacgggccg ccctctgtat ctagctcatc ctggtccatt cctcatgcat   5280

ccgactttga tgtggacagt ttatccatac ttgacaccct ggagggagct agcgtgacca   5340

gcggggcaac gtcagccgag actaactctt acttcgcaaa gagtatggag tttctggcgc   5400

gaccggtgcc tgcgcctcga acagtattca ggaaccctcc acatcccgct ccgcgcacaa   5460

gaacaccgtc acttgcaccc agcagggcct gctcgagaac cagcctagtt tccacccccgc   5520

caggcgtgaa tagggtgatc actagagagg agctcgaggc gcttaccccg tcacgcactc   5580

ctagcaggtc ggtctcgaga accagcctgg tctccaaccc gccaggcgta aatagggtga   5640

ttacaagaga ggagtttgag gcgttcgtag cacaacaaca atgacggttt gatgcgggtg   5700

catacatctt ttcctccgac accggtcaag ggcatttaca acaaaaatca gtaaggcaaa   5760

cggtgctatc cgaagtggtg ttggagagga ccgaattgga gatttcgtat gccccgcgcc   5820

tcgaccaaga aaaagaagaa ttactacgca agaaattaca gttaaatccc acacctgcta   5880

acagaagcag ataccagtcc aggaaggtgg agaacatgaa agccataaca gctagacgta   5940

ttctgcaagg cctagggcat tatttgaagg cagaaggaaa agtggagtgc taccgaaccc   6000

tgcatcctgt tcctttgtat tcatctagtg tgaaccgtgc cttttcaagc cccaaggtcg   6060

cagtggaagc ctgtaacgcc atgttgaaag agaactttcc gactgtggct tcttactgta   6120

ttattccaga gtacgatgcc tatttggaca tggttgacgg agcttcatgc tgcttagaca   6180

ctgccagttt ttgccctgca aagctgcgca gctttccaaa gaaacactcc tatttggaac   6240

ccacaatacg atcggcagtg ccttcagcga tccagaacac gctccagaac gtcctggcag   6300

ctgccacaaa aagaaattgc aatgtcacgc aaatgagaga attgcccgta ttggattcgg   6360

cggcctttaa tgtggaatgc ttcaagaaat atgcgtgtaa taatgaatat tgggaaacgt   6420

ttaaagaaaa ccccatcagg cttactgaag aaaacgtggt aaattacatt accaaattaa   6480

aaggaccaaa agctgctgct ctttttgcga agacacataa tttgaatatg ttgcaggaca   6540

taccaatgga caggtttgta atggacttaa agagagacgt gaaagtgact ccaggaacaa   6600

aacatactga agaacggccc aaggtacagg tgatccaggc tgccgatccg ctagcaacag   6660

cgtatctgtg cggaatccac cgagagctgg ttaggagatt aaatgcggtc ctgcttccga   6720

acattcatac actgtttgat atgtcggctg aagactttga cgctattata gccgagcact   6780

tccagcctgg ggattgtgtt ctggaaactg acatcgcgtc gtttgataaa agtgaggacg   6840

acgccatggc tctgaccgcg ttaatgattc tggaagactt aggtgtggac gcagagctgt   6900

tgacgctgat tgaggcggct ttcggcgaaa tttcatcaat acatttgccc actaaaacta   6960
```

-continued

```
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga ccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gggcgcgccc acccagcggc cgcatacagc agcaattggc aagctgctta catagaactc   7620
gcggcgattg gcatgccgcc ttaaaatttt tattttattt ttcttttctt ttccgaatcg   7680
gattttgttt ttaatatttc aaaaaaaaaa aaaaaaaaaa aaaaaaaaaa aaaaaaaaaa   7740
gaagagcgtt taaacacgtg atatctggcc tcatgggcct tcctttcact gcccgctttc   7800
cagtcgggaa acctgtcgtg ccagctgcat taacatggtc atagctgttt ccttgcgtat   7860
tgggcgctct ccgcttcctc gctcactgac tcgctgcgct cggtcgttcg ggtaaagcct   7920
ggggtgccta atgagcaaaa ggccagcaaa aggccaggaa ccgtaaaaag gccgcgttgc   7980
tggcgttttt ccataggctc cgcccccctg acgagcatca caaaaatcga cgctcaagtc   8040
agaggtggcg aaacccgaca ggactataaa gataccaggc gtttccccct ggaagctccc   8100
tcgtgcgctc tcctgttccg accctgccgc ttaccggata cctgtccgcc tttctccctt   8160
cgggaagcgt ggcgctttct catagctcac gctgtaggta tctcagttcg gtgtaggtcg   8220
ttcgctccaa gctgggctgt gtgcacgaac cccccgttca gcccgaccgc tgcgccttat   8280
ccggtaacta tcgtcttgag tccaacccgg taagacacga cttatcgcca ctggcagcag   8340
ccactggtaa caggattagc agagcgaggt atgtaggcgg tgctacagag ttcttgaagt   8400
ggtggcctaa ctacggctac actagaagaa cagtatttgg tatctgcgct ctgctgaagc   8460
cagttacctt cggaaaaaga gttggtagct cttgatccgg caaacaaacc accgctggta   8520
gcggtggttt ttttgtttgc aagcagcaga ttacgcgcag aaaaaaagga tctcaagaag   8580
atcctttgat cttttctacg gggtctgacg ctcagtggaa cgaaaactca cgttaaggga   8640
ttttggtcat gaatacacgg tgcctgactg cgttagcaat ttaactgtga taaactaccg   8700
cattaaagct tatcgatgat aagctgtcaa acatgagaat tcttagaaaa actcatcgag   8760
catcaaatga aactgcaatt tattcatatc aggattatca ataccatatt tttgaaaaag   8820
ccgtttctgt aatgaaggag aaaactcacc gaggcagttc cataggatgg caagatcctg   8880
gtatcggtct gcgattccga ctcgtccaac atcaatacaa cctattaatt tcccctcgtc   8940
aaaaataagg ttatcaagtg agaaatcacc atgagtgacg actgaatccg gtgagaatgg   9000
caaaagctta tgcatttctt tccagacttg ttcaacaggc cagccattac gctcgtcatc   9060
aaaatcactc gcatcaacca aaccgttatt cattcgtgat tgcgcctgag cgagacgaaa   9120
tacgcgatcg ctgttaaaag gacaattaca aacaggaatc gaatgcaacc ggcgcaggaa   9180
cactgccagc gcatcaacaa tattttcacc tgaatcagga tattcttcta atacctggaa   9240
tgctgttttc ccggggatcg cagtggtgag taaccatgca tcatcaggag tacggataaa   9300
atgcttgatg gtcggaagag gcataaattc cgtcagccag tttagtctga ccatctcatc   9360
```

```
tgtaacatca ttggcaacgc tacctttgcc atgtttcaga aacaactctg gcgcatcggg   9420

cttcccatac aatcgataga ttgtcgcacc tgattgcccg acattatcgc gagcccattt   9480

atacccatat aaatcagcat ccatgttgga atttaatcgc ggcctcgagc aagacgtttc   9540

ccgttgaata tggctcataa cacccccttgt attactgttt atgtaagcag acagttttat   9600

tgttcatgag cggatacata tttgaatgta tttagaaaaa taaacaaata ggggttccgc   9660

gcacatttcc ccgaaaagtg ccacctaaat tgtaagcgtt aatattttgt taaaattcgc   9720

gttaaatttt tgttaaatca gctcattttt taaccaatag gccgaaatcg gcaaaatccc   9780

ttataaatca aaagaataga ccgagatagg gttgagtggc cgctacaggg cgctcccatt   9840

cgccattcag gctgcgcaac tgttgggaag ggcgtttcgg tgcgggcctc ttcgctatta   9900

cgccagctgg cgaaaggggg atgtgctgca aggcgattaa gttgggtaac gccagggttt   9960

tcccagtcac acgcgtaata cgactcacta tag                                 9993
```

<210> SEQ ID NO 3
<211> LENGTH: 1704
<212> TYPE: DNA
<213> ORGANISM: Influenza virus

<400> SEQUENCE: 3

```
atgaaggcaa tactagtagt tctgctatat acatttgcaa ccgcaaatgc agacacatta     60

tgtataggtt atcatgcgaa caattcaaca gacactgtag acacagtact agaaaagaat    120

gtaacagtaa cacactctgt taaccttcta gaagacaagc ataacgggaa actatgcaaa    180

ctaagagggg tagccccatt gcatttgggt aaatgtaaca ttgctggctg gatcctggga    240

aatccagagt gtgaatcact ctccacagca agctcatggt cctacattgt ggaaacacct    300

agttcagaca atggaacgtg ttacccagga gatttcatcg attatgagga gctaagagag    360

caattgagct cagtgtcatc atttgaaagg tttgagatat tccccaagac aagttcatgg    420

cccaatcatg actcgaacaa aggtgtaacg gcagcatgtc ctcatgctgg agcaaaaagc    480

ttctacaaaa atttaatatg gctagttaaa aaaggaaatt catacccaaa gctcagcaaa    540

tcctacatta atgataaagg gaaagaagtc ctcgtgctat ggggcattca ccatccatct    600

actagtgctg accaacaaag tctctatcag aatgcagatg catatgtttt tgtggggtca    660

tcaagataca gcaagacgtt caagccggaa atagcaataa gacccaaagt gagggatcga    720

gaagggagaa tgaactatta ctggacacta gtagagccgg gagacaaaat aacattcgaa    780

gcaactggaa atctagtggt accgagatat gcattcgcaa tggaaagaaa tgctggatct    840

ggtattatca tttcagatac accagtccac gattgcaata caacttgtca aacacccaag    900

ggtgctataa acaccagcct cccatttcag aatatacatc cgatcacaat tggaaaatgt    960

ccaaaatatg taaaaagcac aaaattgaga ctggccacag gattgaggaa tatcccgtct   1020

attcaatcta gaggcctatt tggggccatt gccggtttca ttgaaggggg gtggacaggg   1080

atggtagatg gatggtacgg ttatcaccat caaaatgagc aggggtcagg atatgcagcc   1140

gacctgaaga gcacacagaa tgccattgac gagattacta acaaagtaaa ttctgttatt   1200

gaaaagatga atacacagtt cacagcagta ggtaaagagt tcaaccacct ggaaaaaaga   1260

atagagaatt taaataaaaa agttgatgat ggtttcctgg acatttggac ttacaatgcc   1320

gaactgttgg ttctattgga aaatgaaaga actttggact accacgattc aaatgtgaag   1380

aacttatatg aaaaggtaag aagccagcta aaaaacaatg ccaaggaaat tggaaacggc   1440
```

-continued

```
tgctttgaat tttaccacaa atgcgataac acgtgcatgg aaagtgtcaa aaatgggact   1500

tatgactacc caaaatactc agaggaagca aaattaaaca gagaagaaat agatggggta   1560

aagctggaat caacaaggat ttaccagatt ttggcgatct attcaactgt cgccagttca   1620

ttggtactgg tagtctccct gggggcaatc agtttctgga tgtgctctaa tgggtctcta   1680

cagtgtagaa tatgtatttg ataa                                          1704
```

```
<210> SEQ ID NO 4
<211> LENGTH: 566
<212> TYPE: PRT
<213> ORGANISM: Influenza virus

<400> SEQUENCE: 4

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Thr Phe Lys Pro Glu Ile Ala Ile Arg Pro Lys Val Arg Asp Arg
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
```

```
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 5
<211> LENGTH: 1701
<212> TYPE: DNA
<213> ORGANISM: Influenza virus

<400> SEQUENCE: 5

atgaaggcaa acctactggt cctgttatgt gcacttgcag ctgcagatgc agacacaata      60

tgtataggct accatacgaa caattcaacc gacactgttg acacagtact cgagaagaat     120

gtgacagtga cacactctgt taacctgctc gaagacagcc acaacggaaa actatgtaga     180

ttaaaaggaa tagccccact acaattgggg aaatgtaaca tcgccggatg gctcttggga     240

aacccagaat gcgacccact gcttccagtg agatcatggt cctacattgt agaaacacca     300

aactctgaga atggaatatg ttatccagga gatttcatcg actatgagga gctgagggag     360

caattgagct cagtgtcatc attcgaaaga ttcgaaatat ttcccaaaga aagctcatgg     420

cccaaccaca acacaaacgg agtaacggca gcatgctccc atgaggggaa aagcagtttt     480

tacagaaatt tgctatggct gacggagaag gagggctcat acccaaagct gaaaaattct     540

tatgtgaaca aaaaagggaa agaagtcctt gtactgtggg gtattcatca cccgcctaac     600

agtaaggaac aacagaatct ctatcagaat gaaaatgctt atgtctctgt agtgacttca     660

aattataaca ggagatttac cccggaaata gcagaaagac ccaaagtaag agatcaagct     720
```

-continued

```
gggaggatga actattactg gaccttgcta aaacccggag acacaataat atttgaggca     780

aatggaaatc taatagcacc aatgtatgct ttcgcactga gtagaggctt tgggtccggc     840

atcatcacct caaacgcatc aatgcatgag tgtaacacga agtgtcaaac acccctggga     900

gctataaaca gcagtctccc ttaccagaat atacacccag tcacaatagg agagtgccca     960

aaatacgtca ggagtgccaa attgaggatg gttacaggac taaggaacat tccgtccatt    1020

caatccagag gtctatttgg agccattgcc ggttttattg aagggggatg gactggaatg    1080

atagatggat ggtatggtta tcatcatcag aatgaacagg gatcaggcta tgcagcggat    1140

caaaaaagca cacaaaatgc cattaacggg attacaaaca aggtgaacac tgttatcgag    1200

aaaatgaaca ttcaattcac agctgtgggt aaagaattca acaaattaga aaaaaggatg    1260

gaaaatttaa ataaaaaagt tgatgatgga tttctggaca tttggacata taatgcagaa    1320

ttgttagttc tactggaaaa tgaaaggact ctggaattcc atgactcaaa tgtgaagaat    1380

ctgtatgaga aagtaaaaag ccaattaaag aataatgcca aagaaatcgg aaatggatgt    1440

tttgagttct accacaagtg tgacaatgaa tgcatggaaa gtgtaagaaa tgggacttat    1500

gattatccca aatattcaga agagtcaaag ttgaacaggg aaaaggtaga tggagtgaaa    1560

ttggaatcaa tggggatcta tcagattctg gcgatctact caactgtcgc cagttcactg    1620

gtgcttttgg tctccctggg ggcaatcagt ttctggatgt gttctaatgg atctttgcag    1680

tgcagaatat gcatctgata a                                               1701
```

```
<210> SEQ ID NO 6
<211> LENGTH: 565
<212> TYPE: PRT
<213> ORGANISM: Influenza virus

<400> SEQUENCE: 6

Met Lys Ala Asn Leu Leu Val Leu Leu Cys Ala Leu Ala Ala Ala Asp
1               5                   10                  15

Ala Asp Thr Ile Cys Ile Gly Tyr His Thr Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
```

```
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Glu Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 7
<211> LENGTH: 1784
<212> TYPE: DNA
<213> ORGANISM: Influenza virus

<400> SEQUENCE: 7
```

gggcccctat aactctctac ggctaacctg aatggactac gacatagtct agtccgccaa 60
gatgaagacc atcattgccc tgagctacat cttctgcctg gccctgggac aggacctgcc 120
cggcaacgac aatagcaccg ccaccctgtg tctgggccac cacgccgtgc ctaacggcac 180
cctggtgaaa accatcaccg acgaccagat cgaagtgacc aacgccaccg agctggtgca 240
gagcagcagc accggcaaga tctgcaacaa cccccaccgg atcctggacg gcatcaactg 300
caccctgatc gacgccctgc tgggcgaccc ccactgcgac gtgttccagg acgagacatg 360
ggacctgttc gtggaaagaa gcaaggcctt cagcaactgc taccctacg acgtgcccga 420
ctacgccagc ctgagaagcc tggtggccag cagcggcaca ctggaattca tcaccgaggg 480
cttcacctgg accggcgtga cccagaacgg cggcagcaac gcctgcaaga gaggccctgg 540
cagcggcttc ttcagcagac tgaactggct gaccaagagc ggcagcacct accccgtgct 600
gaacgtgacc atgcccaaca acgacaactt cgacaagctg tacatctggg gcgtgcacca 660
ccccagcacc aaccaggaac agaccagcct gtacgtgcag gccagcggca gagtgaccgt 720
gtccaccaga agaagccagc agaccatcat ccccaacatc ggcagcagac cctgggtccg 780
cggcctgagc agccggatca gcatctactg gaccatcgtg aagcccggcg acgtgctggt 840
gatcaacagc aacggcaacc tgatcgcccc cagaggctac ttcaagatgc ggaccggcaa 900
gagcagcatc atgcggagcg acgcccccat cgatacctgc atcagcgagt gcatcacccc 960
caacggcagc atccccaacg acaagccctt ccagaacgtg aacaagatca cctacggcgc 1020
ctgccccaaa tacgtgaagc agaacaccct gaagctggcc accggcatgc ggaacgtgcc 1080
cgagaagcag accagaggcc tgttcggcgc cattgccggc ttcatcgaga acggctggga 1140
gggcatgatc gacggttggt acggcttccg gcaccagaac agcgagggca caggacaggc 1200
cgccgacctg aagtctaccc aggccgccat cgaccagatc aacggcaagc tgaacagagt 1260
gatcgaaaag accaacgaga agttccacca gatcgagaaa gaattcagcg aggtggaagg 1320
ccggatccag gacctggaaa agtacgtgga agataccaag atcgacctgt ggtcctacaa 1380
cgccgagctg ctggtggccc tggaaaacca gcacaccatc gacctgaccg acagcgagat 1440
gaacaagctg ttcgagaaaa ccagacggca gctgcgcgag aacgccgagg acatgggcaa 1500
cggctgcttc aagatctacc acaagtgcga caatgcctgc atcgagagca tccggaacgg 1560
cacctacgac cacgacgtgt acagggacga ggccctgaac aaccggttcc agatcaaggg 1620
cgtggaactg aagtccggct acaaggactg gatcctgtgg atcagcttcg ccatcagctg 1680
ctttctgctg tgcgtggtgc tgctgggctt catcatgtgg gcctgccagc ggggcaacat 1740
ccggtgcaac atctgcattt aaggcgcgcc cacccagcgg ccgc 1784

<210> SEQ ID NO 8
<211> LENGTH: 566
<212> TYPE: PRT
<213> ORGANISM: Influenza virus

<400> SEQUENCE: 8

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Ser Thr
50 55 60

```
Gly Lys Ile Cys Asn Asn Pro His Arg Ile Leu Asp Gly Ile Asn Cys
65                  70                  75                  80

Thr Leu Ile Asp Ala Leu Leu Gly Asp Pro His Cys Asp Val Phe Gln
                85                  90                  95

Asp Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
    130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Ala Ser Gly Arg Val Thr Val Ser Thr Arg Arg
    210                 215                 220

Ser Gln Gln Thr Ile Ile Pro Asn Ile Gly Ser Arg Pro Trp Val Arg
225                 230                 235                 240

Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480
```

-continued

```
Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565
```

<210> SEQ ID NO 9
<211> LENGTH: 1784
<212> TYPE: DNA
<213> ORGANISM: Influenza virus

<400> SEQUENCE: 9

```
gggcccctat aactctctac ggctaacctg aatggactac gacatagtct agtccgccaa     60

gatgaagacc atcattgccc tgagctacat cttctgcctg gtgttcgccc agaacctgcc    120

cggcaacgac aatagcaccg ccaccctgtg tctgggccac cacgccgtgc ctaacggcac    180

cctggtgaaa accatcacca acgaccagat cgaagtgacc aacgccaccg agctggtgca    240

gagcagcagc accggcagaa tctgcgacag cccccaccgg atcctggacg gcaagaactg    300

caccctgatc gacgccctgc tgggcgaccc ccactgcgac ggcttccaga acgagaagtg    360

ggacctgttc gtggaaagaa gcaaggcctt cagcaactgc taccccctacg acgtgcccga    420

ctacgccagc ctgagaagcc tggtggccag cagcggcaca ctggaattca tcaacgaggg    480

cttcaactgg accggcgtga cccagagcgg cggcagctat gcctgcaaga gaggcagcga    540

caagagcttc ttcagcagac tgaactggct gtacgagagc gagagcaagt accccgtgct    600

gaacgtgacc atgcccaaca acggcaactt cgacaagctg tacatctggg gcgtgcacca    660

ccccagcacc gacaaagaac agaccaacct gtacgtgcgg gccagcggca gagtgaccgt    720

gtccaccaag agaagccagc agaccatcat ccccaacatc ggcagcagac cctgggtccg    780

cggcctgagc agcggcatca gcatctactg gaccatcgtg aagcccggcg acatcctgct    840

gatcaacagc aacggcaacc tgatcgcccc cagaggctac ttcaagatcc ggaccggcaa    900

gagcagcatc atgcggagcg acgcccccat cgggacctgc agcagcgagt gcatcacccc    960

caacggcagc atccccaacg acaagccctt ccagaacgtg aacaagatca cctacggcgc   1020

ctgccccaaa tacgtgaagc agaacaccct gaagctggcc accggcatgc ggaacgtgcc   1080

cgagaagcag accagaggca tcttcggcgc cattgccggc ttcatcgaga acggctggga   1140

gggcatggtg gacggttggt acggcttccg gcaccagaac agcgagggca caggacaggc   1200

cgccgacctg aagtctaccc aggccgccat cgaccagatc aacggcaagc tgaacagagt   1260

gatcgaaaag accaacgaga agttccacca gatcgagaaa gaattcagcg aggtggaagg   1320

ccggatccag gacctggaaa agtacgtgga agataccaag atcgacctgt ggtcctacaa   1380

cgccgagctg ctggtggccc tggaaaacca gcacaccatc gacctgaccg acagcgagat   1440

gaacaagctg ttcgagaaaa ccagacggca gctgcgcgag aacgccgagg acatgggcaa   1500

cggctgcttc aagatctacc acaagtgcga caatgcctgc atcggcagca tccggaacgg   1560

cacctacgac cacgacgtgt acagggacga ggccctgaac aaccggttcc agatcaaggg   1620
```

```
cgtggaactg aagtccggct acaaggactg gatcctgtgg atcagcttcg ccatcagctg   1680

ctttctgctg tgcgtggtgc tgctgggctt catcatgtgg gcctgccaga aaggcaacat   1740

ccggtgcaac atctgcattt aaggcgcgcc cacccagcgg ccgc                    1784


<210> SEQ ID NO 10
<211> LENGTH: 566
<212> TYPE: PRT
<213> ORGANISM: Influenza virus

<400> SEQUENCE: 10

Met Lys Thr Ile Ile Ala Leu Ser Tyr Ile Phe Cys Leu Val Phe Ala
1               5                   10                  15

Gln Asn Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Glu Lys Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Gly Phe Asn Trp Thr
    130                 135                 140

Gly Val Thr Gln Ser Gly Gly Ser Tyr Ala Cys Lys Arg Gly Ser Asp
145                 150                 155                 160

Lys Ser Phe Phe Ser Arg Leu Asn Trp Leu Tyr Glu Ser Glu Ser Lys
                165                 170                 175

Tyr Pro Val Leu Asn Val Thr Met Pro Asn Asn Gly Asn Phe Asp Lys
            180                 185                 190

Leu Tyr Ile Trp Gly Val His His Pro Ser Thr Asp Lys Glu Gln Thr
        195                 200                 205

Asn Leu Tyr Val Arg Ala Ser Gly Arg Val Thr Val Ser Thr Lys Arg
    210                 215                 220

Ser Gln Gln Thr Ile Ile Pro Asn Ile Gly Ser Arg Pro Trp Val Arg
225                 230                 235                 240

Gly Leu Ser Ser Gly Ile Ser Ile Tyr Trp Thr Ile Val Lys Pro Gly
                245                 250                 255

Asp Ile Leu Leu Ile Asn Ser Asn Gly Asn Leu Ile Ala Pro Arg Gly
            260                 265                 270

Tyr Phe Lys Ile Arg Thr Gly Lys Ser Ser Ile Met Arg Ser Asp Ala
        275                 280                 285

Pro Ile Gly Thr Cys Ser Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
```

```
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565
```

<210> SEQ ID NO 11
<211> LENGTH: 1784
<212> TYPE: DNA
<213> ORGANISM: Influenza virus

<400> SEQUENCE: 11

```
gggcccctat aactctctac ggctaacctg aatggactac gacatagtct agtccgccaa     60

gatgaagacc atcattgccc tgagctacat cctgtgcctg gtgttcgccc agaagctgcc    120

cggcaacgac aatagcaccg ccaccctgtg tctgggccac cacgccgtgc ctaacggcac    180

cctggtgaaa accatcacca acgaccagat cgaagtgacc aacgccaccg agctggtgca    240

gagcagcagc accggcagaa tctgcgacag cccccaccgg atcctggacg gcaagaactg    300

caccctgatc gacgccctgc tgggcgaccc ccactgcgac ggcttccaga acaaagagtg    360

ggacctgttc gtggaaagaa gcaaggccta cagcaactgc taccctacg acgtgcccga    420

ctacgccagc ctgagaagcc tggtggccag cagcggcaca ctggaattca tcaacgagga    480

cttcaactgg accggcgtgg cccaggatgg cggcagctat gcctgcaaga gaggcagcgt    540

gaacagcttc ttcagcagac tgaactggct gcacaagagc gagtacaagt accccgccct    600

gaacgtgacc atgcccaaca acggcaagtt cgacaagctg tacatctggg gcgtgcacca    660

ccccagcacc gacagggacc agaccagcct gtacgtgcgg gccagcggca gagtgaccgt    720

gtccaccaag agaagccagc agaccgtgac ccccaacatc ggcagcagac cctgggtccg    780

cggccagagc agccggatca gcatctactg gaccatcgtg aagcccggcg acatcctgct    840
```

```
gatcaacagc acaggcaacc tgatcgcccc cagaggctac ttcaagatcc ggaacggcaa    900

gagcagcatc atgcggagcg acgcccccat cgggacctgc agcagcgagt gcatcacccc    960

caacggcagc atccccaacg acaagccctt ccagaacgtg aaccggatca cctacggcgc   1020

ctgccccaga tacgtgaagc agaacaccct gaagctggcc accggcatgc ggaacgtgcc   1080

cgagaagcag accagaggca tcttcggcgc cattgccggc ttcatcgaga acggctggga   1140

gggcatggtg gacggttggt acggcttccg gcaccagaac agcgagggca caggacaggc   1200

cgccgacctg aagtctaccc aggccgccat cgaccagatc aacggcaagc tgaacagact   1260

gatcgaaaag accaacgaga agttccacca gatcgagaaa gaattcagcg aggtggaagg   1320

ccggatccag gacctggaaa agtacgtgga agataccaag atcgacctgt ggtcctacaa   1380

cgccgagctg ctggtggccc tggaaaacca gcacaccatc gacctgaccg acagcgagat   1440

gaacaagctg ttcgagaaaa ccagaaagca gctgcgcgag aacgccgagg acatgggcaa   1500

cggctgcttc aagatctacc acaagtgcga caatgcctgc atcggcagca tccggaacgg   1560

cacctacgac cacgacgtgt acagggacga ggccctgaac aaccggttcc agatcaaggg   1620

cgtggaactg aagtccggct acaaggactg gatcctgtgg atcagcttcg ccatcagctg   1680

ctttctgctg tgcgtggtgc tgctgggctt catcatgtgg gcctgccaga aaggcaacat   1740

ccggtgcaac atctgcattt aaggcgcgcc cacccagcgg ccgc                    1784
```

```
<210> SEQ ID NO 12
<211> LENGTH: 566
<212> TYPE: PRT
<213> ORGANISM: Influenza virus

<400> SEQUENCE: 12

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Asn Glu Asp Phe Asn Trp Thr
    130                 135                 140

Gly Val Ala Gln Asp Gly Gly Ser Tyr Ala Cys Lys Arg Gly Ser Val
145                 150                 155                 160

Asn Ser Phe Phe Ser Arg Leu Asn Trp Leu His Lys Ser Glu Tyr Lys
                165                 170                 175

Tyr Pro Ala Leu Asn Val Thr Met Pro Asn Asn Gly Lys Phe Asp Lys
            180                 185                 190

Leu Tyr Ile Trp Gly Val His His Pro Ser Thr Asp Arg Asp Gln Thr
        195                 200                 205
```

```
Ser Leu Tyr Val Arg Ala Ser Gly Arg Val Thr Val Ser Thr Lys Arg
    210                 215                 220

Ser Gln Gln Thr Val Thr Pro Asn Ile Gly Ser Arg Pro Trp Val Arg
225                 230                 235                 240

Gly Gln Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Asn Gly Lys Ser Ser Ile Met Arg Ser Asp Ala
        275                 280                 285

Pro Ile Gly Thr Cys Ser Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565


<210> SEQ ID NO 13
<211> LENGTH: 1784
<212> TYPE: DNA
<213> ORGANISM: Influenza virus

<400> SEQUENCE: 13

gggcccctat aactctctac ggctaacctg aatggactac gacatagtct agtccgccaa     60
```

-continued

```
gatgaagacc atcattgccc tgagctacat cctgtgcctg gtgttcgccc agaagctgcc    120

cggcaacgac aatagcaccg ccaccctgtg tctgggccac cacgccgtgc ctaacggcac    180

catcgtgaaa accatcacca acgaccagat cgaagtgacc aacgccaccg agctggtgca    240

gagcagcagc accggcggca tctgcgacag cccccaccag atcctggacg gcgagaactg    300

caccctgatc gacgccctgc tgggcgaccc ccagtgcgac ggcttccaga acaagaaatg    360

ggacctgttc gtggaaagaa gcaaggccta cagcaactgc tacccctacg acgtgcccga    420

ctacgccagc ctgagaagcc tggtggccag cagcggcaca ctggaattca acaacgagag    480

cttcaactgg accggcgtga cccagaacgg caccagcagc gcctgcaaga gaagaagcaa    540

caagagcttc ttcagcagac tgaactggct gacccacctg aagtacaagt accccgccct    600

gaacgtgacc atgcccaaca acgaaaagtt cgacaagctg tacatctggg gcgtgctgca    660

ccccggcacc gacagcgacc agatcagcct gtacgcccag gccagcggca gaatcaccgt    720

gtccaccaag agaagccagc agaccgtgat ccccaacatc ggcagcagac ccagagtccg    780

cggcgtgagc agccggatca gcatctactg gaccatcgtg aagcccggcg acatcctgct    840

gatcaacagc accggcaacc tgatcgcccc cagaggctac ttcaagattc ggagcggcaa    900

gagcagcatc atgcggagcg acgcccccat cggcaagtgc aacagcgagt gcatcacccc    960

caacggcagc atccccaacg acaagccctt ccagaacgtg aaccggatca cctacggcgc   1020

ctgcccccgg tacatcaagc agaacaccct gaagctggcc accggcatgc ggaacgtgcc   1080

cgagaagcag accagaggca tcttcggcgc cattgccggc ttcatcgaga acggctggga   1140

gggcatggtg gacggttggt acggcttccg gcaccagaac agcgagggca caggacaggc   1200

cgccgacctg aagtctaccc aggccgccat caaccagatc aacggcaagc tgaacagact   1260

gatcggcaag accaacgaga agttccacca gatcgagaaa gaattcagcg aggtggaagg   1320

ccggatccag gacctggaaa agtacgtgga agataccaag atcgacctgt ggtcctacaa   1380

cgccgagctg ctggtggccc tggaaaacca gcacaccatc gacctgaccg acagcgagat   1440

gaacaagctg ttcgagcgga ccaagaagca gctgcgcgag aacgccgagg acatgggcaa   1500

cggctgcttc aagatctacc acaagtgcga caatgcctgc atcggcagca tccggaacgg   1560

cacctacgac cacgacgtgt acagggacga ggccctgaac aaccggttcc agatcaaggg   1620

cgtggaactg aagtccggct acaaggactg gatcctgtgg atcagcttcg ccatcagctg   1680

ctttctgctg tgcgtggccc tgctgggctt catcatgtgg gcctgccaga aaggcaacat   1740

ccggtgcaac atctgcattt aaggcgcgcc cacccagcgg ccgc                    1784


<210> SEQ ID NO 14
<211> LENGTH: 566
<212> TYPE: PRT
<213> ORGANISM: Influenza virus

<400> SEQUENCE: 14

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60
```

-continued

```
Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Lys Ser Phe Phe Ser Arg Leu Asn Trp Leu Thr His Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val Leu His Pro Gly Thr Asp Ser Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Gly Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Ile Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
```

```
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 15
<211> LENGTH: 1784
<212> TYPE: DNA
<213> ORGANISM: Influenza virus

<400> SEQUENCE: 15

gggcccctat aactctctac ggctaacctg aatggactac gacatagtct agtccgccaa      60

gatgaagacc atcattgccc tgagctacat cctgtgcctg gtgttcaccc agaagctgcc     120

cggcaacgac aatagcaccg ccaccctgtg tctgggccac cacgccgtgc ctaacggcac     180

catcgtgaaa accatcacca acgaccagat cgaagtgacc aacgccaccg agctggtgca     240

gagcagcagc accggcgaga tctgcgacag cccccaccag atcctggacg gcgagaactg     300

caccctgatc gacgccctgc tgggcgaccc ccagtgcgac ggcttccaga acaagaaatg     360

ggacctgttc gtggaaagaa gcaaggccta cagcaactgc taccccctacg acgtgcccga     420

ctacgccagc ctgagaagcc tggtggccag cagcggcaca ctggaattca acaacgagag     480

cttcaactgg accggcgtga cccagaacgg caccagcagc gcctgcatca gaagaagcaa     540

caacagcttc ttcagcagac tgaactggct gacccacctg aagttcaagt accccgccct     600

gaacgtgacc atgcccaaca acgaaaagtt cgacaagctg tacatctggg gcgtgcacca     660

ccccggcacc gacaacgatc agatcttccc atacgcccag gccagcggca gaatcaccgt     720

gtccaccaag agaagccagc agaccgtgat ccccaacatc ggcagcagac ccagagtccg     780

caacatcccc agccggatca gcatctactg gaccatcgtg aagcccggcg acatcctgct     840

gatcaacagc accggcaacc tgatcgcccc cagaggctac ttcaagattc ggagcggcaa     900

gagcagcatc atgcggagcg acgcccccat cggcaagtgc aacagcgagt gcatcacccc     960

caacggcagc atccccaacg acaagccctt ccagaacgtg aaccggatca cctacggcgc    1020

ctgccccaga tacgtgaagc agaacaccct gaagctggcc accggcatgc ggaacgtgcc    1080

cgagaagcag accagaggca tcttcggcgc cattgccggc ttcatcgaga acggctggga    1140

gggcatggtg gacggttggt acggcttccg gcaccagaac agcgagggca ttggacaggc    1200

cgccgacctg aagtctaccc aggccgccat cgaccagatc aacggcaagc tgaacagact    1260

gatcggcaag accaacgaga agttccacca gatcgagaaa gaattcagcg aggtggaagg    1320

ccggatccag gacctggaaa agtacgtgga agataccaag atcgacctgt ggtcctacaa    1380

cgccgagctg ctggtggccc tggaaaacca gcacaccatc gacctgaccg acagcgagat    1440

gaacaagctg ttcgagaaaa ccaagaagca gctgcgcgag aacgccgagg acatgggcaa    1500

cggctgcttc aagatctacc acaagtgcga caatgcctgc atcggcagca tccggaacgg    1560

cacctacgac cacaacgtgt acagggacga ggccctgaac aaccggttcc agatcaaggg    1620
```

```
cgtggaactg aagtccggct acaaggactg gatcctgtgg atcagcttcg ccatcagctg   1680

ctttctgctg tgcgtggccc tgctgggctt catcatgtgg gcctgccaga aaggcaacat   1740

ccggtgcaac atctgcattt aaggcgcgcc cacccagcgg ccgc                     1784


<210> SEQ ID NO 16
<211> LENGTH: 566
<212> TYPE: PRT
<213> ORGANISM: Influenza virus

<400> SEQUENCE: 16

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Pro Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350
```

```
Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asn Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565
```

<210> SEQ ID NO 17
<211> LENGTH: 1784
<212> TYPE: DNA
<213> ORGANISM: Influenza virus

<400> SEQUENCE: 17

```
gggcccctat aactctctac ggctaacctg aatggactac gacatagtct agtccgccaa     60

gatgaagacc atcattgccc tgagctacat cctgtgcctg gtgttcgccc agaagctgcc    120

cggcaacgac aatagcaccg ccaccctgtg tctgggccac cacgccgtgc ctaacggcac    180

catcgtgaaa accatcacca acgaccggat cgaagtgacc aacgccaccg agctggtgca    240

gaacagcagc atcggcgaga tctgcgacag cccccaccag atcctggacg gcgagaactg    300

caccctgatc gacgccctgc tgggcgaccc ccagtgcgac ggcttccaga acaagaaatg    360

ggacctgttc gtggaaagaa gcaaggccta cagcaactgc taccctacg acgtgcccga    420

ctacgccagc ctgagaagcc tggtggccag cagcggcaca ctggaattca acaacgagag    480

cttcaactgg aacggcgtga cccagaacgg caccagcagc gcctgcatca gaagaagcaa    540

caacagcttc ttcagcagac tgaactggct gacccacctg aacttcaagt accccgccct    600

gaacgtgacc atgcccaaca acgagcagtt cgacaagctg tacatctggg gcgtgcacca    660

ccccggcacc gacaaggacc agatcttcct gtacgcccag cccagcggca gaatcaccgt    720

gtccaccaag agaagccagc aggccgtgat ccccaacatc ggcagcagac cccggatccg    780

caacatcccc agccggatca gcatctactg gaccatcgtg aagcccggcg acatcctgct    840
```

-continued

```
gatcaacagc accggcaacc tgatcgcccc cagaggctac ttcaagattc ggagcggcaa    900

gagcagcatc atgcggagcg acgcccccat cggcaagtgc aagagcgagt gcatcacccc    960

caacggcagc atccccaacg acaagccctt ccagaacgtg aaccggatca cctacggcgc   1020

ctgccccaga tacgtgaagc agagcaccct gaagctggcc accggcatgc ggaacgtgcc   1080

cgagaagcag accagaggca tcttcggcgc cattgccggc ttcatcgaga acggctggga   1140

gggcatggtg gacggttggt acggcttccg gcaccagaac agcgagggca gaggacaggc   1200

cgccgacctg aagtctaccc aggccgccat cgaccagatc aacggcaagc tgaacagact   1260

gatcggcaag accaacgaga agttccacca gatcgagaaa gaattcagcg aggtggaagg   1320

ccggatccag gacctggaaa agtacgtgga agataccaag atcgacctgt ggtcctacaa   1380

cgccgagctg ctggtggccc tggaaaacca gcacaccatc gacctgaccg acagcgagat   1440

gaacaagctg ttcgagaaaa ccaagaagca gctgcgcgag aacgccgagg acatgggcaa   1500

cggctgcttc aagatctacc acaagtgcga caatgcctgc atcggcagca tccggaacgg   1560

cacctacgac cacgacgtgt acagggacga ggccctgaac aaccggttcc agatcaaggg   1620

cgtggaactg aagtccggct acaaggactg gatcctgtgg atcagcttcg ccatcagctg   1680

ctttctgctg tgcgtggccc tgctgggctt catcatgtgg gcctgccaga aaggcaacat   1740

ccggtgcaac atctgcattt aaggcgcgcc cacccagcgg ccgc                    1784


<210> SEQ ID NO 18
<211> LENGTH: 566
<212> TYPE: PRT
<213> ORGANISM: Influenza virus

<400> SEQUENCE: 18

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Arg Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Asn
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205
```

```
Phe Leu Tyr Ala Gln Pro Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Lys Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Ser Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560

Arg Cys Asn Ile Cys Ile
                565


<210> SEQ ID NO 19
<211> LENGTH: 1695
<212> TYPE: DNA
<213> ORGANISM: Influenza virus

<400> SEQUENCE: 19

atggagaaaa tagtgcttct tcttgcaata gtcagccttg ttaaaagtga tcagatttgc      60
```

-continued

```
attggttacc atgcaaacaa ctcgacagag caggttgaca caataatgga aaagaacgtc    120
actgttacac acgcccaaga catactggaa aagacacaca acgggaaact ctgcgatcta    180
gatggagtga agcctctaat tttaagagat tgtagtgtag ctggatggct cctcgggaac    240
ccaatgtgtg acgaattcct caatgtgccg gaatggtctt acatagtgga gaagatcaat    300
ccagccaatg acctctgtta cccagggaat ttcaacgact atgaagaact gaaacaccta    360
ttgagcagaa taaaccattt tgagaaaatt cagatcatcc ccaaaagttc ttggtcagat    420
catgaagcct cagcaggggt gagctcagca tgtccatacc agggaaggtc ctcctttttt    480
agaaatgtgg tatggcttat caaaaaggac aatgcatacc caacaataaa gagaagttac    540
aataatacca accaagaaga tcttttggta ttgtggggga ttcaccatcc aaatgatgcg    600
gcagagcaga caaggctcta tcaaaaccca actacctata tttccgttgg gacatcaaca    660
ctaaaccaga gattggtacc aaaaatagcc actagatcta aggtaaacgg gcaaagtgga    720
aggatggagt tcttttggac aattttaaaa ccgaatgatg caataaactt tgagagtaat    780
ggaaatttca ttgctccaga aaatgcatac aaaattgtca agaaagggga ctcaacaatt    840
atgaaaagtg agttggaata tggtaactgc aacaccaagt gtcaaactcc aataggggcg    900
ataaactcta gtatgccatt ccacaacatc caccctctca ccatcgggga atgccccaaa    960
tatgtgaaat caagcagatt agtccttgct actgggctca gaaatagccc tcaacgagag   1020
acacgaggac tatttggagc tatagcaggt tttatagagg gaggatggca gggaatggta   1080
gatggttggt atgggtacca ccatagcaac gagcagggga gtgggtacgc tgcagacaaa   1140
gaatccactc aaaaggcaat agatggagtc accaataagg tcaactcgat cattgacaaa   1200
atgaacactc agtttgaggc tgttggaagg gaatttaata acttagaaag gagaatagaa   1260
aatttaaaca agaagatgga agacggattc ctagatgtct ggacttataa tgctgaactt   1320
ctggttctca tggaaaatga gagaactcta gactttcatg actcaaatgt caagaacctt   1380
tacgacaagg tccgactaca gcttagggat aatgcaaagg agcttggtaa cggttgtttc   1440
gagttctatc acagatgtga taatgaatgt atggaaagtg taagaaacgg aacgtatgac   1500
tacccgcagt attcagaaga agcaagatta aaaagagagg aaataagtgg agtaaaattg   1560
gaatcaatag gaacttacca aatactgtca atttattcaa cagtggcgag ctccctagca   1620
ctggcaatca tggtggctgg tctatcttta tggatgtgct ccaatggatc gttacaatgc   1680
agaatttgca tttaa                                                    1695
```

```
<210> SEQ ID NO 20
<211> LENGTH: 564
<212> TYPE: PRT
<213> ORGANISM: Influenza virus

<400> SEQUENCE: 20

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80
```

-continued

```
Pro Met Cys Asp Glu Phe Leu Asn Val Pro Glu Trp Ser Tyr Ile Val
                85                  90                  95

Glu Lys Ile Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ala Gly Val Ser Ser Ala Cys Pro Tyr Gln Gly Arg Ser Ser Phe Phe
145                 150                 155                 160

Arg Asn Val Val Trp Leu Ile Lys Lys Asp Asn Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Asn Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Ile Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Ser Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Arg Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
```

```
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile
```

<210> SEQ ID NO 21
<211> LENGTH: 1516
<212> TYPE: DNA
<213> ORGANISM: Influenza virus

<400> SEQUENCE: 21

```
atgaacactc aaatcctggt attcgctctg attgcgatca ttccaacaaa tgcagacaaa     60

atctgcctcg gacatcatgc cgtgtcaaac ggaaccaaag taaacacatt aactgaaaga    120

ggagtggaag tcgtcaatgc aactgaaaca gtggaacgaa caaacatccc caggatctgc    180

tcaaaaggga aaaggacagt tgacctcggt caatgtggac tcctggggac aatcactgga    240

ccacctcaat gtgaccaatt cctagaattt tcagccgatt taattattga gaggcgagaa    300

ggaagtgatg tctgttatcc tgggaaattc gtgaatgaag aagctctgag gcaaattctc    360

agagaatcag gcggaattga caaggaagca atgggattca catacagtgg aataagaact    420

aatggagcaa ccagtgcatg taggagatca ggatcttcat tctatgcaga aatgaaatgg    480

ctcctgtcaa acacagataa tgctgcattc ccgcagatga ctaagtcata taaaaataca    540

agaaaaagcc cagctctaat agtatggggg atccatcatt ccgtatcaac tgcagagcaa    600

accaagctat atgggagtgg aaacaaactg gtgacagttg ggagttctaa ttatcaacaa    660

tcttttgtac cgagtccagg agcgagacca caagttaatg gtctatctgg aagaattgac    720

tttcattggc taatgctaaa tcccaatgat acagtcactt tcagtttcaa tggggctttc    780

atagctccag accgtgcaag cttcctgaga ggaaaatcta tgggaatcca gagtggagta    840

caggttgatg ccaattgtga aggggactgc tatcatagtg gagggacaat aataagtaac    900

ttgccatttc agaacataga tagcagggca gttggaaaat gtccgagata tgttaagcaa    960

aggagtctgc tgctagcaac agggatgaag aatgttcctg agattccaaa aggaagaggc   1020

ctatttggtg ctatagcggg tttcattgaa aatggatggg aaggcctaat tgatggttgg   1080

tatggtttca gacaccagaa tgcacaggga gagggaactg ctgcagatta caaaagcact   1140

caatcggcaa ttgatcaaat aacaggaaaa ttaaaccggc ttatagaaaa aaccaaccaa   1200

caatttgagt tgatagacaa tgaattcaat gaggtagaga agcaaatcgg taatgtgata   1260

aattggacca gagattctat aacagaagtg tggtcataca atgctgaact cttggtagca   1320

atggagaacc agcatacaat tgatctggct gattcagaaa tggacaaact gtacgaacga   1380

gtgaaaagac agctgagaga gaatgctgaa gaagatggca ctggttgctt tgaaatattt   1440

cacaagtgtg atgatgactg tatggccagt attagaaata acacctatga tcacagcaaa   1500

tacagggaag aggcaa                                                   1516
```

<210> SEQ ID NO 22
<211> LENGTH: 506
<212> TYPE: PRT
<213> ORGANISM: Influenza virus
<220> FEATURE:

<221> NAME/KEY: misc_feature
<222> LOCATION: (506)..(506)
<223> OTHER INFORMATION: Xaa can be any naturally occurring amino acid

<400> SEQUENCE: 22

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
```

-continued

```
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Xaa
            500                 505


<210> SEQ ID NO 23
<211> LENGTH: 41
<212> TYPE: DNA
<213> ORGANISM: Artificial Sequence
<220> FEATURE:
<223> OTHER INFORMATION: forward primer for influenza H1N1
      A/California/07/2009 insert

<400> SEQUENCE: 23

attcccgtcg acgccaccat gaaggcaata ctagtagttc t                           41


<210> SEQ ID NO 24
<211> LENGTH: 44
<212> TYPE: DNA
<213> ORGANISM: Artificial Sequence
<220> FEATURE:
<223> OTHER INFORMATION: reverse primer for influenza H1N1
      A/California/07/2009 insert

<400> SEQUENCE: 24

atttacgcct aggttatcaa atacatattc tacactgtag agac                        44


<210> SEQ ID NO 25
<211> LENGTH: 43
<212> TYPE: DNA
<213> ORGANISM: Artificial Sequence
<220> FEATURE:
<223> OTHER INFORMATION: forward primer for H7 HA gene from
      A/Shanghai/2/2013

<400> SEQUENCE: 25

aattaagtcg acgccaccat gaacactcaa atcctggtat tcg                         43


<210> SEQ ID NO 26
<211> LENGTH: 40
<212> TYPE: DNA
<213> ORGANISM: Artificial Sequence
<220> FEATURE:
<223> OTHER INFORMATION: reverse primer for H7 HA gene from
      A/Shanghai/2/2013

<400> SEQUENCE: 26

aattaatcta gattatcata tacaaatagt gcaccgcatg                             40


<210> SEQ ID NO 27
<211> LENGTH: 15
<212> TYPE: PRT
```

-continued

```
<213> ORGANISM: Artificial Sequence
<220> FEATURE:
<223> OTHER INFORMATION: 27 peptide

<400> SEQUENCE: 27

Ala Leu Asn Asn Arg Phe Gln Ile Lys Gly Val Glu Leu Lys Ser
1               5                   10                  15


<210> SEQ ID NO 28
<211> LENGTH: 47
<212> TYPE: DNA
<213> ORGANISM: Artificial Sequence
<220> FEATURE:
<223> OTHER INFORMATION: SB63 primer

<400> SEQUENCE: 28

catagtctag tcgacgccac catggagaaa atagtgcttc ttcttgc                   47


<210> SEQ ID NO 29
<211> LENGTH: 95
<212> TYPE: DNA
<213> ORGANISM: Artificial Sequence
<220> FEATURE:
<223> OTHER INFORMATION: SB74 primer

<400> SEQUENCE: 29

gtcgaagttc agggtctgct tcacgggggc cacgatcttc tgcttgtgcc gggcctcccg     60

cttggcccga atgcaaattc tgcattgtaa cgatc                                95


<210> SEQ ID NO 30
<211> LENGTH: 91
<212> TYPE: DNA
<213> ORGANISM: Artificial Sequence
<220> FEATURE:
<223> OTHER INFORMATION: SB76 primer

<400> SEQUENCE: 30

gtgaagcaga ccctgaactt cgacctgctg aagctggccg gcgacgtgga gagcaacccc     60

ggccccatga aggcaatact agtagttctg c                                    91


<210> SEQ ID NO 31
<211> LENGTH: 51
<212> TYPE: DNA
<213> ORGANISM: Artificial Sequence
<220> FEATURE:
<223> OTHER INFORMATION: SB66 primer

<400> SEQUENCE: 31

ggcgtagcgg cggccgctta tcaaatacat attctacact gtagagaccc a              51
```